(12) United States Patent
Kataoka et al.

(10) Patent No.: US 9,056,862 B2
(45) Date of Patent: Jun. 16, 2015

(54) THIOXOTHIAZOLIDINE DERIVATIVE HAVING RAS FUNCTION INHIBITORY EFFECT

(75) Inventors: Tohru Kataoka, Kobe (JP); Fumi Shima, Kobe (JP); Masahiro Neya, Kobe (JP); Daisuke Sasahara, Kobe (JP)

(73) Assignees: NATIONAL UNIVERSITY CORPORATION KOBE UNIVERSITY, Hyogo (JP); KNC LABORATORIES CO., LTD., Hyogo (JP)

( * ) Notice: Subject to any disclaimer, the term of this patent is extended or adjusted under 35 U.S.C. 154(b) by 0 days.

(21) Appl. No.: 14/116,152

(22) PCT Filed: May 9, 2012

(86) PCT No.: PCT/JP2012/061908
§ 371 (c)(1),
(2), (4) Date: Jan. 17, 2014

(87) PCT Pub. No.: WO2012/153775
PCT Pub. Date: Nov. 15, 2012

(65) Prior Publication Data
US 2014/0194412 A1 Jul. 10, 2014

(30) Foreign Application Priority Data
May 10, 2011 (JP) ................ 2011-105613

(51) Int. Cl.
| C07D 417/06 | (2006.01) |
| C07D 417/12 | (2006.01) |
| C07D 417/14 | (2006.01) |
| C07D 277/46 | (2006.01) |
| C07D 277/40 | (2006.01) |
| C07D 277/28 | (2006.01) |
| C07D 277/30 | (2006.01) |
| C07D 277/24 | (2006.01) |
| C07D 419/12 | (2006.01) |
| C07D 277/20 | (2006.01) |
| C07D 277/36 | (2006.01) |

(52) U.S. Cl.
CPC ............ *C07D 417/14* (2013.01); *C07D 277/46* (2013.01); *C07D 277/40* (2013.01); *C07D 277/28* (2013.01); *C07D 277/30* (2013.01); *C07D 277/24* (2013.01); *C07D 417/06* (2013.01); *C07D 417/12* (2013.01); *C07D 419/12* (2013.01); *C07D 277/20* (2013.01); *C07D 277/36* (2013.01)

(58) Field of Classification Search
USPC ......................................................... 548/181
See application file for complete search history.

(56) References Cited

U.S. PATENT DOCUMENTS

| 5,523,314 A | 6/1996 | Bue-Valleskey et al. |
| 5,661,168 A | 8/1997 | Panetta et al. |
| 5,716,975 A | 2/1998 | Bue-Valleskey et al. |
| 5,807,873 A | 9/1998 | Nicolai et al. |
| 6,180,651 B1 | 1/2001 | Nicolai et al. |
| 6,673,816 B1 | 1/2004 | Esswein et al. |
| 2003/0032813 A1 | 2/2003 | Esswein et al. |
| 2003/0144301 A1 | 7/2003 | Ayral-Kaloustian et al. |
| 2003/0144329 A1 | 7/2003 | Pfahl et al. |
| 2003/0149063 A1 | 8/2003 | Epstein et al. |
| 2003/0216432 A1 | 11/2003 | Pfahl et al. |
| 2004/0034004 A1 | 2/2004 | Pfahl et al. |
| 2004/0063695 A1 | 4/2004 | Verkman et al. |
| 2004/0142991 A1 | 7/2004 | Nag et al. |
| 2004/0235800 A1 | 11/2004 | Verkman et al. |
| 2005/0096366 A1 | 5/2005 | Nag et al. |
| 2005/0288341 A1 | 12/2005 | Nag et al. |
| 2006/0106077 A1 | 5/2006 | Suto et al. |
| 2006/0142294 A1 | 6/2006 | Neamati et al. |
| 2006/0160796 A1 | 7/2006 | Pfahl et al. |
| 2006/0183782 A1 | 8/2006 | Zhang et al. |
| 2006/0235034 A1 | 10/2006 | Neamati |
| 2006/0241138 A1 | 10/2006 | Pfahl et al. |
| 2006/0247285 A1 | 11/2006 | Neogi et al. |
| 2008/0064666 A1 | 3/2008 | Verkman et al. |

(Continued)

FOREIGN PATENT DOCUMENTS

| EP | 0 587 377 A2 | 3/1994 |
| EP | 677517 A1 * | 10/1995 |

(Continued)

OTHER PUBLICATIONS

Chemical Abstracts Registry No. 381671-39-2, indexed in the Registry file on STN CAS Online Jan. 10, 2002.*

(Continued)

*Primary Examiner* — Laura L. Stockton
(74) *Attorney, Agent, or Firm* — Sughrue Mion, PLLC

(57) ABSTRACT

The present invention provides an anticancer drug having a Ras function inhibitory action.
The present invention provides a Ras function inhibitor comprising a compound represented by the formula (I'):

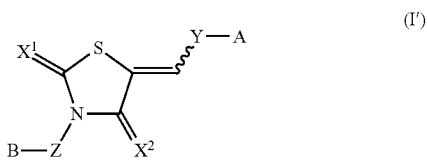

wherein each symbol is as defined in the present specification, or a salt thereof.

25 Claims, No Drawings

(56) References Cited

U.S. PATENT DOCUMENTS

| | | |
|---|---|---|
| 2008/0108677 A1 | 5/2008 | Bjorklund et al. |
| 2008/0267888 A1 | 10/2008 | Pandey et al. |
| 2009/0093489 A1 | 4/2009 | Neamati et al. |
| 2009/0163545 A1* | 6/2009 | Goldfarb .............. 514/312 |
| 2010/0120781 A1 | 5/2010 | Neamati |
| 2010/0130571 A1 | 5/2010 | Verkman et al. |
| 2010/0305174 A1 | 12/2010 | Pandey et al. |
| 2011/0034472 A1 | 2/2011 | Neamati et al. |
| 2011/0263664 A1 | 10/2011 | Smith et al. |
| 2011/0275646 A1 | 11/2011 | Neamati et al. |
| 2012/0302581 A1 | 11/2012 | Ratner et al. |

FOREIGN PATENT DOCUMENTS

| | | | |
|---|---|---|---|
| GB | 2 386 892 A | 10/2003 | |
| WO | 00/18747 A1 | 4/2000 | |
| WO | WO-01/77091 A2 * | 10/2001 | |
| WO | 03/018135 A1 | 3/2003 | |
| WO | 03/043998 A1 | 5/2003 | |
| WO | 03/094916 A1 | 11/2003 | |
| WO | 2004/028480 A2 | 4/2004 | |
| WO | WO-2004/093803 A2 * | 11/2004 | |
| WO | 2005/007123 A2 | 1/2005 | |
| WO | 2006/024699 A1 | 3/2006 | |
| WO | 2006/089225 A1 | 8/2006 | |
| WO | 2006/091246 A1 | 8/2006 | |
| WO | 2006/109146 A2 | 10/2006 | |
| WO | 2006/126074 A2 | 11/2006 | |
| WO | 2007/097992 A2 | 8/2007 | |
| WO | WO-2008/109731 A2 * | 9/2008 | |
| WO | 2009/064486 A2 | 5/2009 | |
| WO | 2010/094009 A2 | 8/2010 | |

OTHER PUBLICATIONS

Chemical Abstracts Registry No. 381671-38-1, indexed in the Registry file on STN CAS Online Jan. 10, 2002.*
Chemical Abstracts Registry No. 292163-05-4, indexed in the Registry file on STN CAS Online Oct. 3, 2000.*
Chemical Abstracts Registry No. 292075-73-1, indexed in the Registry file on STN CAS Online Oct. 2, 2000.*
Hardej et al., European Journal of Medicinal Chemistry, (2010), 45(12), pp. 5827-5832.*
Bursavich et al., Bioorganic & Medicinal Chemistry Letters, (2007), 17(5), pp. 1185-1188.*
Chemical Abstracts Registry No. 872519-50-1, indexed in the Registry file on Jan. 24, 2006.*
Chemical Abstracts Registry No. 872519-39-6, indexed in the Registry file on Jan. 24, 2006.*
Chemical Abstracts Registry No. 872519-24-9, indexed in the Registry file on Jan. 24, 2006.*
Chemical Abstracts Registry No. 872518-99-5, indexed in the Registry file on Jan. 24, 2006.*
Chemical Abstracts Registry No. 401607-95-2, indexed in the Registry file on Mar. 18, 2002.*
Chemical Abstracts Registry No. 591212-89-4, indexed in the Registry file on Sep. 23, 2003.*
Chemical Abstracts Registry No. 591242-12-5, indexed in the Registry file on Sep. 23, 2003.*
Chemical Abstracts Registry No. 292173-48-9, indexed in the Registry file on Oct. 3, 2000.*
Chemical Abstracts Registry No. 292077-02-2, indexed in the Registry file on Oct. 2, 2000.*
Chemical Abstracts Registry No. 292077-01-1, indexed in the Registry file on Oct. 2, 2000.*
Chemical Abstracts Registry No. 292076-96-1, indexed in the Registry file on Oct. 2, 2000.*
Pesnot et al., ChemBioChem, (2010), 11(10), pp. 1392-1398.*
Albers et al., Journal of Medicinal Chemistry, (2010), 53(13), pp. 4958-4967.*
Mori et al., Journal of Pesticide Science (Tokyo, Japan), 2008, 33(4), pp. 357-363.*
PubChem CID 1207621, created Jul. 10, 2005.*
PubChem CID 6017749, created Sep. 13, 2005.*
STK064369—Compound Summary, PubChem Compound, Jul. 10, 2005, pp. 1-4.
Sarah A. Holstein et al., "Isoprenoid Pyrophosphate Analogues Regulate Expression of Ras-Related Proteins," Biochemistry, 2003, pp. 4384-4391, vol. 42.
Christopher J. D. Mau et al., "Protein farnesyltransferase inhibitors interfere with farnesyl diphosphate binding by rubber transferase," Eur. J. Biochem., 2003, pp. 3939-3945, vol. 270.
Mitsunobu Hara et al., "Identification of Ras farnesyltransferase inhibitors by microbial screening," Proc. Natl. Acad. Sci., 1993, pp. 2281-2285, vol. 90.
Mark R. Lackner et al., "Chemical genetics identifies Rab geranylgeranyl transferase as an apoptotic target of farnesyl transferase inhibitors," Cancer Cell, Apr. 2005, pp. 325-336, vol. 7.
International Search Report of PCT/JP2012/061908 dated Jun. 5, 2012.

* cited by examiner

THIOXOTHIAZOLIDINE DERIVATIVE HAVING RAS FUNCTION INHIBITORY EFFECT

CROSS REFERENCE TO RELATED APPLICATIONS

This is a National Stage of International Application No. PCT/JP2012/061908, filed May 9, 2012, claiming priority from Japanese Patent Application No. 2011-105613, filed May 10, 2011.

TECHNICAL FIELD

The present invention relates to a compound having Ras function inhibitory action, which is useful as anticancer drug.

BACKGROUND ART

Ras, a product of ras oncogene, is a low-molecular-weight G protein, which consists of three Ras isoforms, H-Ras, N-Ras and K-Ras, in mammals. Since, constitutive activation of Ras function by the mutations of any of H-Ras, N-Ras and K-Ras is observed in human cancers with a high frequency, Ras is considered to be an eligible molecular target for development of anti-cancer drugs.

Ras controls signal transduction by cycling between GTP-bound active Ras (Ras-GTP) and GDP-bound inactive Ras (Ras-GDP) forms. In response to the binding of ligands (extracellular signal) such as cell growth factors to the receptors in cell membrane, Ras-GDP is activated by exchanging its GDP to GTP, and the resulting Ras-GTP transmits cell growth signals via binding to target molecules. Then, Ras-GTP is converted to Ras-GDP by the action of the factors (GTPase-activating proteins: GAPs) which promote intrinsic GTP hydrolysis (GTPase) activity of Ras, and the resulting Ras-GDP holds its inactive form until the next extracellular signal stimulation. In human cancers, the intrinsic GTP hydrolysis activity of Ras is impaired by Ras mutations (the active-form mutations). Further, the resulting mutants are unresponsive to the GTP hydrolysis-promoting action by GAPs, leading to abundance of an active form, Ras-GTP, in cells. Consequently, Ras continues to transmit cell growth signals leading to cancer development.

Since a Ras function inhibitor is a promising candidate as anticancer drug, its development has been desired. Farnesyl transferase inhibitors (FTIs) (Non-Patent Documents 1-4), which inhibit post translational lipid modification farnesylation of Ras, have been developed as a Ras function inhibitor. However, since they could not prolong the survival period of the drug-treated cancer patients, their development has been brought to a halt. At present, there is no effective therapeutic agent (drug) in the world.

Since the ratio of GTP-bound form in a cell is increased by Ras mutation in a human cancer, Ras-GTP is considered to be the most promising target for development of a Ras function inhibitor.

As compounds having a structure similar to that of the compounds described in the present specification, for example, compounds having a thioxothiazolidine skeleton are disclosed in Patent Documents 1 to 12. However, none of these documents disclose that such compound is a Ras function inhibitor.

DOCUMENT LIST

Patent Document

Patent Document 1: WO 2007/097992
Patent Document 2: WO 2006/126074
Patent Document 3: WO 2006/109146
Patent Document 4: WO 2006/089225
Patent Document 5: WO 2006/024699
Patent Document 6: WO 2005/007123
Patent Document 7: WO 2004/028480
Patent Document 8: WO 03/094916
Patent Document 9: GB 2386892A
Patent Document 10: WO 03/043998
Patent Document 11: WO 00/18747
Patent Document 12: EP 0587377A2

Non-Patent Document

Non-Patent Document 1: Biochemistry 42, 4384-91, (2003)
Non-Patent Document 2: Eur J Biochem 270, 3939-45, (2003)
Non-Patent Document 3: Proc Natl Acad Sci USA. 90, 2281-2285, (1993)
Non-Patent Document 4: Cancer Cell 7, 325-36, (2005)

SUMMARY OF THE INVENTION

Problems to be Solved by the Invention

The present invention aims to provide an anticancer drug having a Ras function inhibitory action.

Means of Solving the Problems

The present inventors have conducted intensive studies, and have found that the compound represented by the following formula has an excellent Ras function inhibitory action, and completed the present invention based on these findings.

Accordingly, the present invention provides the following.

[1] Ras function inhibitor comprising a compound represented by the formula (I'):

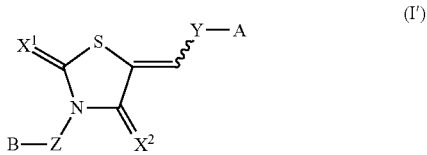

wherein

A is an optionally substituted cyclic group or an optionally substituted chain hydrocarbon group;

B is a hydrogen atom, an optionally substituted cyclic group, an optionally substituted amino group, an optionally substituted hydroxy group or an optionally esterified or amidated carboxy group;

$X^1$ and $X^2$ are each independently an oxygen atom or a sulfur atom; and

Y and Z are each independently a bond or a spacer having 1 to 6 atoms, or a salt thereof.

[2] A compound represented by the formula (I):

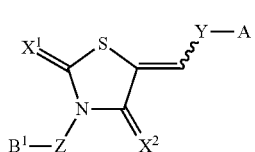
(I)

wherein
A is an optionally substituted cyclic group or an optionally substituted chain hydrocarbon group;
$B^1$ is a group represented by

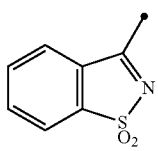

wherein • means a bonding site (i.e., 1,1-dioxido-1,2-benzisothiazol-3-yl group), which is an optionally substituted;
$X^1$ and $X^2$ are each independently an oxygen atom or a sulfur atom; and
Y and Z are each independently a bond or a spacer having 1 to 6 atoms,
or a salt thereof.
[3] The compound or salt of the above-mentioned [2], wherein the partial structure represented by

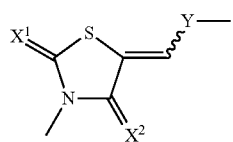

is a partial structure represented by

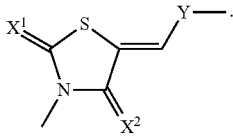

[4] The compound or salt of the above-mentioned [2], wherein A is an optionally substituted cyclic group.
[5] The compound or salt of the above-mentioned [2], wherein A is an optionally substituted $C_{6-14}$ aryl group.
[6] The compound or salt of the above-mentioned [2], wherein A is an optionally substituted phenyl group.
[7] The compound or salt of the above-mentioned [2], wherein $X^1$ is a sulfur atom.
[8] The compound or salt of the above-mentioned [2], wherein $X^2$ is an oxygen atom.
[9] The compound or salt of the above-mentioned [2], wherein Y is a bond.
[10] The compound or salt of the above-mentioned [2], wherein Z is —NH—.

[11] A compound represented by the formula (II):

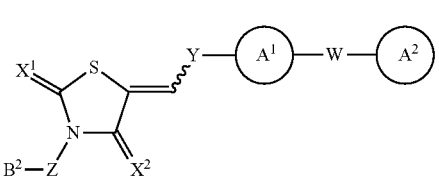
(II)

wherein
ring $A^1$ and ring $A^2$ are each independently an optionally substituted benzene ring;
$B^2$ is an optionally substituted cyclic group or an optionally substituted amino group;
$X^1$ and $X^2$ are each independently an oxygen atom or a sulfur atom;
Y and Z are each independently a bond or a spacer having 1 to 6 atoms; and
W is an oxygen atom, a sulfur atom, or a group represented by the formula: —$V^1$—$(CH_2)m$-$V^2$— wherein $V^1$ and $V^2$ are each independently a bond, an oxygen atom or a sulfur atom, and m is an integer of 1 to 3,
or a salt thereof.
[12] The compound or salt of the above-mentioned [11], wherein the partial structure represented by

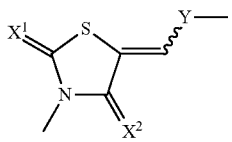

is a partial structure represented by

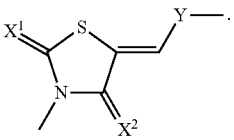

[13] The compound or salt of the above-mentioned [11], wherein ring $A^1$ and ring $A^2$ are both benzene rings.
[14] The compound or salt of the above-mentioned [11], wherein W is an oxygen atom, or a group represented by the formula: —$V^1$—$(CH_2)m$-$V^2$— wherein $V^1$ and $V^2$ are oxygen atoms, and m is an integer of 1 to 3.
[15] The compound or salt of the above-mentioned [11], wherein W is an oxygen atom or —$OCH_2CH_2O$—.
[16] The compound or salt of the above-mentioned [11], wherein $B^2$ is an optionally substituted 5- or 6-membered cyclic group, or an amino group (in this case, Z is a bond).
[17] The compound or salt of the above-mentioned [11], wherein $X^1$ is a sulfur atom.
[18] The compound or salt of the above-mentioned [11], wherein $X^2$ is an oxygen atom.
[19] The compound or salt of the above-mentioned [11], wherein Y is a bond.
[20] The compound or salt of the above-mentioned [11], wherein Z is a bond, or a group represented by —$(CH_2)n^1$-$V^3$—$(CH_2)n^2$- wherein $V^3$ is a bond, —CO— or —CONH—, and $n^1$ and $n^2$ are each independently an integer of 0 to 2.

[21] The compound or salt of the above-mentioned [11], wherein Z is a bond, —CONH—, —COCH₂—, —CH₂— or —(CH₂)₂—.
[22] A pharmaceutical composition comprising the compound or salt of any of the above-mentioned [2] to [21] and a pharmacologically acceptable carrier.
[23] An anticancer drug comprising the compound or salt of any of the above-mentioned [2] to [21].

Effect of the Invention

Since compound (I') has a Ras function inhibitory action, it is useful as an anticancer drug.

DESCRIPTION OF EMBODIMENTS

The definition of each symbol in the formulas is explained in detail below.

Examples of the "halogen atom" in the present specification include a fluorine atom, a chlorine atom, a bromine atom and an iodine atom.

Examples of the "$C_{1-6}$ alkyl (group)" in the present specification include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl and the like.

Examples of the "$C_{1-10}$ alkyl group" in the present specification include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Examples of the "$C_{2-6}$ alkenyl group" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

Examples of the "$C_{2-10}$ alkenyl group" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Examples of the "$C_{2-6}$ alkynyl group" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

Examples of the "$C_{2-10}$ alkynyl group" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

Examples of the "$C_{1-6}$ alkoxy (group)" in the present specification include methoxy, ethoxy, propoxy, isopropoxy, butoxy, isobutoxy, sec-butoxy, tert-butoxy and the like.

Examples of the "$C_{3-8}$ cycloalkyl (group)" in the present specification include cyclopropyl, cyclobutyl, cyclopentyl, cyclohexyl, cycloheptyl and cyclooctyl.

Examples of the "$C_{3-8}$ cycloalkenyl (group)" in the present specification include cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl) and cyclohexenyl (e.g., 2-cyclohexen-1-yl, 3-cyclohexen-1-yl).

Examples of the "$C_{4-8}$ cycloalkadienyl (group)" in the present specification include 2,4-cyclopentadien-1-yl, 2,4-cyclohexadien-1-yl, 2,5-cyclohexadien-1-yl and the like.

Examples of the "$C_{6-14}$ aryl (group)" in the present specification include phenyl, naphthyl, anthryl, phenanthryl, acenaphthylenyl, biphenylyl and the like. The "$C_{6-14}$ aryl (group)" is optionally fused with other ring(s), and examples thereof include fluorenyl, dihydronaphthyl, tetrahydronaphthyl and the like. Among them, a $C_{6-10}$ aryl group is preferable, and phenyl is particularly preferable.

Examples of the "$C_{7-13}$ aralkyl (group)" in the present specification include benzyl, phenethyl, naphthylmethyl, biphenylylmethyl and the like. Among them, a $C_{7-10}$ aralkyl group is preferable, and a benzyl group is particularly preferable.

Examples of the "heterocycle (group)" in the present specification include an aromatic heterocyclic group and a non-aromatic heterocyclic group.

Examples of the "aromatic heterocyclic group" in the present specification include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include monocyclic aromatic heterocyclic groups such as furyl, thienyl, pyridyl, pyrimidinyl, pyridazinyl, pyrazinyl, pyrrolyl, imidazolyl, pyrazolyl, triazolyl, isothiazolyl, oxazolyl, isoxazolyl, oxadiazolyl, thiadiazolyl, triazolyl, tetrazolyl, triazinyl and the like;

fused aromatic heterocyclic groups such as quinolyl, isoquinolyl, quinazolyl, quinoxalyl, benzofuranyl, benzothienyl, benzoxazolyl, benzisoxazolyl, benzothiazolyl, benzimidazolyl, benzotriazolyl, indolyl, indazolyl, carbazolyl, pyrrolopyrazinyl, imidazopyridinyl, thienopyridinyl, imidazopyrazinyl, pytazolopyridinyl, pyrazolothienyl, pyrazolotriazinyl, pyridopyridinyl, thienopyridyl and the like; and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially saturated, and the like.

Preferable examples of the non-aromatic heterocyclic group include
monocyclic non-aromatic heterocyclic groups such as azetidinyl, pyrrolidinyl, piperidinyl, morpholinyl, thiomorpholinyl, piperazinyl, hexamethyleniminyl, oxazolidinyl, thiazolidinyl, imidazolidinyl, oxazolinyl, thiazolinyl, imidazolinyl, dioxolyl, dioxolanyl, dihydrooxadiazolyl, pyranyl, tetrahydropyranyl, thiopyranyl, tetrahydrothiopyranyl, tetrahydrofuryl, pyrazolidinyl, pyrazolinyl, tetrahydropyrimidinyl, dihydrotriazolyl, tetrahydrotriazolyl and the like;
fused non-aromatic heterocyclic groups such as dihydroindolyl, dihydroisoindolyl, dihydrobenzofuranyl, dihydrobenzodioxinyl, dihydrobenzodioxepinyl, tetrahydrobenzofuranyl, chromenyl, dihydrochromenyl, dihydroquinolinyl, tetrahydroquinolinyl, dihydroisoquinolinyl, tetrahydroisoquinolinyl, dihydrophthalazinyl and the like;
and the like.

Each symbol in formulas (I), (II) and (I') is explained below.

A in the formula (I) and (I') is an optionally substituted cyclic group or an optionally substituted chain hydrocarbon group.

Examples of the "chain hydrocarbon group" of the "optionally substituted chain hydrocarbon group" represented by A include a "$C_{1-10}$ alkyl group", a "$C_{2-10}$ alkenyl group" and a "$C_{2-10}$ alkynyl group".

Examples of the "cyclic group" of the "optionally substituted cyclic group" represented by A include a $C_{3-8}$ cycloalkyl group, a $C_{3-8}$ cycloalkenyl group, a $C_{4-8}$ cycloalkadienyl group, a $C_{6-14}$ aryl group, a heterocyclic group and the like.

Examples of the substituent of the "optionally substituted chain hydrocarbon group" and "optionally substituted cyclic group" represented by A include
a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{4-8}$ cycloalkadienyl group, a $C_{6-14}$ aryl group, a $C_{7-13}$ aralkyl group, a $C_{6-14}$ aryl-$C_{2-6}$ alkenyl group, a heterocyclic group;
a hydroxy group, a $C_{1-6}$ alkoxy group, a $C_{2-6}$ alkenyloxy group, a $C_{2-6}$ alkynyloxy group, a $C_{3-8}$ cycloalkyloxy group, a $C_{3-8}$ cycloalkenyloxy group, a $C_{4-8}$ cycloalkadienyloxy group, a $C_{6-14}$ aryloxy group, a $C_{7-13}$ aralkyloxy group, a heterocyclyloxy group;
a formyl group, a $C_{1-6}$ alkyl-carbonyl group, a $C_{2-6}$ alkenyl-carbonyl group, a $C_{2-6}$ alkynyl-carbonyl group, a $C_{3-8}$ cycloalkyl-carbonyl group, a $C_{3-8}$ cycloalkenyl-carbonyl group, a $C_{4-8}$ cycloalkadienyl-carbonyl group, a $C_{6-14}$ aryl-carbonyl group, a $C_{7-13}$ aralkyl-carbonyl group, a heterocyclylcarbonyl group;
a carboxy group, a $C_{1-6}$ alkoxy-carbonyl group, a $C_{2-6}$ alkenyloxy-carbonyl group, a $C_{2-6}$ alkynyloxy-carbonyl group, a $C_{3-8}$ cycloalkyloxy-carbonyl group, a $C_{3-8}$ cycloalkenyloxy-carbonyl group, a $C_{4-8}$ cycloalkadienyloxy-carbonyl group, a $C_{6-14}$ aryloxycarbonyl group, a $C_{7-13}$ aralkyloxy-carbonyl group, a heterocyclyloxycarbonyl group;
a $C_{1-6}$ alkyl-carbonyloxy group, a $C_{2-6}$ alkenyl-carbonyloxy group, a $C_{2-6}$ alkynyl-carbonyloxy group, a $C_{3-8}$ cycloalkyl-carbonyloxy group, a $C_{3-8}$ cycloalkenyl-carbonyloxy group, a $C_{4-8}$ cycloalkadienyl-carbonyloxy group, a $C_{6-14}$ aryl-carbonyloxy group, a $C_{7-13}$ aralkyl-carbonyloxy group, a heterocyclylcarbonyloxy group;
a sulfanyl group, a $C_{1-6}$ alkylsulfanyl group, a $C_{2-6}$ alkenylsulfanyl group, a $C_{2-6}$ alkynylsulfanyl group, a $C_{3-8}$ cycloalkylsulfanyl group, a $C_{3-8}$ cycloalkenylsulfanyl group, a $C_{4-8}$ cycloalkadienylsulfanyl group, a $C_{6-14}$ arylsulfanyl group, a $C_{7-13}$ aralkylsulfanyl group, a heterocyclylsulfanyl group;
a sulfinyl group, a $C_{1-6}$ alkylsulfinyl group, a $C_{2-6}$ alkenylsulfinyl group, a $C_{2-6}$ alkynylsulfinyl group, a $C_{3-8}$ cycloalkylsulfinyl group, a $C_{3-8}$ cycloalkenylsulfinyl group, a $C_{4-8}$ cycloalkadienylsulfinyl group, a $C_{6-14}$ arylsulfinyl group, a $C_{7-13}$ aralkylsulfinyl group, a heterocyclylsulfinyl group;
a sulfonyl group (a sulfo group), $C_{1-6}$ alkylsulfonyl group, a $C_{2-6}$ alkenylsulfonyl group, a $C_{2-6}$ alkynylsulfonyl group, a $C_{3-8}$ cycloalkylsulfonyl group, a $C_{3-8}$ cycloalkenylsulfonyl group, a $C_{4-8}$ cycloalkadienylsulfonyl group, a $C_{6-14}$ arylsulfonyl group, a $C_{7-13}$ aralkylsulfonyl group, a heterocyclylsulfonyl group;
a $C_{1-6}$ alkylsulfonyloxy group, a $C_{2-6}$ alkenylsulfonyloxy group, a $C_{2-6}$ alkynylsulfonyloxy group, a $C_{3-8}$ cycloalkylsulfonyloxy group, a $C_{3-8}$ cycloalkenylsulfonyloxy group, a $C_{4-8}$ cycloalkadienylsulfonyloxy group, a $C_{6-14}$ arylsulfonyloxy group, a $C_{7-13}$ aralkylsulfonyloxy group, a heterocyclylsulfonyloxy group;
an amino group, a mono or di-$C_{1-6}$ alkylamino group, a mono or di-$C_{2-6}$ alkenylamino group, a mono or di-$C_{2-6}$ alkynylamino group, a mono or di-$C_{3-8}$ cycloalkylamino group, a mono or di-$C_{3-8}$ cycloalkenylamino group, a mono or di-$C_{4-8}$ cycloalkadienylamino group, a mono or di-$C_{6-14}$ arylamino group, a mono or di-$C_{7-13}$ aralkylamino group, a mono or di-heterocyclylamino group;
a carbamoyl group, a mono or di-$C_{1-6}$ alkylcarbamoyl group, a mono or di-$C_{2-6}$ alkenylcarbamoyl group, a mono or di-$C_{2-6}$ alkynylcarbamoyl group, a mono or di-$C_{3-8}$ cycloalkylcarbamoyl group, a mono or di-$C_{3-8}$ cycloalkenylcarbamoyl group, a mono or di-$C_{4-8}$ cycloalkadienylcarbamoyl group, a mono or di-$C_{6-14}$ arylcarbamoyl group, a mono or di-$C_{7-13}$ aralkylcarbamoyl group, a mono or di-heterocyclylcarbamoyl group;
a thiocarbamoyl group, a mono or di-$C_{1-6}$ alkylthiocarbamoyl group, a mono or di-$C_{2-6}$ alkenylthiocarbamoyl group, a mono or di-$C_{2-6}$ alkynylthiocarbamoyl group, a mono or di-$C_{3-8}$ cycloalkylthiocarbamoyl group, a mono or di-$C_{3-8}$ cycloalkenylthiocarbamoyl group, a mono or di-$C_{4-8}$ cycloalkadienylthiocarbamoyl group, a mono or di-$C_{6-14}$ arylthiocarbamoyl group, a mono or di-$C_{7-13}$ aralkylthiocarbamoyl group, a mono or di-heterocyclylthiocarbamoyl group;
a halogen atom;
a cyano group;
a nitro group;
an oxo group;
a thioxo group;
and the like. While the number of the substituents is not limited as long as it is a substitutable number, it is preferably 1 to 5, more preferably 1 to 3. When the number of the substituents is not less than 2, the respective substituents may be the same or different.

The above-mentioned substituent is optionally further substituted by the above-mentioned substituent(s). While the number of the substituents is not limited as long as it is a substitutable number, it is preferably 1 to 5, more preferably 1 to 3. When the number of the substituents is not less than 2, the respective substituents may be the same or different. Moreover, the substituent is optionally further substituted by a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{4-8}$ cycloalkadienyl group, a $C_{6-14}$ aryl group, a $C_{7-13}$ aralkyl group, a heterocyclic group, a halogen atom, a hydroxy group, a carboxy group, an amino group, a carbamoyl group, an cyano group, a nitro group, an oxo group and the like. While the number of the substituents is not limited as long as it is a substitutable number, it is preferably 1 to 5, more preferably 1 to 3. When the number of the substituents is not less than 2, the respective substituents may be the same or different.

A is preferably an optionally substituted $C_{6-14}$ aryl group, an optionally substituted heterocyclic group, an optionally substituted $C_{1-10}$ alkyl group or an optionally substituted $C_{2-10}$ alkenyl group.

Preferable specific examples of A include
(1) a $C_{6-10}$ aryl group (e.g., phenyl, naphthyl), fluorenyl or a heterocyclic group (e.g., thienyl, furyl, pyridyl, carbazolyl), each of which is optionally substituted by the substituent(s) selected from
  (i) a halogen atom (e.g., a chlorine atom, a bromine atom),
  (ii) a nitro group,
  (iii) a carboxy group,
  (iv) a $C_{1-6}$ alkyl group (e.g., methyl, ethyl, butyl),
  (v) a $C_{1-6}$ alkoxy group (e.g., methoxy, ethoxy, butoxy, tert-butoxy) optionally substituted by the substituent(s) selected from
    (a) a $C_{6-10}$ aryloxy group (e.g., phenoxy) optionally substituted by the substituent(s) selected from a halogen atom (e.g., a fluorine atom), a $C_{1-6}$ alkyl group (e.g., methyl) and a nitro group,
    (b) an amino group optionally mono- or di-substituted by $C_{1-6}$ alkoxy-carbonyl group(s) (e.g., tert-butoxycarbonyl),
    (c) a carboxy group,
    (d) a $C_{1-6}$ alkoxy-carbonyl group (e.g., tert-butoxycarbonyl),
    (e) a carbamoyl group optionally mono- or di-substituted by $C_{7-13}$ aralkyl group(s) (e.g., benzyl), and
    (f) a heterocyclic group (e.g., benzodioxanyl),
  (vi) a $C_{6-10}$ aryl group (e.g., phenyl) optionally substituted by nitro group(s),
  (vii) a $C_{6-10}$ aryloxy group (e.g., phenoxy) optionally substituted by the substituent(s) selected from a halogen atom (e.g., a fluorine atom, a chlorine atom, a bromine atom), a nitro group, a $C_{1-6}$ alkyl group (e.g., methyl), a $C_{1-6}$ alkoxy group (e.g., methoxy) and a cyano group,
  (viii) a $C_{7-13}$ aralkyl group (e.g., benzyl),
  (ix) a $C_{7-13}$ aralkyloxy group (e.g., benzyloxy, 3-phenyl-propoxy),
  (x) a $C_{6-10}$ aryl-$C_{2-6}$ alkenyl group (e.g., styryl),
  (xi) a heterocyclic group (e.g., pyridyl, tetrazolyl, thienyl, morpholinyl),
  (xii) a heterocyclyloxy group (e.g., pyridyloxy),
  (xiii) a heterocyclylcarbonyl group (e.g., morpholinyl carbonyl), and
  (xiv) an amino group optionally mono- or di-substituted by $C_{6-10}$ aryl group(s) (e.g., phenyl),
(2) a $C_{1-10}$ alkyl group (e.g., heptyl), or
(3) a $C_{2-10}$ alkenyl group (e.g., 1-hepten-1-yl).

A is more preferably an optionally substituted $C_{6-14}$ aryl group.

More preferable specific examples of A include a $C_{6-10}$ aryl group (e.g., phenyl, naphthyl) optionally substituted by the substituent(s) selected from
  (i) a halogen atom (e.g., a chlorine atom, a bromine atom),
  (ii) a nitro group,
  (iii) a $C_{1-6}$ alkyl group (e.g., butyl),
  (iv) a $C_{1-6}$ alkoxy group (e.g., methoxy, ethoxy, tert-butoxy) optionally substituted by the substituent(s) selected from
    (a) a $C_{6-10}$ aryloxy group (e.g., phenoxy) optionally substituted by the substituent(s) selected from a halogen atom (e.g., a fluorine atom), a $C_{1-6}$ alkyl group (e.g., methyl) and a nitro group,
    (b) an amino group optionally mono- or di-substituted by $C_{1-6}$ alkoxy-carbonyl group(s) (e.g., tert-butoxycarbonyl),
    (c) a carboxy group,
    (d) a $C_{1-6}$ alkoxy-carbonyl group (e.g., tert-butoxycarbonyl),
    (e) a carbamoyl group optionally mono- or di-substituted by $C_{7-13}$ aralkyl group(s) (e.g., benzyl), and
    (f) a heterocyclic group (e.g., benzodioxanyl),
  (v) a $C_{6-10}$ aryl group (e.g., phenyl),
  (vi) a $C_{6-10}$ aryloxy group (e.g., phenoxy) optionally substituted by the substituent(s) selected from a halogen atom (e.g., a chlorine atom, a bromine atom), a nitro group and a $C_{1-6}$ alkyl group (e.g., methyl),
  (vii) a $C_{7-13}$ aralkyloxy group (e.g., benzyloxy),
  (viii) a heterocyclic group (e.g., morpholinyl), and
  (ix) a heterocyclyloxy group (e.g., pyridyloxy).

A is still more preferably an optionally substituted phenyl group.

Still more preferable specific examples of A include a phenyl group optionally substituted by the substituent(s) selected from
  (i) a halogen atom (e.g., a chlorine atom, a bromine atom),
  (ii) a nitro group,
  (iii) a $C_{1-6}$ alkoxy group (e.g., methoxy, ethoxy, tert-butoxy) optionally substituted by the substituent(s) selected from
    (a) a $C_{6-10}$ aryloxy group (e.g., phenoxy) optionally substituted by the substituent(s) selected from a nitro group and a $C_{1-6}$ alkyl group (e.g., methyl),
    (b) an amino group optionally mono- or di-substituted by $C_{1-6}$ alkoxy-carbonyl group(s) (e.g., tert-butoxycarbonyl),
    (c) a carboxy group, and
    (d) a $C_{1-6}$ alkoxy-carbonyl group (e.g., tert-butoxycarbonyl),
  (iv) a $C_{6-10}$ aryl group (e.g., phenyl),
  (v) a $C_{6-10}$ aryloxy group (e.g., phenoxy) optionally substituted by halogen atom(s) (e.g., a bromine atom),
  (vi) a $C_{7-13}$ aralkyloxy group (e.g., benzyloxy), and
  (vii) a heterocyclyloxy group (e.g., pyridyloxy).

Particularly preferable specific examples of A include a phenyl group optionally substituted by the substituent(s) selected from
  (i) a halogen atom (e.g., a bromine atom),
  (ii) a nitro group,
  (iii) a $C_{1-6}$ alkoxy group (e.g., methoxy, ethoxy) optionally substituted by $C_{6-10}$ aryloxy group(s) (e.g., phenoxy) optionally substituted by the substituent(s) selected from a nitro group and a $C_{1-6}$ alkyl group (e.g., methyl),
  (v) a $C_{6-10}$ aryloxy group (e.g., phenoxy), and
  (vi) a $C_{7-13}$ aralkyloxy group (e.g., benzyloxy).

As another preferable embodiment of A, examples thereof include a group represented by

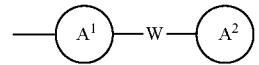

wherein ring $A^1$ and ring $A^2$ are each independently an optionally substituted benzene ring, and W is an oxygen atom, a sulfur atom, or a group represented by the formula: —$V^1$—

(CH$_2$)m-V$^2$— wherein V$^1$ and V$^2$ are each independently a bond, an oxygen atom or a sulfur atom, and m is an integer of 1 to 3, in the formula (II).

Ring A$^1$ and ring A$^2$ are each independently an optionally substituted benzene ring.

Examples of the substituent of the "optionally substituted benzene ring" represented by ring A$^1$ and ring A$^2$ include those similar to the substituent of the "optionally substituted cyclic group" represented by A.

Ring A$^1$ is preferably a benzene ring optionally substituted by the substituent(s) selected from
- (1) a halogen atom (e.g., a chlorine atom, a bromine atom)
- (2) a C$_{1-6}$ alkyl group (e.g., methyl), and
- (3) a C$_{1-6}$ alkoxy group (e.g., methoxy).

Ring A$^1$ is more preferably a benzene ring optionally substituted by halogen atom(s) (e.g., a chlorine atom).

Ring A$^1$ is particularly preferably an unsubstituted benzene ring.

Ring A$^2$ is preferably a benzene ring optionally substituted by the substituent(s) selected from
- (1) a halogen atom (e.g., a fluorine atom, a chlorine atom, a bromine atom)
- (2) a nitro group,
- (3) a cyano group,
- (4) a C$_{1-6}$ alkyl group (e.g., methyl), and
- (5) a C$_{1-6}$ alkoxy group (e.g., methoxy).

Ring A$^2$ is more preferably a benzene ring optionally substituted by the substituent(s) selected from
- (1) a halogen atom (e.g., a fluorine atom, a chlorine atom, a bromine atom)
- (2) a nitro group, and
- (3) a C$_{1-6}$ alkyl group (e.g., methyl).

Ring A$^2$ is still more preferably a benzene ring optionally substituted by the substituent(s) selected from
- (1) a nitro group, and
- (2) a C$_{1-6}$ alkyl group (e.g., methyl).

W is an oxygen atom, a sulfur atom, or a group represented by the formula: —V$^1$—(CH$_2$)m-V$^2$— wherein V$^1$ and V$^2$ are each independently a bond, an oxygen atom or a sulfur atom, and m is an integer of 1 to 3.

Specific examples of W include an oxygen atom, a sulfur atom, —OCH$_2$O—, —OCH$_2$CH$_2$O—, —OCH$_2$CH$_2$CH$_2$O—, —CH$_2$O—, —CH$_2$CH$_2$O—, —CH$_2$CH$_2$CH$_2$O—, —OCH$_2$—, —OCH$_2$CH$_2$—, —OCH$_2$CH$_2$CH$_2$—, —SCH$_2$S—, —SCH$_2$CH$_2$S—, —SCH$_2$CH$_2$CH$_2$S—, —CH$_2$S—, —CH$_2$CH$_2$S—, —CH$_2$CH$_2$CH$_2$S—, —SCH$_2$—, —SCH$_2$CH$_2$—, —SCH$_2$CH$_2$CH$_2$—, —CH$_2$—, —CH$_2$CH$_2$—, —CH$_2$CH$_2$CH$_2$— and the like.

W is preferably an oxygen atom, a sulfur atom, or a group represented by the formula: —V$^1$—(CH$_2$)m-V$^2$— wherein V$^1$ and V$^2$ are each independently a bond or an oxygen atom, and m is an integer of 1 to 3.

W is more preferably an oxygen atom, —OCH$_2$CH$_2$O—, —OCH$_2$CH$_2$CH$_2$O— or —OCH$_2$—.

W is still more preferably an oxygen atom, —OCH$_2$CH$_2$O— or —OCH$_2$—.

W is particularly preferably an oxygen atom or —OCH$_2$CH$_2$O—.

B in the formula (I') is a hydrogen atom, an optionally substituted cyclic group, an optionally substituted amino group, an optionally substituted hydroxy group or an optionally esterified or amidated carboxy group.

B$^2$ in the formula (II) is an optionally substituted cyclic group or an optionally substituted amino group.

Examples of the "optionally substituted cyclic group" represented by B or B$^2$ include those similar to the "optionally substituted cyclic group" represented by A.

Examples of the "optionally substituted amino group" represented by B or B$^2$ include an amino group, a mono or di-C$_{1-6}$ alkylamino group, a mono or di-C$_{2-6}$ alkenylamino group, a mono or di-C$_{2-6}$ alkynylamino group, a mono or di-C$_{3-8}$ cycloalkylamino group, a mono or di-C$_{3-8}$ cycloalkenylamino group, a mono or di-C$_{4-8}$ cycloalkadienylamino group, a mono or di-C$_{6-14}$ acylamino group, a mono or di-C$_{7-13}$ aralkylamino group, a mono or di-heterocyclylamino group and the like. They optionally have substituent(s), and examples of the substituent include those similar to the substituent of the "optionally substituted cyclic group" represented by A. The "optionally substituted amino group" is preferably an amino group.

Examples of the "optionally substituted hydroxy group" represented by B include a hydroxy group, a C$_{1-6}$ alkoxy group, a C$_{2-6}$ alkenyloxy group, a C$_{2-6}$ alkynyloxy group, a C$_{3-8}$ cycloalkyloxy group, a C$_{3-8}$ cycloalkenyloxy group, a C$_{4-8}$ cycloalkadienyloxy group, a C$_{6-14}$ aryloxy group, a C$_{7-13}$ aralkyloxy group, a heterocyclyloxy group and the like. They optionally have substituent(s), and examples of the substituent include those similar to the substituent of the "optionally substituted cyclic group" represented by A. The "optionally substituted hydroxy group" is preferably a hydroxy group or a C$_{1-6}$ alkoxy group.

Examples of the "optionally esterified or amidated carboxy group" represented by B include a carboxy group, a C$_{1-6}$ alkoxy-carbonyl group, a C$_{2-6}$ alkenyloxy-carbonyl group, a C$_{2-6}$ alkynyloxy-carbonyl group, a C$_{3-8}$ cycloalkyloxy-carbonyl group, a C$_{3-8}$ cycloalkenyloxy-carbonyl group, a C$_{4-8}$ cycloalkadienyloxy-carbonyl group, a C$_{6-14}$ aryloxycarbonyl group, a C$_{7-13}$ aralkyloxy-carbonyl group, a heterocyclyloxycarbonyl group;

a carbamoyl group, a mono or di-C$_{1-6}$ alkylcarbamoyl group, a mono or di-C$_{2-6}$ alkenylcarbamoyl group, a mono or di-C$_{2-6}$ alkynylcarbamoyl group, a mono or di-C$_{3-8}$ cycloalkylcarbamoyl group, a mono or di-C$_{3-8}$ cycloalkenylcarbamoyl group, a mono or di-C$_{4-8}$ cycloalkadienylcarbamoyl group, a mono or di-C$_{6-14}$ arylcarbamoyl group, a mono or di-C$_{7-13}$ aralkylcarbamoyl group, a mono or di-heterocyclylcarbamoyl group;

and the like. They optionally have substituent(s), and examples of the substituent include those similar to the substituent of the "optionally substituted cyclic group" represented by A. The "optionally esterified or amidated carboxy group" is preferably a carboxy group or a C$_{1-6}$ alkoxy-carbonyl group.

B$^2$ is preferably an optionally substituted 5- or 6-membered cyclic group (a phenyl group, a C$_{5-6}$ cycloalkyl group, a 5- or 6-membered heterocyclic group optionally fused with a benzene ring) or an amino group (in this case, Z is preferably a bond or —(CH$_2$)n$^1$-NHCO—(CH$_2$)n$^2$- wherein n$^1$ and n$^2$ are each independently an integer of 0 to 2).

Preferable specific examples of B$^2$ include
(1) a phenyl group, a C$_{5-6}$ cycloalkyl group (e.g., cyclohexyl), or a 5- or 6-membered heterocyclic group optionally fused with a benzene ring (e.g., tetrahydrofuryl, pyrrolidinyl, piperidyl, piperazinyl, pyridyl, morpholinyl, thiomorpholinyl, 1,1-dioxidothiomorpholinyl, 1,1-dioxido-1,2-benzisothiazolyl, indolyl, tetrahydroisoquinolyl, benzodioxolyl, 2,2-dioxido-1,2,3-oxathiazine), each of which is optionally substituted by substituent(s) selected from
(i) a nitro group,
(ii) a hydroxy group, (iii) a carboxy group,
(iv) a sulfamoyl group,
(v) a sulfo group or a sulfonato group,
(vi) a $C_{1-6}$ alkyl group,
(vii) a $C_{7-13}$ aralkyl group,
(viii) a $C_{1-6}$ alkoxy group,
(ix) a $C_{1-6}$ alkyl-carbonyl group optionally substituted by $C_{1-6}$ alkoxy group(s),
(x) a $C_{1-6}$ alkoxy-carbonyl group,
(xi) a $C_{1-6}$ alkylsulfanyl group, and
(xii) a $C_{1-6}$ alkylsulfonyl group, or
(2) an amino group (in this case, Z is preferably a bond or —$(CH_2)n^1$-NHCO—$(CH_2)n^2$- wherein $n^1$ and $n^2$ are each independently an integer of 0 to 2.

More preferable specific examples of $B^2$ include
(1) a phenyl group, a $C_{5-6}$ cycloalkyl group (e.g., cyclohexyl), or a 5- or 6-membered heterocyclic group optionally fused with a benzene ring (e.g., tetrahydrofuryl, pyrrolidinyl, piperidyl, pyridyl, morpholinyl, 1,1-dioxidothiomorpholinyl, 1,1-dioxido-1,2-benzisothiazolyl), each of which is optionally substituted by substituent(s) selected from
(i) a hydroxy group,
(ii) a sulfamoyl group,
(iii) a sulfo group or a sulfonato group,
(iv) a $C_{1-6}$ alkyl-carbonyl group optionally substituted by $C_{1-6}$ alkoxy group(s),
(v) a $C_{1-6}$ alkoxy-carbonyl group, and
(vi) a $C_{1-6}$ alkylsulfonyl group, or
(2) an amino group (in this case, Z is preferably a bond or —$(CH_2)n^1$-NHCO—$(CH_2)n^2$- wherein $n^1$ and $n^2$ are each independently an integer of 0 to 2.

$B^2$ is more preferably an optionally substituted phenyl group or an optionally substituted 5- or 6-membered nitrogen-containing heterocyclic group (optionally fused with a benzene ring).

Still more preferable specific examples of $B^2$ include a phenyl group or a 5- or 6-membered nitrogen-containing heterocyclic group (e.g., pyrrolidinyl, piperidyl, pyridyl, 1,1-dioxidothiomorpholinyl, 1,1-dioxido-1,2-benzisothiazolyl), each of which is optionally substituted by substituent(s) selected from
(i) a $C_{1-6}$ alkoxy-carbonyl group,
(ii) a sulfamoyl group, and
(iii) a $C_{1-6}$ alkylsulfonyl group.

Particularly preferable specific examples of $B^2$ include a phenyl group or a 5- or 6-membered nitrogen-containing heterocyclic group (e.g., piperidyl, 1,1-dioxidothiomorpholinyl, 1,1-dioxido-1,2-benzisothiazolyl), each of which is optionally substituted by substituent(s) selected from
(i) a sulfamoyl group, and
(ii) a $C_{1-6}$ alkylsulfonyl group.

As another preferable embodiment of $B^2$, examples thereof include a group represented by $B^1$:

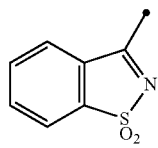

wherein • means a bonding site, (i.e., a 1,1-dioxido-1,2-benzisothiazol-3-yl group) which is optionally substituted. Examples of the substituent include those similar to the substituent of the "optionally substituted cyclic group" represented by A.

$B^2$ is preferably a group represented by

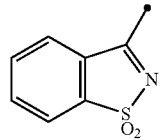

wherein • means a bonding site, i.e., a 1,1-dioxido-1,2-benzisothiazol-3-yl group.

B is preferably a hydrogen atom, an optionally substituted 5- or 6-membered cyclic group (a phenyl group, a $C_{5-6}$ cycloalkyl group, a 5- or 6-membered heterocyclic group optionally fused with a benzene ring), an amino group, a hydroxy group, a $C_{1-6}$ alkoxy group, a carboxy group or a $C_{1-6}$ alkoxy-carbonyl group.

Preferable examples of B include the above-mentioned preferable examples of $B^2$, as well as a hydrogen atom, a hydroxy group, a $C_{1-6}$ alkoxy group, a carboxy group and a $C_{1-6}$ alkoxy-carbonyl group.

$X^1$ and $X^2$ are each independently an oxygen atom or a sulfur atom.

$X^1$ is preferably a sulfur atom.

$X^2$ is preferably an oxygen atom.

Y and Z are each independently a bond or a spacer having 1 to 6 atoms.

Examples of the "spacer having 1 to 6 atoms" represented by Y or Z include a group represented by —$(CH_2)n^1$-$V^3$—$(CH_2)n^2$- wherein $V^3$ is a bond, an oxygen atom, a sulfur atom, —$N(R^2)$— (wherein $R^2$ is a hydrogen atom or a $C_{1-6}$ alkyl group), —CH=CH—, —CH=C($C_{1-6}$ alkyl)-, —CO—, —OCO—, —$CO_2$—, —NHCO—, —CONH—, —OCONH—, —$NHCO_2$—, —NHCONH—, —CONHCO—, —$SO_2$—, —$NHSO_2$—, —$SO_2NH$—, —$CONHSO_2$—, —$SO_2NHCO$— or the like, and $n^1$ and $n^2$ are each independently an integer of 0 to 6, and $n^1+n^2$ is an integer of 0 to 6.

Specific examples of the "spacer having 1 to 6 atoms" include
—$CH_2$—, —$CH_2CH_2$—, —$CH_2CH_2CH_2$—, —$CH_2CH_2CH_2CH_2$—, —CH=CH—, —CH=C($C_{1-6}$ alkyl)-;
—O—, —S—, —NH—, —N($CH_3$)—, —CO—, —OCO—, —$CO_2$—, —NHCO—, —CONH—, —OCONH—, —$NHCO_2$—, —NHCONH—, —CONHCO—, —$SO_2$—, —$NHSO_2$—, —$SO_2NH$—, —CO—$NHSO_2$—, —$SO_2NHCO$—;
—$CH_2O$—, —$CH_2S$—, —$CH_2NH$—, —$CH_2N(CH_3)$—, —$CH_2CO$—, —$CH_2OCO$—, —$CH_2CO_2$—, —$CH_2NHCO$—, —$CH_2CONH$—, —$CH_2OCONH$—, —$CH_2NHCO_2$—, —$CH_2NHCONH$—, —$CH_2CONHCO$—, —$CH_2SO_2$—, —$CH_2NHSO_2$—, —$CH_2SO_2NH$—;
—$OCH_2$—, —$SCH_2$—, —$NHCH_2$—, —$N(CH_3)$ a $CH_2$—, —$COCH_2$—, —$OCOCH_2$—, —$CO_2CH_2$—, —$NHCOCH_2$—, —$CONHCH_2$—, —$OCONHCH_2$—, —$NHCO_2CH_2$—, —$NHCONHCH_2$—, —$CONHCOCH_2$—, —$SO_2CH_2$—, —$NHSO_2CH_2$—, —$SO_2NHCH_2$—;
—$CH_2OCH_2$—, —$CH_2SCH_2$—, —$CH_2NHCH_2$—, —$CH_2N(CH_3)$ a $CH_2$—, —$CH_2COCH_2$—, —$CH_2OCOCH_2$—, —$CH_2CO_2CH_2$—, —$CH_2NHCOCH_2$—, —$CH_2CONHCH_2$—, —$CH_2OCONHCH_2$—, —$CH_2NHCO_2CH_2$—, —CH₂NHCONHCH₂—, —CH₂CONHCOCH₂—,
—CH₂SO₂CH₂—, —CH₂NHSO₂CH₂—,
—CH₂SO₂NHCH₂—;
—CH₂CH₂OCH₂—, —CH₂CH₂SCH₂—,
—CH₂CH₂NHCH₂—, —CH₂CH₂N(CH₃) a CH₂—,
—CH₂CH₂COCH₂—, —CH₂CH₂OCOCH₂—,
—CH₂CH₂CO₂CH₂—, —CH₂CH₂NHCOCH₂—,
—CH₂CH₂CONHCH₂—, —CH₂CH₂OCONHCH₂—,
—CH₂CH₂NHCO₂CH₂—, —CH₂CH₂NHCONHCH₂—,
—CH₂CH₂CONHCOCH₂—, —CH₂CH₂SO₂CH₂—,
—CH₂CH₂NHSO₂CH₂—, —CH₂CH₂SO₂NHCH₂—;
—CH₂CH₂OCH₂CH₂—, —CH₂CH₂SCH₂CH₂—,
—CH₂CH₂NHCH₂CH₂—, —CH₂CH₂N(CH₃) a CH₂CH₂—, —CH₂CH₂COCH₂CH₂—,
—CH₂CH₂OCOCH₂CH₂—, —CH₂CH₂CO₂CH₂CH₂—,
—CH₂CH₂NHCOCH₂CH₂—,
—CH₂CH₂CONHCH₂CH₂—,
—CH₂CH₂SO₂CH₂CH₂—,
—CH₂CH₂NHSO₂CH₂CH₂—,
—CH₂CH₂SO₂NHCH₂CH₂—;
and the like.

Y is preferably a bond or a spacer having 1 or 2 atoms (preferably —CH₂—, —CH₂CH₂—, —CH=CH—, —CH=C(C₁₋₆ alkyl)-).

Y is more preferably a bond or —CH=CH—.

Y is particularly preferably a bond.

In the formula (I), Z is preferably a bond or a spacer having 1 or 2 atoms.

Z is more preferably —N(R¹)— wherein R¹ is a hydrogen atom or a C₁₋₆ alkyl group.

Z is particularly preferably —NH—.

In the formula (II), Z is preferably a bond, or a group represented by —(CH₂)n¹-V³—(CH₂)n²- wherein V³ is a bond, —CO—, —NH—, —NHCO—, —CONH—, —SO₂NH— or —SO₂NHCO—, and n¹ and n² are each independently an integer of 0 to 2.

Z is more preferably a bond, or a group represented by —(CH₂)n¹-V³—(CH₂)n²- wherein V³ is a bond, —CO—, —NH—, —NHCO— or —CONH—, and n¹ and n² are each independently an integer of 0 to 2.

Z is still more preferably a bond, —NH—, —CONH—, —COCH₂—, —CH₂— or —(CH₂)₂—.

Z is particularly preferably —NH—, —CONH—, —CH₂— or —(CH₂)₂—.

In the formula (I'), Z is preferably a bond, or a group represented by —(CH₂)n¹-V³—(CH₂)n²- wherein V³ is a bond, —CO—, —NH—, —NHCO—, —CONH—, —SO₂—, —SO₂NH— or —SO₂NHCO—, and n¹ and n² are each independently an integer of 0 to 2.

Z is more preferably a bond, or a group represented by —(CH₂)n¹-V³—(CH₂)n²- wherein V³ is a bond, —CO—, —NH—, —NHCO— or —CONH—, and n¹ and n² are each independently an integer of 0 to 2.

Z is still more preferably a bond, —NH—, —CONH—, —COCH₂—, —CH₂— or —(CH₂)₂—.

Z is particularly preferably —NH—, —CONH—, —CH₂— or —(CH₂)₂—.

The partial structure represented by

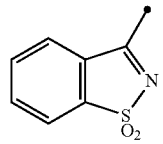

in the formulas (I), (II) and (I') is preferably a partial structure represented by

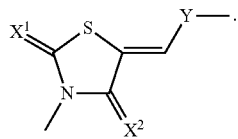

Among compound (I'), compound (I) and compound (II) are novel compounds.

Preferable compound (I) and compound (II) are as follows.

[Compound A'-I]

In the formula (I), compound (I) wherein
the partial structure represented by

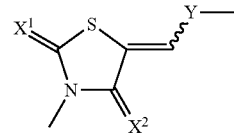

is a partial structure represented by

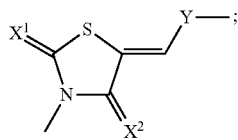

A is an optionally substituted $C_{6-14}$ aryl group, an optionally substituted heterocyclic group, an optionally substituted $C_{1-10}$ alkyl group or an optionally substituted $C_{2-10}$ alkenyl group;

B¹ is a group represented by

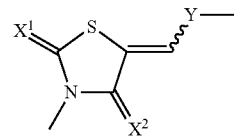

wherein • means a bonding site, which is an optionally substituted;
X¹ is a sulfur atom;
X² is an oxygen atom;
Y is a bond or a spacer having 1 or 2 atoms; and
Z is a bond or a spacer having 1 or 2 atoms.

[Compound B'-I]

In the formula (I), compound (I) wherein
the partial structure represented by is a partial structure represented by

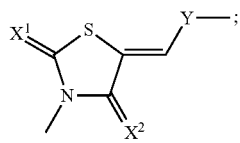

A is an optionally substituted C$_{6-14}$ aryl group;
B$^1$ is a group represented by

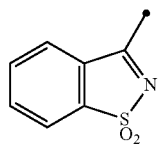

wherein • means a bonding site;
X$^1$ is a sulfur atom;
X$^2$ is an oxygen atom;
Y is a bond or a spacer having 1 or 2 atoms; and
Z is —N(R$^1$)— wherein R$^1$ is a hydrogen atom or a C$_{1-6}$ alkyl group.

[Compound C'-I]
In the formula (I), compound (I) wherein the partial structure represented by

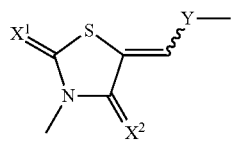

is a partial structure represented by

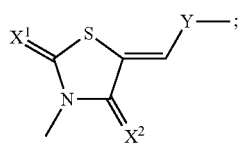

A is an optionally substituted phenyl group;
B$^1$ is a group represented by

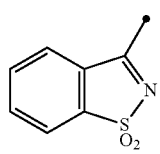

wherein • means a bonding site;
X$^1$ is a sulfur atom;
X$^2$ is an oxygen atom;
Y is a bond or a spacer having 1 or 2 atoms; and
Z is —NH—.

[Compound A-I]
In the formula (I), compound (I) wherein the partial structure represented by

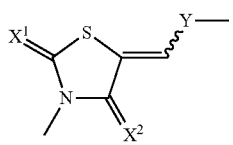

is a partial structure represented by

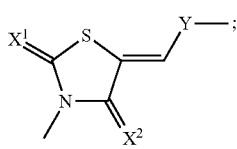

A is
(1) a C$_{6-10}$ aryl group (e.g., phenyl, naphthyl), fluorenyl or a heterocyclic group (e.g., thienyl, furyl, pyridyl, carbazolyl), each of which is optionally substituted by the substituent(s) selected from
(i) a halogen atom (e.g., a chlorine atom, a bromine atom),
(ii) a nitro group,
(iii) a carboxy group,
(iv) a C$_{1-6}$ alkyl group (e.g., methyl, ethyl, butyl),
(v) a C$_{1-6}$ alkoxy group (e.g., methoxy, ethoxy, butoxy, tert-butoxy) optionally substituted by C$_{6-10}$ aryloxy group(s) (e.g., phenoxy) optionally substituted by the substituent(s) selected from a halogen atom (e.g., a fluorine atom), a C$_{1-6}$ alkyl group (e.g., methyl) and a nitro group,
(vi) a C$_{6-10}$ aryl group (e.g., phenyl) optionally substituted by nitro group(s),
(vii) a C$_{6-10}$ aryloxy group (e.g., phenoxy) optionally substituted by the substituent(s) selected from a halogen atom (e.g., a fluorine atom, a chlorine atom, a bromine atom), a nitro group, a C$_{1-6}$ alkyl group (e.g., methyl), a C$_{1-6}$ alkoxy group (e.g., methoxy) and a cyano group,
(viii) a C$_{7-13}$ aralkyl group (e.g., benzyl),
(ix) a C$_{7-13}$ aralkyloxy group (e.g., benzyloxy, 3-phenylpropoxy),
(x) a C$_{6-10}$ aryl-C$_{2-6}$ alkenyl group (e.g., styryl),
(xi) a heterocyclic group (e.g., pyridyl, tetrazolyl, thienyl, morpholinyl),
(xii) a heterocyclyloxy group (e.g., pyridyloxy),
(xiii) a heterocyclylcarbonyl group (e.g., morpholinyl carbonyl), and
(xiv) an amino group optionally mono- or di-substituted by C$_{6-10}$ aryl group(s) (e.g., phenyl),
(2) a C$_{1-10}$ alkyl group (e.g., heptyl), or
(3) a C$_{2-10}$ alkenyl group (e.g., 1-hepten-1-yl);
B$^1$ is a group represented by

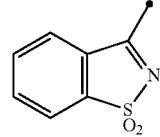

wherein • means a bonding site;

X¹ is a sulfur atom;
X² is an oxygen atom;
Y is a bond or a spacer having 1 or 2 atoms; and
Z is —NH—.

[Compound A-Ia]

In the formula (I), compound (I) wherein
the partial structure represented by

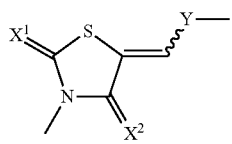

is a partial structure represented by

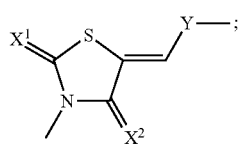

A is
(1) a $C_{6-10}$ aryl group (e.g., phenyl, naphthyl), fluorenyl or a heterocyclic group (e.g., thienyl, furyl, pyridyl, carbazolyl), each of which is optionally substituted by the substituent(s) selected from
  (i) a halogen atom (e.g., a chlorine atom, a bromine atom),
  (ii) a nitro group,
  (iii) a carboxy group,
  (iv) a $C_{1-6}$ alkyl group (e.g., methyl, ethyl, butyl),
  (v) a $C_{1-6}$ alkoxy group (e.g., methoxy, ethoxy, butoxy, tert-butoxy) optionally substituted by the substituent(s) selected from
    (a) a $C_{6-10}$ aryloxy group (e.g., phenoxy) optionally substituted by the substituent(s) selected from a halogen atom (e.g., a fluorine atom), a $C_{1-6}$ alkyl group (e.g., methyl) and a nitro group,
    (b) an amino group optionally mono- or di-substituted by $C_{1-6}$ alkoxy-carbonyl group(s) (e.g., tert-butoxy-carbonyl),
    (c) a carboxy group,
    (d) a $C_{1-6}$ alkoxy-carbonyl group (e.g., tert-butoxycarbonyl),
    (e) a carbamoyl group optionally mono- or di-substituted by $C_{7-13}$ aralkyl group(s) (e.g., benzyl), and
    (f) a heterocyclic group (e.g., benzodioxanyl),
  (vi) a $C_{6-10}$ aryl group (e.g., phenyl) optionally substituted by nitro group(s),
  (vii) a $C_{6-10}$ aryloxy group (e.g., phenoxy) optionally substituted by the substituent(s) selected from a halogen atom (e.g., a fluorine atom, a chlorine atom, a bromine atom), a nitro group, a $C_{1-6}$ alkyl group (e.g., methyl), a $C_{1-6}$ alkoxy group (e.g., methoxy) and a cyano group,
  (viii) a $C_{7-13}$ aralkyl group (e.g., benzyl),
  (ix) a $C_{7-13}$ aralkyloxy group (e.g., benzyloxy, 3-phenyl-propoxy),
  (x) a $C_{6-10}$ aryl-$C_{2-6}$ alkenyl group (e.g., styryl),
  (xi) a heterocyclic group (e.g., pyridyl, tetrazolyl, thienyl, morpholinyl),
  (xii) a heterocyclyloxy group (e.g., pyridyloxy),
  (xiii) a heterocyclylcarbonyl group (e.g., morpholinyl carbonyl), and
  (xiv) an amino group optionally mono- or di-substituted by $C_{6-10}$ aryl group(s) (e.g., phenyl),
(2) a $C_{1-10}$ alkyl group (e.g., heptyl), or
(3) a $C_{2-10}$ alkenyl group (e.g., 1-hepten-1-yl);

$B^1$ is a group represented by

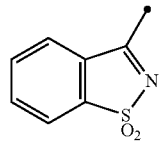

wherein • means a bonding site;
X¹ is a sulfur atom;
X² is an oxygen atom;
Y is a bond or a spacer having 1 or 2 atoms; and
Z is —NH—.

[Compound B-I]

In the formula (I), compound (I) wherein
the partial structure represented by

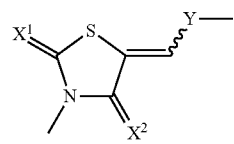

is a partial structure represented by

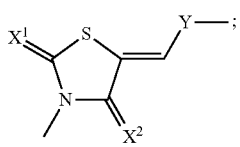

A is a $C_{6-10}$ aryl group (e.g., phenyl, naphthyl) optionally substituted by the substituent(s) selected from
  (i) a halogen atom (e.g., a chlorine atom, a bromine atom),
  (ii) a nitro group,
  (iii) a $C_{1-6}$ alkyl group (e.g., butyl),
  (iv) a $C_{1-6}$ alkoxy group (e.g., methoxy, ethoxy, tert-butoxy) optionally substituted by $C_{6-10}$ aryloxy group(s) (e.g., phenoxy) optionally substituted by the substituent(s) selected from a halogen atom (e.g., a fluorine atom), a $C_{1-6}$ alkyl group (e.g., methyl) and a nitro group,
  (v) a $C_{6-10}$ aryl group (e.g., phenyl),
  (vi) a $C_{6-10}$ aryloxy group (e.g., phenoxy) optionally substituted by the substituent(s) selected from a halogen atom (e.g., a chlorine atom, a bromine atom), a nitro group and a $C_{1-6}$ alkyl group (e.g., methyl),
  (vii) a $C_{7-13}$ aralkyloxy group (e.g., benzyloxy),
  (viii) a heterocyclic group (e.g., morpholinyl), and
  (ix) a heterocyclyloxy group (e.g., pyridyloxy);

B¹ is a group represented by

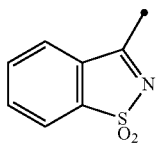

wherein • means a bonding site;
X¹ is a sulfur atom;
X² is an oxygen atom;
Y is a bond, —$CH_2$—, —$CH_2CH_2$—, —CH=CH— or —CH=C($C_{1-6}$ alkyl)-; and
Z is —NH—.

[Compound B-Ia]
In the formula (I), compound (I) wherein the partial structure represented by

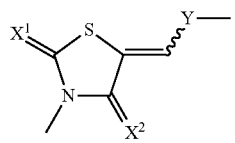

is a partial structure represented by

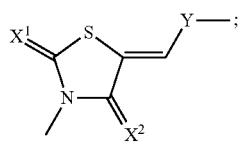

A is a $C_{6-10}$ aryl group (e.g., phenyl, naphthyl) optionally substituted by the substituent(s) selected from
(i) a halogen atom (e.g., a chlorine atom, a bromine atom),
(ii) a nitro group,
(iii) a $C_{1-6}$ alkyl group (e.g., butyl),
(iv) a $C_{1-6}$ alkoxy group (e.g., methoxy, ethoxy, tert-butoxy) optionally substituted by the substituent(s) selected from
(a) a $C_{6-10}$ aryloxy group (e.g., phenoxy) optionally substituted by the substituent(s) selected from a halogen atom (e.g., a fluorine atom), a $C_{1-6}$ alkyl group (e.g., methyl) and a nitro group,
(b) an amino group optionally mono- or di-substituted by $C_{1-6}$ alkoxy-carbonyl group(s) (e.g., tert-butoxycarbonyl),
(c) a carboxy group,
(d) a $C_{1-6}$ alkoxy-carbonyl group (e.g., tert-butoxycarbonyl),
(e) a carbamoyl group optionally mono- or di-substituted by $C_{7-13}$ aralkyl group(s) (e.g., benzyl), and
(f) a heterocyclic group (e.g., benzodioxanyl),
(v) a $C_{6-10}$ aryl group (e.g., phenyl),
(vi) a $C_{6-10}$ aryloxy group (e.g., phenoxy) optionally substituted by the substituent(s) selected from a halogen atom (e.g., a chlorine atom, a bromine atom), a nitro group and a $C_{1-6}$ alkyl group (e.g., methyl),
(vii) a $C_{7-13}$ aralkyloxy group (e.g., benzyloxy),
(viii) a heterocyclic group (e.g., morpholinyl), and
(ix) a heterocyclyloxy group (e.g., pyridyloxy);

B¹ is a group represented by

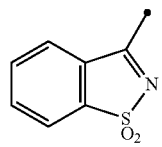

wherein • means a bonding site;
X¹ is a sulfur atom;
X² is an oxygen atom;
Y is a bond, —$CH_2$—, —$CH_2CH_2$—, —CH=CH— or —CH=C($C_{1-6}$ alkyl)-; and
Z is —NH—.

[Compound C-I]
In the formula (I), compound (I) wherein the partial structure represented by

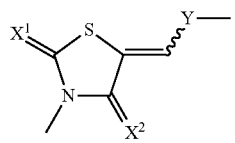

is a partial structure represented by

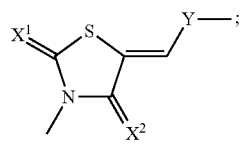

A is a phenyl group optionally substituted by the substituent(s) selected from
(i) a halogen atom (e.g., a chlorine atom, a bromine atom),
(ii) a nitro group,
(iii) a $C_{1-6}$ alkoxy group (e.g., methoxy, ethoxy, tert-butoxy) optionally substituted by $C_{6-10}$ aryloxy group(s) (e.g., phenoxy) optionally substituted by the substituent(s) selected from a nitro group and a $C_{1-6}$ alkyl group (e.g., methyl),
(iv) a $C_{6-10}$ aryl group (e.g., phenyl),
(v) a $C_{6-10}$ aryloxy group (e.g., phenoxy) optionally substituted by halogen atom(s) (e.g., a bromine atom),
(vi) a $C_{7-13}$ aralkyloxy group (e.g., benzyloxy), and
(vii) a heterocyclyloxy group (e.g., pyridyloxy);

B¹ is a group represented by

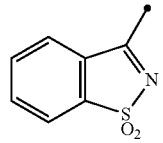

wherein • means a bonding site;
X¹ is a sulfur atom;
X² is an oxygen atom;
Y is a bond or —CH=CH—; and
Z is —NH—.

[Compound C-Ia]
In the formula (I), compound (I) wherein the partial structure represented by

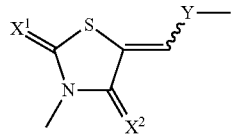

is a partial structure represented by

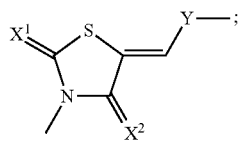

A is a phenyl group optionally substituted by the substituent(s) selected from
(i) a halogen atom (e.g., a chlorine atom, a bromine atom),
(ii) a nitro group,
(iii) a $C_{1-6}$ alkoxy group (e.g., methoxy, ethoxy, tert-butoxy) optionally substituted by the substituent(s) selected from
(a) a $C_{6-10}$ aryloxy group (e.g., phenoxy) optionally substituted by the substituent(s) selected from a nitro group and a $C_{1-6}$ alkyl group (e.g., methyl),
(b) an amino group optionally mono- or di-substituted by $C_{1-6}$ alkoxy-carbonyl group(s) (e.g., tert-butoxycarbonyl),
(c) a carboxy group, and
(d) a $C_{1-6}$ alkoxy-carbonyl group (e.g., tert-butoxycarbonyl),
(iv) a $C_{6-10}$ aryl group (e.g., phenyl),
(v) a $C_{6-10}$ aryloxy group (e.g., phenoxy) optionally substituted by halogen atom(s) (e.g., a bromine atom),
(vi) a $C_{7-13}$ aralkyloxy group (e.g., benzyloxy), and
(vii) a heterocyclyloxy group (e.g., pyridyloxy);
$B^1$ is a group represented by

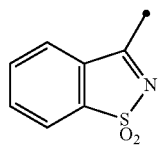

wherein • means a bonding site;
$X^1$ is a sulfur atom;
$X^2$ is an oxygen atom;
Y is a bond or —CH=CH—; and
Z is —NH—.
[Compound D-I]
In the formula (I), compound (I) wherein the partial structure represented by

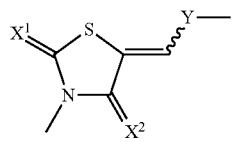

is a partial structure represented by

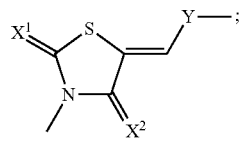

A is a phenyl group optionally substituted by the substituent(s) selected from
(i) a halogen atom (e.g., a bromine atom),
(ii) a nitro group,
(iii) a $C_{1-6}$ alkoxy group (e.g., methoxy, ethoxy) optionally substituted by $C_{6-10}$ aryloxy group(s) (e.g., phenoxy) optionally substituted by the substituent(s) selected from a nitro group and a $C_{1-6}$ alkyl group (e.g., methyl),
(v) a $C_{6-10}$ aryloxy group (e.g., phenoxy), and
(vi) a $C_{7-13}$ aralkyloxy group (e.g., benzyloxy);
$B^1$ is a group represented by

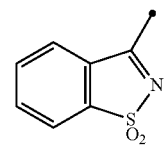

wherein • means a bonding site;
$X^1$ is a sulfur atom;
$X^2$ is an oxygen atom;
Y is a bond or —CH=CH—; and
Z is —NH—.
[Compound A'-II]
In the formula (II), compound (II) wherein the partial structure represented by

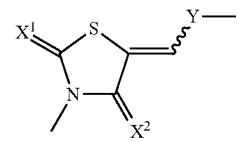

is a partial structure represented by

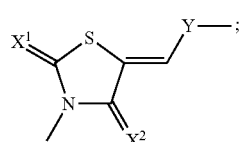

ring $A^1$ and ring $A^2$ are each independently an optionally substituted benzene ring;
$B^2$ is an optionally substituted 5- or 6-membered cyclic group (a phenyl group, a $C_{5-6}$ cycloalkyl group, a 5- or 6-membered heterocyclic group optionally fused with a benzene ring) or an amino group (in this case, Z is preferably a bond);

X$^1$ is a sulfur atom;
X$^2$ is an oxygen atom;
Y is a bond or a spacer having 1 or 2 atoms;
Z is a bond, or a group represented by —(CH$_2$)n$^1$-V$^3$—(CH$_2$)n$^2$- wherein V$^3$ is a bond, —CO—, —NHCO—, —CONH—, —SO$_2$NH— or —SO$_2$NHCO—, and n$^1$ and n$^2$ are each independently an integer of 0 to 2; and
W is an oxygen atom, a sulfur atom, or a group represented by the formula: —V$^1$—(CH$_2$)m-V$^2$— wherein V$^1$ and V$^2$ are each independently a bond or an oxygen atom, and m is an integer of 1 to 3.

[Compound A'-IIa]

In the formula (II), compound (II) wherein
the partial structure represented by

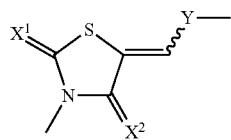

is a partial structure represented by

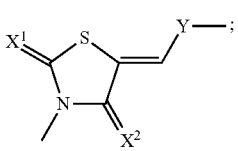

ring A$^1$ and ring A$^2$ are each independently an optionally substituted benzene ring;
B$^2$ is an optionally substituted 5- or 6-membered cyclic group (a phenyl group, a C$_{5-6}$ cycloalkyl group, a 5- or 6-membered heterocyclic group optionally fused with a benzene ring) or an amino group (in this case, Z is preferably a bond or —(CH$_2$)n$^1$-NHCO—(CH$_2$)n$^2$- wherein n$^1$ and n$^2$ are each independently an integer of 0 to 2);
X$^1$ is a sulfur atom;
X$^2$ is an oxygen atom;
Y is a bond or a spacer having 1 or 2 atoms;
Z is a bond, or a group represented by —(CH$_2$)n$^1$-V$^3$—(CH$_2$)n$^2$- wherein V$^3$ is a bond, —CO—, —NH—, —NHCO—, —CONH—, —SO$_2$NH— or —SO$_2$NHCO—, and n$^1$ and n$^2$ are each independently an integer of 0 to 2; and
W is an oxygen atom, a sulfur atom, or a group represented by the formula: —V$^1$—(CH$_2$)m-V$^2$— wherein V$^1$ and V$^2$ are each independently a bond or an oxygen atom, and m is an integer of 1 to 3.

[Compound B'-II]

In the formula (II), compound (II) wherein
the partial structure represented by

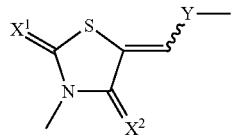

is a partial structure represented by

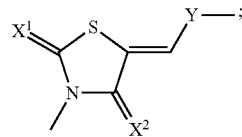

ring A$^1$ and ring A$^2$ are each independently an optionally substituted benzene ring;
B$^2$ is an optionally substituted phenyl group or an optionally substituted 5- or 6-membered nitrogen-containing heterocyclic group (optionally fused with a benzene ring);
X$^1$ is a sulfur atom;
X$^2$ is an oxygen atom;
Y is a bond or a spacer having 1 or 2 atoms;
Z is a bond, or a group represented by —(CH$_2$)n$^1$-V$^3$—(CH$_2$)n$^2$- wherein V$^3$ is a bond, —CO— or —CONH—, and n$^1$ and n$^2$ are each independently an integer of 0 to 2; and
W is an oxygen atom, a sulfur atom, or a group represented by the formula: —V$^1$—(CH$_2$)m-V$^2$— wherein V$^1$ and V$^2$ are each independently a bond or an oxygen atom, and m is an integer of 1 to 3.

[Compound B'-IIb]

In the formula (II), compound (II) wherein
the partial structure represented by

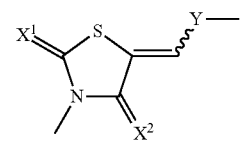

is a partial structure represented by

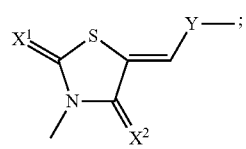

ring A$^1$ and ring A$^2$ are each independently an optionally substituted benzene ring;
B$^2$ is an optionally substituted phenyl group or an optionally substituted 5- or 6-membered nitrogen-containing heterocyclic group (optionally fused with a benzene ring);
X$^1$ is a sulfur atom;
X$^2$ is an oxygen atom;
Y is a bond or a spacer having 1 or 2 atoms;
Z is a bond, or a group represented by —(CH$_2$)n$^1$-V$^3$—(CH$_2$)n$^2$- wherein V$^3$ is a bond, —CO—, —NH—, —NHCO— or —CONH—, and n$^1$ and n$^2$ are each independently an integer of 0 to 2; and
W is an oxygen atom, a sulfur atom, or a group represented by the formula: —V$^1$—(CH$_2$)m-V$^2$— wherein V$^1$ and V$^2$ are each independently a bond or an oxygen atom, and m is an integer of 1 to 3.

[Compound C'-II]
In the formula (II), compound (II) wherein
the partial structure represented by

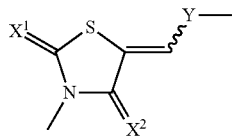

is a partial structure represented by

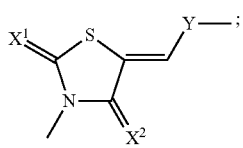

ring $A^1$ and ring $A^2$ are each independently an optionally substituted benzene ring;
$B^2$ is an optionally substituted phenyl group or an optionally substituted 5- or 6-membered nitrogen-containing heterocyclic group (optionally fused with a benzene ring);
$X^1$ is a sulfur atom;
$X^2$ is an oxygen atom;
Y is a bond or a spacer having 1 or 2 atoms;
Z is a bond, or a group represented by —$(CH_2)n^1$-$V^3$—$(CH_2)n^2$- wherein $V^3$ is a bond, —CO— or —CONH—, and $n^1$ and $n^2$ are each independently an integer of 0 to 2; and
W is an oxygen atom, a sulfur atom, or a group represented by the formula: —$V^1$—$(CH_2)m$-$V^2$— wherein $V^1$ and $V^2$ are each independently a bond or an oxygen atom, and m is an integer of 1 to 3.

[Compound C'-IIa]
In the formula (II), compound (II) wherein
the partial structure represented by

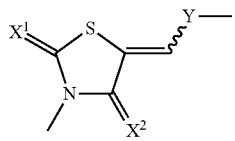

is a partial structure represented by

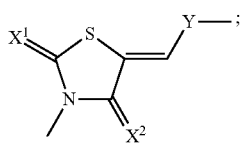

ring $A^1$ and ring $A^2$ are each independently an optionally substituted benzene ring;
$B^2$ is an optionally substituted phenyl group or an optionally substituted 5- or 6-membered nitrogen-containing heterocyclic group (optionally fused with a benzene ring);
$X^1$ is a sulfur atom;
$X^2$ is an oxygen atom;
Y is a bond or a spacer having 1 or 2 atoms;
Z is a bond, or a group represented by —$(CH_2)n^1$-$V^3$—$(CH_2)n^2$- wherein $V^3$ is a bond, —CO—, —NH—, —NHCO— or —CONH—, and $n^1$ and $n^2$ are each independently an integer of 0 to 2; and
W is an oxygen atom, a sulfur atom, or a group represented by the formula: —$V^1$—$(CH_2)m$-$V^2$— wherein $V^1$ and $V^2$ are each independently a bond or an oxygen atom, and m is an integer of 1 to 3.

[Compound A-II]
In the formula (II), compound (II) wherein
the partial structure represented by

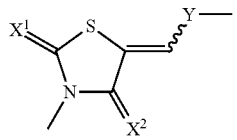

is a partial structure represented by

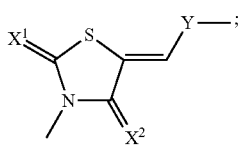

ring $A^1$ is a benzene ring optionally substituted by the substituent(s) selected from
(1) a halogen atom (e.g., a chlorine atom, a bromine atom)
(2) a $C_{1-6}$ alkyl group (e.g., methyl), and
(3) a $C_{1-6}$ alkoxy group (e.g., methoxy);
ring $A^2$ is a benzene ring optionally substituted by the substituent(s) selected from
(1) a halogen atom (e.g., a fluorine atom, a chlorine atom, a bromine atom)
(2) a nitro group,
(3) a cyano group,
(4) a $C_{1-6}$ alkyl group (e.g., methyl), and
(5) a $C_{1-6}$ alkoxy group (e.g., methoxy);
$B^2$ is
(1) a phenyl group, a $C_{5-6}$ cycloalkyl group (e.g., cyclohexyl), or a 5- or 6-membered heterocyclic group optionally fused with a benzene ring (e.g., tetrahydrofuryl, pyrrolidinyl, piperidyl, piperazinyl, pyridyl, morpholinyl, thiomorpholinyl, 1,1-dioxidothiomorpholinyl, 1,1-dioxido-1,2-benzisothiazolyl, indolyl, tetrahydroisoquinolyl, benzodioxolyl, 2,2-dioxido-1,2,3-oxathiazine), each of which is optionally substituted by substituent(s) selected from
(i) a nitro group,
(ii) a hydroxy group,
(iii) a carboxy group,
(iv) a sulfamoyl group,
(v) a sulfo group or a sulfonato group,
(vi) a $C_{1-6}$ alkyl group,
(vii) a $C_{7-13}$ aralkyl group,
(viii) a $C_{1-6}$ alkoxy group,
(ix) a $C_{1-6}$ alkyl-carbonyl group optionally substituted by $C_{1-6}$ alkoxy group(s),
(x) a $C_{1-6}$ alkoxy-carbonyl group,
(xi) a $C_{1-6}$ alkylsulfanyl group, and
(xii) a $C_{1-6}$ alkylsulfonyl group, or (2) an amino group (in this case, Z is preferably a bond);
X$^1$ is a sulfur atom;
X$^2$ is an oxygen atom;
Y is a bond or a spacer having 1 or 2 atoms;
Z is a bond, or a group represented by —(CH$_2$)n$^1$-V$^3$—(CH$_2$)n$^2$- wherein V$^3$ is a bond, —CO—, —NHCO—, —CONH—, —SO$_2$NH— or —SO$_2$NHCO—, and n$^1$ and n$^2$ are each independently an integer of 0 to 2; and
W is an oxygen atom, a sulfur atom, or a group represented by the formula: —V$^1$—(CH$_2$)m-V$^2$— wherein V$^1$ and V$^2$ are each independently a bond or an oxygen atom, and m is an integer of 1 to 3.

[Compound A-IIa]
In the formula (II), compound (II) wherein
the partial structure represented by

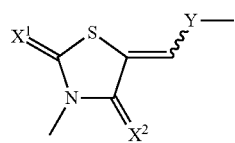

is a partial structure represented by

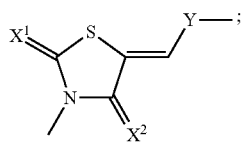

ring A$^1$ is a benzene ring optionally substituted by the substituent(s) selected from
(1) a halogen atom (e.g., a chlorine atom, a bromine atom)
(2) a C$_{1-6}$ alkyl group (e.g., methyl), and
(3) a C$_{1-6}$ alkoxy group (e.g., methoxy);
ring A$^2$ is a benzene ring optionally substituted by the substituent(s) selected from
(1) a halogen atom (e.g., a fluorine atom, a chlorine atom, a bromine atom)
(2) a nitro group,
(3) a cyano group,
(4) a C$_{1-6}$ alkyl group (e.g., methyl), and
(5) a C$_{1-6}$ alkoxy group (e.g., methoxy);
B$^2$ is
(1) a phenyl group, a C$_{5-6}$ cycloalkyl group (e.g., cyclohexyl), or a 5- or 6-membered heterocyclic group optionally fused with a benzene ring (e.g., tetrahydrofuryl, pyrrolidinyl, piperidyl, piperazinyl, pyridyl, morpholinyl, thiomorpholinyl, 1,1-dioxidothiomorpholinyl, 1,1-dioxido-1,2-benzisothiazolyl, indolyl, tetrahydroisoquinolyl, benzodioxolyl, 2,2-dioxido-1,2,3-oxathiazine), each of which is optionally substituted by substituent(s) selected from
(i) a nitro group,
(ii) a hydroxy group,
(iii) a carboxy group,
(iv) a sulfamoyl group,
(v) a sulfo group or a sulfonato group,
(vi) a C$_{1-6}$ alkyl group,
(vii) a C$_{7-13}$ aralkyl group,
(viii) a C$_{1-6}$ alkoxy group,
(ix) a C$_{1-6}$ alkyl-carbonyl group optionally substituted by C$_{1-6}$ alkoxy group(s),
(x) a C$_{1-6}$ alkoxy-carbonyl group,
(xi) a C$_{1-6}$ alkylsulfanyl group, and
(xii) a C$_{1-6}$ alkylsulfonyl group, or
(2) an amino group (in this case, Z is preferably a bond or —(CH$_2$)n$^1$-NHCO—(CH$_2$)n$^2$- wherein n$^1$ and n$^2$ are each independently an integer of 0 to 2);
X$^1$ is a sulfur atom;
X$^2$ is an oxygen atom;
Y is a bond or a spacer having 1 or 2 atoms;
Z is a bond, or a group represented by —(CH$_2$)n$^1$-V$^3$—(CH$_2$)n$^2$- wherein V$^3$ is a bond, —CO—, —NH—, —NHCO—, —CONH—, —SO$_2$NH— or —SO$_2$NHCO—, and n$^1$ and n$^2$ are each independently an integer of 0 to 2; and
W is an oxygen atom, a sulfur atom, or a group represented by the formula: —V$^1$—(CH$_2$)m-V$^2$— wherein V$^1$ and V$^2$ are each independently a bond or an oxygen atom, and m is an integer of 1 to 3.

[Compound B-II]
In the formula (II), compound (II) wherein
the partial structure represented by

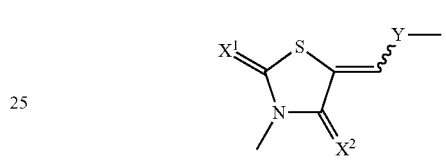

is a partial structure represented by

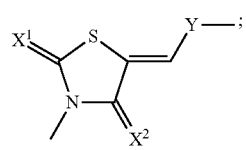

ring A$^1$ is a benzene ring optionally substituted by halogen atom(s) (e.g., a chlorine atom);
ring A$^2$ is a benzene ring optionally substituted by the substituent(s) selected from
(1) a halogen atom (e.g., a fluorine atom, a chlorine atom, a bromine atom)
(2) a nitro group, and
(3) a C$_{1-6}$ alkyl group (e.g., methyl);
B$^2$ is
(1) a phenyl group, a C$_{5-6}$ cycloalkyl group (e.g., cyclohexyl), or a 5- or 6-membered heterocyclic group optionally fused with a benzene ring (e.g., tetrahydrofuryl, pyrrolidinyl, piperidyl, pyridyl, morpholinyl, 1,1-dioxidothiomorpholinyl, 1,1-dioxido-1,2-benzisothiazolyl), each of which is optionally substituted by substituent(s) selected from
(i) a hydroxy group,
(ii) a sulfamoyl group,
(iii) a sulfo group or a sulfonato group,
(iv) a C$_{1-6}$ alkyl-carbonyl group optionally substituted by C$_{1-6}$ alkoxy group(s),
(v) a C$_{1-6}$ alkoxy-carbonyl group, and
(vi) a C$_{1-6}$ alkylsulfonyl group, or
(2) an amino group (in this case, Z is preferably a bond);
X$^1$ is a sulfur atom;
X$^2$ is an oxygen atom;
Y is a bond;
Z is a bond, or a group represented by —(CH$_2$)n$^1$-V$^3$—(CH$_2$)n$^2$- wherein V$^3$ is a bond, —CO— or —CONH—, and n$^1$ and n$^2$ are each independently an integer of 0 to 2; and W is an oxygen atom, —OCH$_2$CH$_2$O—, —OCH$_2$CH$_2$CH$_2$O— or —OCH$_2$—.

[Compound B-IIa]

In the formula (II), compound (II) wherein the partial structure represented by

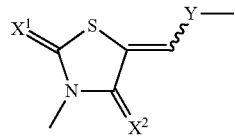

is a partial structure represented by

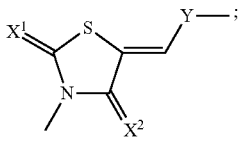

ring A$^1$ is a benzene ring optionally substituted by halogen atom(s) (e.g., a chlorine atom);

ring A$^2$ is a benzene ring, optionally substituted by the substituent(s) selected from
(1) a halogen atom (e.g., a fluorine atom, a chlorine atom, a bromine atom)
(2) a nitro group, and
(3) a C$_{1-6}$ alkyl group (e.g., methyl);

B$^2$ is
(1) a phenyl group, a C$_{5-6}$ cycloalkyl group (e.g., cyclohexyl), or a 5- or 6-membered heterocyclic group optionally fused with a benzene ring (e.g., tetrahydrofuryl, pyrrolidinyl, piperidyl, pyridyl, morpholinyl, 1,1-dioxidothiomorpholinyl, 1,1-dioxido-1,2-benzisothiazolyl), each of which is optionally substituted by substituent(s) selected from
   (i) a hydroxy group,
   (ii) a sulfamoyl group,
   (iii) a sulfo group or a sulfonato group,
   (iv) a C$_{1-6}$ alkyl-carbonyl group optionally substituted by C$_{1-6}$ alkoxy group(s),
   (v) a C$_{1-6}$ alkoxy-carbonyl group, and
   (vi) a C$_{1-6}$ alkylsulfonyl group, or
(2) an amino group (in this case, Z is preferably a bond or —(CH$_2$)n$^1$-NHCO—(CH$_2$)n$^2$- wherein n$^1$ and n$^2$ are each independently an integer of 0 to 2);

X$^1$ is a sulfur atom;

X$^2$ is an oxygen atom;

Y is a bond;

Z is a bond, or a group represented by —(CH$_2$)n$^1$-V$^3$—(CH$_2$)n$^2$- wherein V$^3$ is a bond, —CO—, —NH—, —NHCO— or —CONH—, and n$^1$ and n$^2$ are each independently an integer of 0 to 2; and W is an oxygen atom, —OCH$_2$CH$_2$O—, —OCH$_2$CH$_2$CH$_2$O— or —OCH$_2$—.

[Compound C-II]

In the formula (II), compound (II) wherein the partial structure represented by

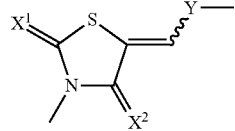

is a partial structure represented by

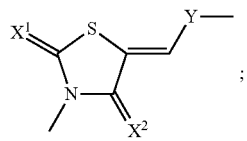

ring A$^1$ is an unsubstituted benzene ring;

ring A$^2$ is a benzene ring optionally substituted by the substituent(s) selected from
(1) a nitro group, and
(2) a C$_{1-6}$ alkyl group (e.g., methyl);

B$^2$ is a phenyl group or a 5- or 6-membered nitrogen-containing heterocyclic group (e.g., pyrrolidinyl, piperidyl, pyridyl, 1,1-dioxidothiomorpholinyl, 1,1-dioxido-1,2-benzisothiazolyl), each of which is optionally substituted by substituent(s) selected from
   (i) a C$_{1-6}$ alkoxy-carbonyl group,
   (ii) a sulfamoyl group, and
   (iii) a C$_{1-6}$ alkylsulfonyl group;

X$^1$ is a sulfur atom;

X$^2$ is an oxygen atom;

Y is a bond;

Z is a bond, —CONH—, —COCH$_2$—, —CH$_2$— or —(CH$_2$)$_2$—; and

W is an oxygen atom, —OCH$_2$CH$_2$O— or —OCH$_2$—.

[Compound C-IIa]

In the formula (II), compound (II) wherein the partial structure represented by

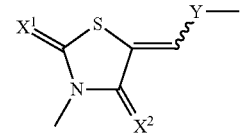

is a partial structure represented by

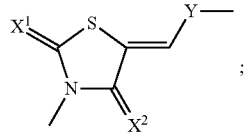

ring A$^1$ is an unsubstituted benzene ring;

ring A$^2$ is a benzene ring optionally substituted by the substituent(s) selected from
(1) a nitro group, and
(2) a C$_{1-6}$ alkyl group (e.g., methyl);

B$^2$ is a phenyl group or a 5- or 6-membered nitrogen-containing heterocyclic group (e.g., pyrrolidinyl, piperidyl, pyridyl, 1,1-dioxidothiomorpholinyl, 1,1-dioxido-1,2-benzisothiazolyl), each of which is optionally substituted by substituent(s) selected from (i) a $C_{1-6}$ alkoxy-carbonyl group,
(ii) a sulfamoyl group, and
(iii) a $C_{1-6}$ alkylsulfonyl group;
$X^1$ is a sulfur atom;
$X^2$ is an oxygen atom;
Y is a bond;
Z is a bond, —NH—, —CONH—, —COCH$_2$—, —CH$_2$— or —(CH$_2$)$_2$—; and
W is an oxygen atom, —OCH$_2$CH$_2$O— or —OCH$_2$—.
[Compound D-IIa]
In the formula (II), compound (II) wherein the partial structure represented by

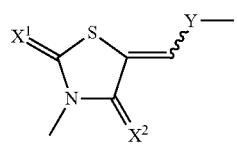

is a partial structure represented by

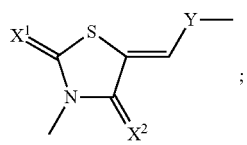

ring $A^1$ is an unsubstituted benzene ring;
ring $A^2$ is a benzene ring optionally substituted by the substituent(s) selected from
(1) a nitro group, and
(2) a $C_{1-6}$ alkyl group (e.g., methyl);
$B^2$ is a phenyl group or a 5- or 6-membered nitrogen-containing heterocyclic group (e.g., piperidyl, 1,1-dioxidothiomorpholinyl, 1,1-dioxido-1,2-benzisothiazolyl), each of which is optionally substituted by substituent(s) selected from
(i) a sulfamoyl group, and
(ii) a $C_{1-6}$ alkylsulfonyl group;
$X^1$ is a sulfur atom;
$X^2$ is an oxygen atom;
Y is a bond;
Z is —NH—, —CONH—, —CH$_2$— or —(CH$_2$)$_2$—; and
W is an oxygen atom, —OCH$_2$CH$_2$O— or —OCH$_2$—.
Particularly preferably compounds are as follows.
A compound represented by

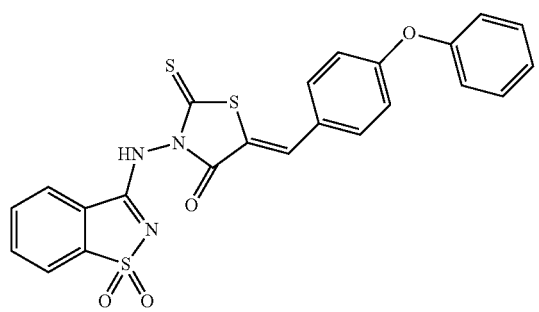 [SMILES: O=C1/C(=C/c2ccc(Oc3ccccc3)cc2)SC(=S)N1NC1=NS(=O)(=O)c2ccccc21]

(3-[(4-oxo-5-(4-phenoxybenzylidene)-2-thioxothiazolidin-3-yl)amino]-1,2-benzisothiazole 1,1-dioxide) or a salt thereof.

A compound represented by

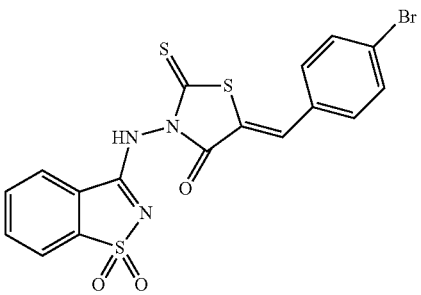 [SMILES: O=C1/C(=C/c2ccc(Br)cc2)SC(=S)N1NC1=NS(=O)(=O)c2ccccc21]

(3-([5-(4-bromobenzylidene)-4-oxo-2-thioxothiazolidin-3-yl)amino]-1,2-benzisothiazole 1,1-dioxide) or a salt thereof.

A compound represented by

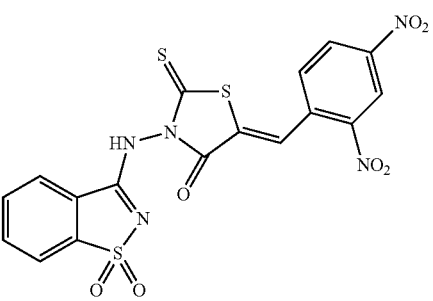 [SMILES: O=C1/C(=C/c2ccc([N+](=O)[O-])cc2[N+](=O)[O-])SC(=S)N1NC1=NS(=O)(=O)c2ccccc21]

(3-([5-(2,4-dinitrobenzylidene)-4-oxo-2-thioxothiazolidin-3-yl)amino]-1,2-benzisothiazole 1,1-dioxide) or a salt thereof.

A compound represented by

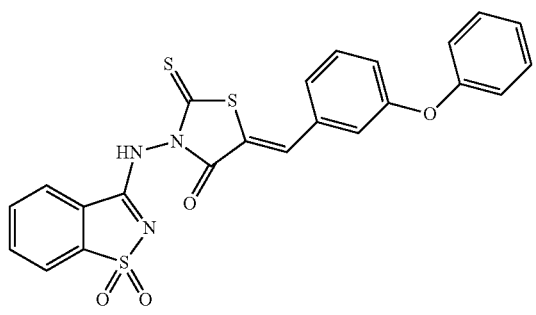 [SMILES: O=C1/C(=C/c2cccc(Oc3ccccc3)c2)SC(=S)N1NC1=NS(=O)(=O)c2ccccc21]

(3-[(4-oxo-5-(3-phenoxybenzylidene)-2-thioxothiazolidin-3-yl)amino]-1,2-benzisothiazole 1,1-dioxide) or a salt thereof.

A compound represented by

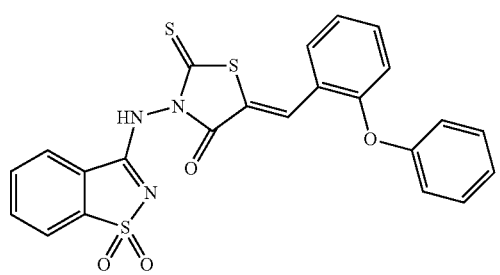 [SMILES: O=C1/C(=C/c2ccccc2Oc2ccccc2)SC(=S)N1NC1=NS(=O)(=O)c2ccccc21]

(3-[(4-oxo-5-(2-phenoxybenzylidene)-2-thioxothiazolidin-3-yl)amino]-1,2-benzisothiazole 1,1-dioxide) or a salt thereof.

A compound represented by

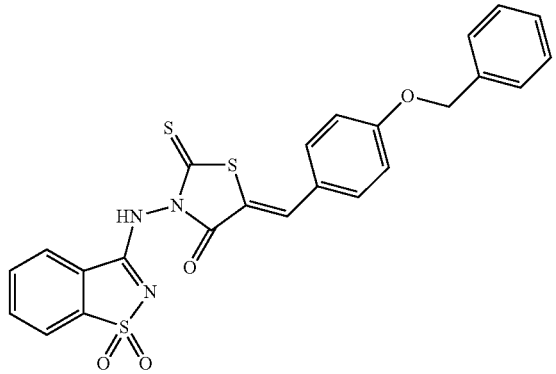 [SMILES: O=C1/C(=C/c2ccc(OCc3ccccc3)cc2)SC(=S)N1NC1=NS(=O)(=O)c2ccccc21]

(3-([5-(4-benzyloxybenzylidene)-4-oxo-2-thioxothiazolidin-3-yl)amino]-1,2-benzisothiazole 1,1-dioxide) or a salt thereof.

A compound represented by

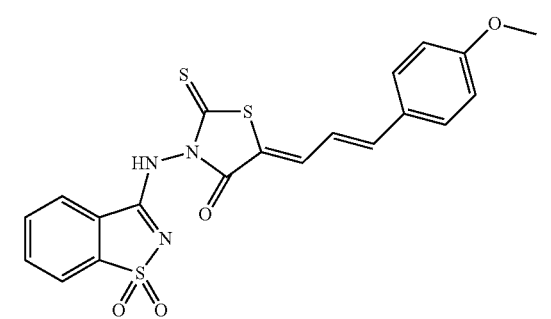 [SMILES: COc1ccc(/C=C/C=C2\SC(=S)N(NC3=NS(=O)(=O)c4ccccc43)C2=O)cc1]

(3-[(4-oxo-5-(3-(4-methoxyphenyl)allylidene)-2-thioxothiazolidin-3-yl)amino]-1,2-benzisothiazole 1,1-dioxide) or a salt thereof.

A compound represented by

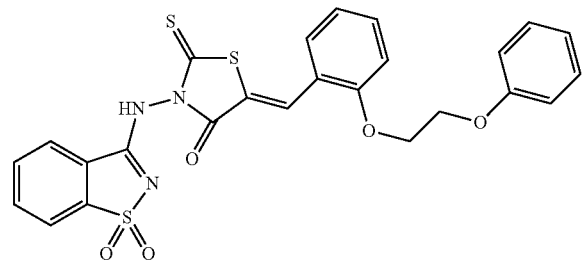 [SMILES: O=C1/C(=C/c2ccccc2OCCOc2ccccc2)SC(=S)N1NC1=NS(=O)(=O)c2ccccc21]

(3-[(4-oxo-5-(2-(2-phenoxyethoxy)benzylidene)-2-thioxothiazolidin-3-yl)amino]-1,2-benzisothiazole 1,1-dioxide) or a salt thereof.

A compound represented by

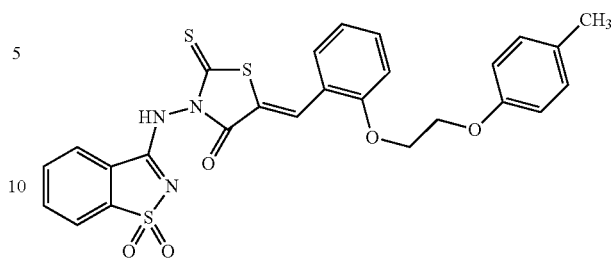

(3-[(4-oxo-5-(2-(2-(4-methylphenoxy)ethoxy)benzylidene)-2-thioxothiazolidin-3-yl)amino]-1,2-benzisothiazole 1,1-dioxide) or a salt thereof.

A compound represented by

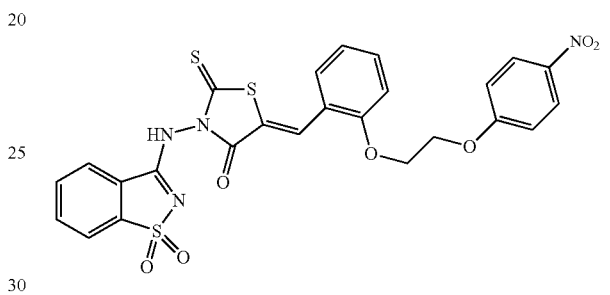

(3-[(4-oxo-5-(2-(2-(4-nitrophenoxy)ethoxy)benzylidene)-2-thioxothiazolidin-3-yl)amino]-1,2-benzisothiazole 1,1-dioxide) or a salt thereof.

A compound represented by

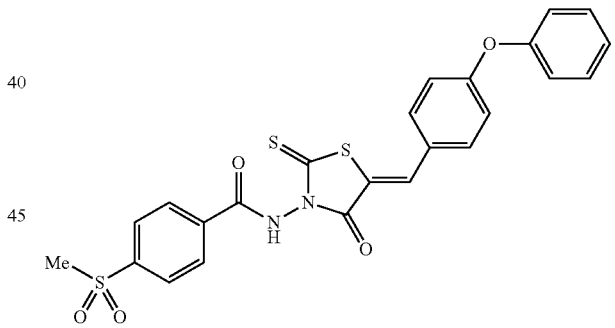

(3-[(4-methylsulfonylphenyl)carbonylamino]-5-(4-phenoxybenzylidene)-2-thioxothiazolidin-4-one) or a salt thereof.

A compound represented by

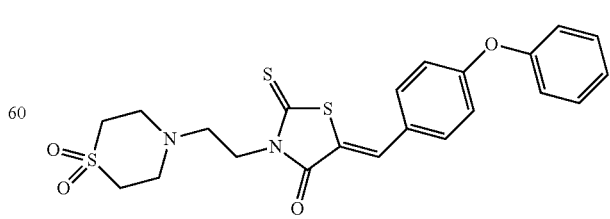

(4-[2-(4-oxo-5-(4-phenoxybenzylidene)-2-thioxothiazolidin-3-yl)ethyl]thiomorpholine 1,1-dioxide) or a salt thereof.

A compound represented by

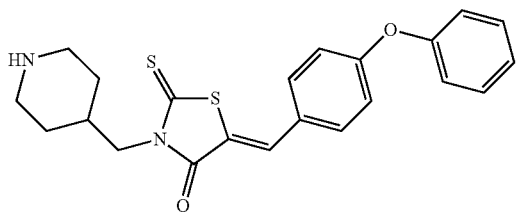 [SMILES: O=C1/C(=C/c2ccc(Oc3ccccc3)cc2)SC(=S)N1CC1CCNCC1]

(5-(4-phenoxybenzylidene)-3-(piperidin-4-ylmethyl)-2-thioxothiazolidin-4-one) or a salt thereof.

A compound represented by

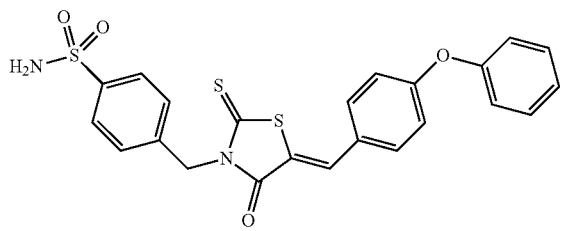 [SMILES: NS(=O)(=O)c1ccc(CN2C(=O)/C(=C/c3ccc(Oc4ccccc4)cc3)SC2=S)cc1]

(4-[(4-oxo-5-(4-phenoxybenzylidene)-2-thioxothiazolidin-3-yl)methyl]benzenesulfonamide) or a salt thereof.

A compound represented by

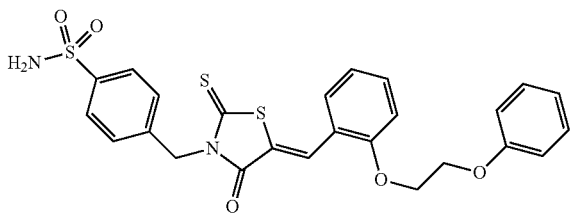 [SMILES: NS(=O)(=O)c1ccc(CN2C(=O)/C(=C/c3ccccc3OCCOc3ccccc3)SC2=S)cc1]

(4-[(4-oxo-5-(2-(2-phenoxyethoxy)benzylidene)-2-thioxothiazolidin-3-yl)methyl]benzenesulfonamide) or a salt thereof.

When compound (I), compound (II) or compound (I') (hereinafter to be collectively referred as compound (I')) is in the form of a salt, examples of the salt include metal salts, ammonium salts, salts with an organic base, salts with an inorganic acid, salts with an organic acid, salts with a basic or acidic amino acid, and the like. Preferable examples of the metal salt include alkaline metal salts such as sodium salt, potassium salt and the like; alkaline earth metal salts such as calcium salt, magnesium salt, barium salt and the like; aluminum salt, and the like. Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with an inorganic acid include salts with hydrochloric acid, hydrobromic acid, nitric acid, sulfuric acid, phosphoric acid and the like. Preferable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with a basic amino acid include salts with arginine, lysine, ornithine and the like. Preferable examples of the salt with an acidic amino acid include salts with aspartic acid, glutamic acid and the like.

Among the above-mentioned salts, pharmaceutically acceptable salts are preferable. When compound (I') has an acidic functional group, examples thereof include inorganic salts such as alkali metal salts (e.g., sodium salt, potassium salt etc.), alkaline-earth metal salts (e.g., calcium salt, magnesium salt etc.) and the like, ammonium salt and the like. When compound (I') has a basic functional group, examples thereof include salts with a inorganic acid such as hydrochloric acid, hydrobromic acid, nitric acid, sulfuric acid, phosphoric acid and the like, and salts with an organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

The production method of the compound of the present invention is explained below.

The production method of the compound (I') is explained below by referring to representative production methods, which are not limited.

Compound (I') can be produced according to the method shown in the following Reaction Schemes 1-4, method analogous thereto or the like. Compound (I) and (II) can be produced in the same manner as in the production of compound (I').

Each raw material compound may be in the form of a salt as long as it does not inhibit the reaction. Examples of the salt include those similar to the salt of compound (I').

Raw material compounds can be commercially available, or can be produced according to a method known per se or a method analogous thereto, unless otherwise referred to specific production method.

Compound (I') can be produced according to the method shown in Reaction Schemes 1-4.

Reaction Scheme 1

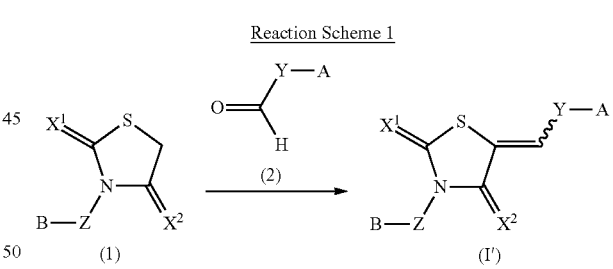

wherein each symbol is as defined above.

Compound (I') can be produced by reacting compound (1) with compound (2) in the presence of a base, in a solvent.

The amount of compound (2) to be used is generally 1.0-2.0 equivalents, preferably 1.0-1.5 equivalents, relative to compound (1).

Examples of the base include organic bases such as triethylamine, piperidine, N,N-diisopropylethylamine, sodium acetate and the like; and inorganic bases such as sodium hydrogen carbonate and the like. The amount of the base to be used is generally 0-4 equivalents, preferably 1-2 equivalents, relative to compound (1).

Examples of the solvent include nitrile solvents such as acetonitrile and the like; alcohol solvents such as methanol, ethanol and the like; water and the like.

The reaction temperature is generally 0-100° C., preferably room temperature-100° C., and the reaction time is generally 2-24 hr.

Reaction Scheme 2

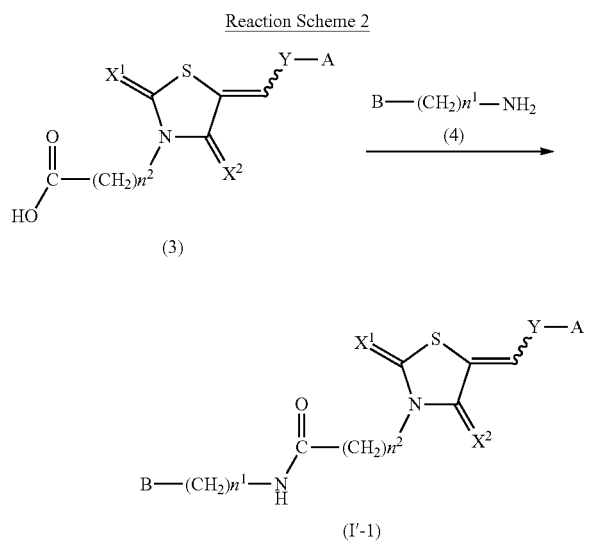

(I'-1)

Reaction Scheme 3

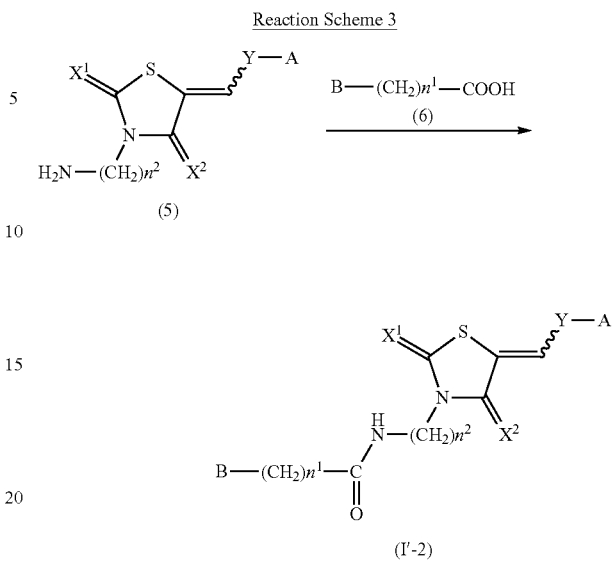

(I'-2)

wherein each symbol is as defined above.

Compound (I'-1) can be produced by reacting compound (3) with compound (4) in the presence of a condensing agent, in a solvent.

The amount of compound (4) to be used is generally 1-2 equivalents, preferably 1-1.2 equivalents, relative to compound (3).

Examples of the condensing agent include dicyclohexyl carbodiimide (DCC), 1-ethyl-3-(3-dimethylaminopropyl) carbodiimide hydrochloride (EDC HCl) and the like. The amount of the condensing agent to be used is generally 1-2 equivalents, preferably 1-1.5 equivalents, relative to compound (3).

Where necessary, the reaction may be carried out in the presence of 1-hydroxybenzotriazole (HOBt) and the like.

Examples of the solvent include methylene chloride, N,N-dimethylformamide, N-methylpyrrolidone and the like.

The reaction temperature is generally 0-30° C., preferably 0-20° C., and the reaction time is generally 2-24 hr.

Alternatively, compound (I'-1) can also be produced by converting compound (3) to the corresponding acid halide with a halogenating agent, and then reacting the acid halide with compound (4) in the presence of a base, in a solvent.

The amount of compound (4) to be used is generally 1-2 equivalents, preferably 1-1.2 equivalents, relative to compound (3).

Examples of the halogenating agent include thionyl chloride, oxalyl chloride, phosphorus trichloride, sulfuryl chloride and the like. The amount of the halogenating agent to be used is generally 1-2 equivalents, preferably 1-1.5 equivalents, relative to compound (4).

Examples of the base include organic bases such as triethylamine, N,N-diisopropylethylamine and the like. The amount of the base to be used is generally 1-2 equivalents, preferably 1-1.5 equivalents, relative to compound (3).

Examples of the solvent include methylene chloride, chloroform and toluene.

The reaction temperature is generally 0-80° C., and the reaction time is generally 2-24 hr.

wherein each symbol is as defined above.

Compound (I'-2) can be produced by reacting compound (5) with compound (6) in the presence of a condensing agent, in a solvent.

The amount of compound (6) to be used is generally 1-2 equivalents, preferably 1-1.5 equivalents, relative to compound (5).

Examples of the condensing agent include dicyclohexyl carbodiimide (DCC), 1-ethyl-3-(3-dimethylaminopropyl) carbodiimide hydrochloride (EDC.HCl) and the like. The amount of the condensing agent to be used is generally 1-2 equivalents, preferably 1-1.5 equivalents, relative to compound (5).

Examples of the solvent include methylene chloride, N,N-dimethylformamide, N-methylpyrrolidone and the like.

The reaction temperature is generally 0-50° C., preferably 0-20° C., and the reaction time is generally 2-24 hr.

Alternatively, compound (I'-2) can also be produced by converting compound (6) to the corresponding acid halide with a halogenating agent, and then reacting the acid halide with compound (5) in the presence of a base, in a solvent.

The amount of compound (6) to be used is generally 1-2 equivalents, preferably 1-1.5 equivalents, relative to compound (5).

Examples of the halogenating agent include thionyl chloride, oxalyl chloride, phosphorus trichloride, sulfuryl chloride and the like. The amount of the halogenating agent to be used is generally 1-2 equivalents, preferably 1-1.5 equivalents, relative to compound (6).

Examples of the base include organic bases such as triethylamine, N,N-diisopropylethylamine and the like. The amount of the base to be used is generally 1-2 equivalents, preferably 1-1.5 equivalents, relative to compound (5).

Examples of the solvent include methylene chloride, chloroform and toluene.

The reaction temperature is generally 0-100° C., preferably 0-20° C., and the reaction time is generally 2-24 hr.

Reaction Scheme 4

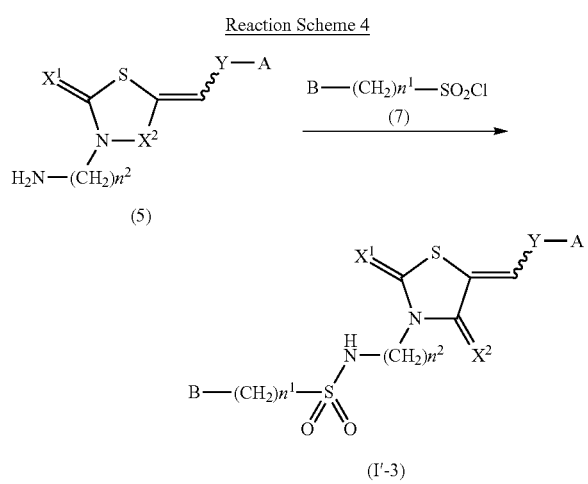

wherein each symbol is as defined above.

Compound (I'-3) can be produced by reacting compound (5) with compound (7) in the presence of a base, in a solvent.

The amount of compound (7) to be used is generally 1-2 equivalents, preferably 1-1.5 equivalents, relative to compound (5).

Examples of the base include organic bases such as triethylamine, N,N-diisopropylethylamine and the like. The amount of the base to be used is generally 1-2 equivalents, preferably 1-1.5 equivalents, relative to compound (5).

Examples of the solvent include methylene chloride, chloroform and toluene.

The reaction temperature is generally 0-100° C., preferably 0-20° C., and the reaction time is generally 2-24 hr.

Compounds (1)-(7) which are raw material compounds can be commercially available, or can be produced according to the below-mentioned Preparation Examples 1-7 or a method known per se.

In each reaction of the synthesis of the objective compound and raw material compound, when the raw material compound has an amino group, a carboxyl group or a hydroxy group as a substituent, a protecting group generally used in peptide chemistry and the like may be introduced into these substituents. By removing the protecting group as necessary after the reaction, the objective compound can be obtained.

Examples of the protecting group include those described in "Protective Groups in Organic Synthesis, 3rd Edition", Wiley-Interscience, 1999, Theodora W. Greene, Peter G. M. Wuts.

Examples of the amino-protecting group include a formyl group, a $C_{1-6}$ alkyl-carbonyl group (e.g., acetyl, propionyl groups etc.), a phenylcarbonyl group, a $C_{1-6}$ alkyl-oxycarbonyl group (e.g., methoxycarbonyl, ethoxycarbonyl groups etc.), an aryloxycarbonyl group (e.g., a phenyloxycarbonyl group etc.), a $C_{7-10}$ aralkyl-carbonyl group (e.g., a benzyloxycarbonyl group etc.), a benzyl group, a benzhydryl group, a trityl group, a phthaloyl group and the like, each of which optionally has substituent(s). Examples of the substituent include a halogen atom (e.g., fluorine, chlorine, bromine, iodine atoms etc.), a $C_{1-6}$ alkyl-carbonyl group (e.g., acetyl, propionyl, butylcarbonyl groups etc.), a nitro group and the like, and the number of the substituents is about 1 to 3.

Examples of the carboxyl-protecting group include a $C_{1-6}$ alkyl group (e.g., methyl, ethyl, n-propyl, isopropyl, n-butyl, tert-butyl groups etc.), a phenyl group, a trityl group, a silyl group and the like, each of which optionally has substituent(s). Examples of the substituent include a halogen atom (e.g., fluorine, chlorine, bromine, iodine atoms etc.), a formyl group, a $C_{1-6}$ alkyl-carbonyl group (e.g., acetyl, propionyl, butylcarbonyl groups etc.), a nitro group and the like, and the number of the substituents is about 1 to 3.

Examples of the hydroxy-protecting group include a $C_{1-6}$ alkyl group (e.g., methyl, ethyl, n-propyl, isopropyl, n-butyl, tert-butyl groups etc.), a phenyl group, a $C_{7-10}$ aralkyl group (e.g., a benzyl group etc.), a formyl group, a $C_{1-6}$ alkyl-carbonyl group (e.g., acetyl, propionyl groups etc.), an aryloxycarbonyl group (e.g., a phenyloxycarbonyl group etc.), a $C_{7-10}$ aralkyl-carbonyl group (e.g., a benzyloxycarbonyl group etc.), a pyranyl group, a furanyl group, a silyl group and the like, each of which optionally has substituent(s). Examples of the substituent include a halogen atom (e.g., fluorine, chlorine, bromine, iodine atoms etc.), a $C_{1-6}$ alkyl group, a phenyl group, a $C_{7-10}$ aralkyl group, a nitro group and the like, and the number of the substituents is about 1 to 4.

These protecting groups can be removed according to a method known per se or the method described in "Protective Groups in Organic Synthesis, 3rd Edition", Wiley-Interscience, 1999, Theodora W. Greene, Peter G. M. Wuts or the like, or method analogous thereto. Specifically, a method by treating with acid, base, reduction, ultraviolet rays, hydrazine, phenylhydrazine, sodium N-methyldithiocarbamate, tetrabutylammonium fluoride, palladium acetate and the like can be employed.

In the above-mentioned method, when compound (I') is obtained in a free form, it may be converted to a salt with an inorganic acid (hydrochloric acid, sulfuric acid, hydrobromic acid etc.), an organic acid (methanesulfonic acid, benzenesulfonic acid, toluenesulfonic acid, oxalic acid, fumaric acid, maleic acid, tartaric acid etc.), an inorganic base (alkali metals such as sodium, potassium and the like; alkaline-earth metals such as calcium, magnesium and the like, aluminum, ammonium etc.) or an organic base (trimethylamine, triethylamine, pyridine, picoline, ethanolamine, diethanolamine, triethanolamine, dicyclohexyl amine, N,N'-dibenzylethylenediamine etc.) and the like, according to a conventional method. When compound (I') is obtained as a salt, it may also be converted to a free form or other salt according to a conventional method.

In the above-mentioned each reaction, when the raw material compound can be in the form of a salt, the compound can be used as a salt. Examples of the salt include those similar to the salt of compound (I').

The compound (I') of the present invention obtained by the above-mentioned method can be isolated and purified according to a conventional separation means (e.g., recrystallization, distillation, chromatography etc.).

When compound (I') has an optical isomer, a stereoisomer, a positional isomer or a rotamer, these are also encompassed in compound (I'), and can be obtained as a single product according to synthetic method and separation method known per se (concentration, solvent extraction, column chromatography, recrystallization etc.). For example, when compound (I') has an optical isomer, each optical isomer resolved from compound (I') is encompassed in compound (I').

The optical isomer can be produced according to a method known per se. Specifically, the optical isomer can be obtained by using an optically active synthetic intermediate, or by subjecting the racemic final product to optical resolution according to a conventional method.

Compound (I') may be a crystal, and the crystal form may be single or a mixture of crystal forms, both of which are encompassed in compound (I'). The crystal can be produced according to a crystallization method known per se.

The compound (I') may be a hydrate, a non-hydrate, a solvate or a non-solvate.

Since the present invention compound shows low toxicity, and can be used directly or in the form of a pharmaceutical composition by mixing with a pharmacologically acceptable carrier and the like, as an agent for the prophylaxis or treatment of various diseases mentioned below in a mammal (e.g., human, mouse, rat, rabbit, dog, cat, cow, horse, pig, monkey).

Examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, microcrystalline cellulose, low-substituted hydroxypropyl cellulose, sodium carboxymethylcellulose, gum arabic, pullulan, light anhydrous silicic acid, synthetic aluminum silicate and magnesium aluminate metasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, microcrystalline cellulose, sucrose, D-mannitol, trehalose, dextrin, pullulan, hydroxypropyl cellulose, hydroxypropyl methylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropyl cellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, laurylaminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethyl cellulose, hydroxyethyl cellulose, hydroxypropyl cellulose; polysorbates and polyoxyethylene hydrogenated castor oils.

Preferable examples of the isotonicity agent include sodium chloride, glycerol, D-mannitol, D-sorbitol and glucose.

Preferable examples of the buffer include buffers such as phosphates, acetates, carbonates, citrates and the like.

Preferable examples of the soothing agent include benzyl alcohol.

Preferable examples of the preservative include p-hydroxybenzoates, chlorobutanol, benzyl alcohol, phenethyl alcohol, dehydroacetic acid and sorbic acid.

Preferable examples of the antioxidant include sulfites and ascorbic acid.

Preferable examples of the colorant include water-soluble edible tar pigments (e.g., Food Color Red Nos. 2 and 3, Food Color Yellow Nos. 4 and 5, Food Color Blue Nos. 1 and 2), water insoluble lake pigments (e.g., aluminum salts of the above-mentioned water-soluble edible tar pigment) and natural pigments (e.g., β-carotene, chlorophyll, red iron oxide).

Preferable examples of the sweetening agent include saccharin sodium, dipotassium glycyrrhizinate, aspartame and stevia.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These can be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition varies depending on the dosage form, dose of the compound of the present invention and the like, it is, for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, iron sesquioxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

Since the present invention compound has an excellent Ras function inhibitory action, it is useful as an agent for the prophylaxis or treatment of a cancer (e.g., pancreatic cancer, colon cancer, rectum cancer, thyroid cancer, seminoma, myelodysplastic syndrome, lung cancer (non-small cell cancer), acute myelogenous leukemia, ovarian cancer, liver cancer, malignant melanoma, skin cancer, bladder cancer, breast cancer, stomach cancer, adrenal tumor, gallbladder cancer, bile duct cancer, bone tumor, central nervous system tumor, uterine cancer (cervical cancer, endometrial cancer), prostate cancer, salivary gland cancer (tumor), malignant lymphoma, hypophyseal tumor, peritoneal tumor, esophageal cancer, small intestinal tumor, head and neck tumor, renal cancer, thymus tumor) and the like.

The dose of the compound of the present invention varies depending on the administration subject, route of administration, target disease, symptoms, etc. For example, when it is administered orally to an adult patient, its dose is about 0.01 to 100 mg/kg body weight per dose, preferably 0.05 to 30 mg/kg body weight per dose, more preferably 0.1 to 10 mg/kg body weight per dose, which is desirably administered once to 3 times a day.

EXAMPLE

The present invention is explained in detail in the following by referring to Preparation Examples, Examples, Formulation Examples and Experimental Examples, which are merely exemplified and not to be construed as limitative, and the invention may be changed within the scope of the present invention.

Preparation Example 1

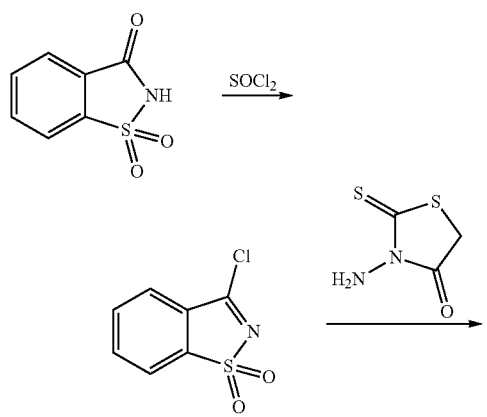

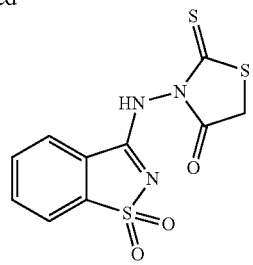

To a solution of o-sulfobenzimide (5.00 g) in dioxane (20 ml) were added thionyl chloride (7.5 ml) and dimethylformamide (0.25 ml), and the mixture was stirred overnight at 110° C. The reaction mixture was concentrated under reduced pressure, and to the residue was added toluene (20 ml) to give 3-chloro-1,2-benzisothiazole 1,1-dioxide (3.77 g) as crystals. The obtained 3-chloro-1,2-benzisothiazole 1,1-dioxide (3.77 g) was dissolved in dioxane (20 ml), 3-aminorhodanine (2.77 g) was added thereto, and the mixture was stirred at 110° C. for 1 hr. The reaction mixture was concentrated under reduced pressure, and to the residue was added chloroform (20 ml) to give 3-[(4-oxo-2-thioxothiazolidin-3-yl)amino]-1,2-benzisothiazole 1,1-dioxide (3.56 g).

Preparation Example 2

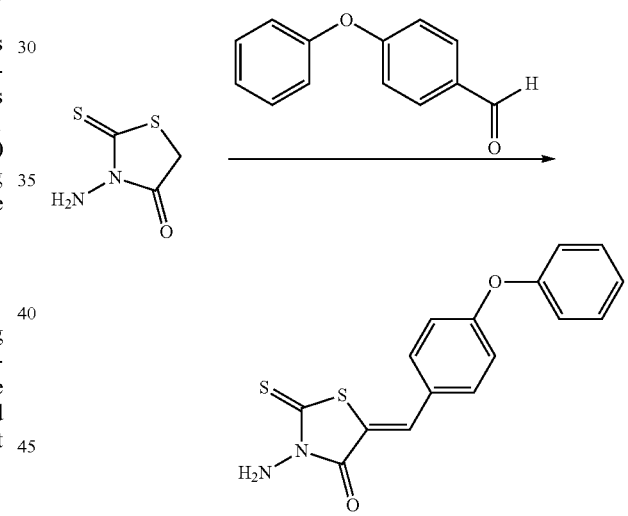

To a solution of 3-aminorhodanine (1.00 g) in ethanol (20 ml) were added 4-phenoxybenzaldehyde (1.47 g) and piperidine (57 mg), and the mixture was heated with reflux for 2 hr. The reaction mixture was concentrated under reduced pressure, and the residue was purified by silica gel column chromatography (eluent: chloroform) to give 3-amino-5-(4-phenoxybenzylidene)-2-thioxothiazolidin-4-one (1.52 g).

Preparation Example 3

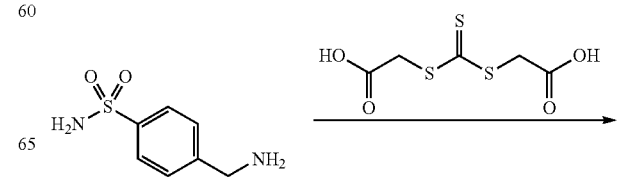

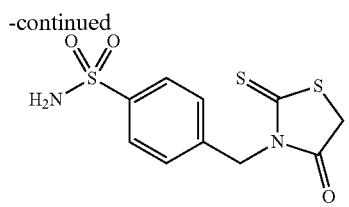

To a solution of bis(carboxymethyl)trithiocarbonate (200 mg) in tetrahydrofuran (10 ml) was added carbonyldiimidazole (291 mg), and the mixture was stirred at room temperature. After 2 hr, to the reaction mixture were added homosulfamine hydrochloride (200 mg) and N,N-diisopropylethylamine (155 mg), and the mixture was stirred overnight at 70° C. 2N Hydrochloric acid (10 ml) was added thereto under ice cooling, the mixture was extracted twice with ethyl acetate (40 ml), and the extract was dried over anhydrous sodium sulfate, and concentrated under reduced pressure. The residue was purified by silica gel column chromatography (eluent: hexane/ethyl acetate=2:1) to give 3-(4-sulfamoylbenzyl)-2-thioxothiazolidin-4-one (189 mg).

Preparation Example 4

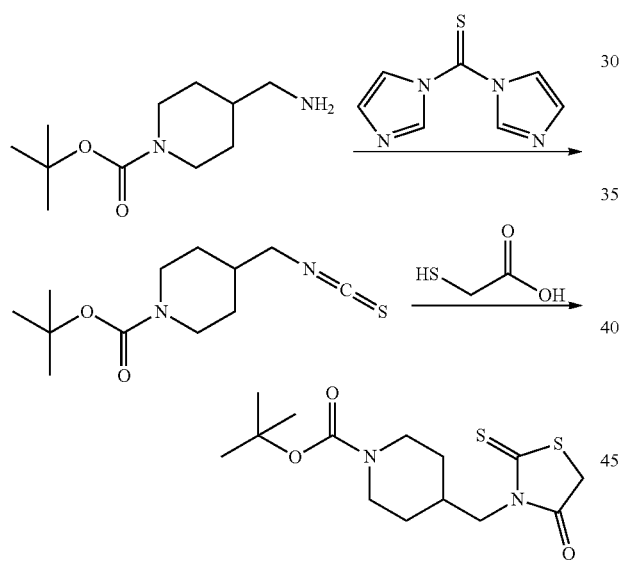

To a solution of 1-(t-butyloxycarbonyl)-4-(aminomethyl)piperidine (2.14 g) in N,N-dimethylformamide (20 ml) was added 1,1'-thiocarbonyldiimidazole (1.87 g), and the mixture was stirred at room temperature for 4 hr. The reaction mixture was poured into ice water (100 ml), and extracted with ethyl acetate (100 ml). The extract was washed successively with 0.5M hydrochloric acid, 1M aqueous sodium hydrogen carbonate solution and saturated brine, dried over anhydrous sodium sulfate, and concentrated under reduced pressure. The residue was purified by silica gel column chromatography (eluent: hexane/ethyl acetate=4/1) to give [1-(t-butyloxycarbonyl)piperidin-4-yl]methyl isothiocyanate (1.64 g).

To a solution of thioglycol acid (522 mg) in ethanol (30 ml) were added 4-N-[1-(t-butyloxycarbonyl)piperidin-4-yl]methyl isothiocyanate (1.60 g) and triethylamine (948 mg), and the mixture was stirred with heating at 80° C. for 3 hr. The reaction solution was concentrated, and the obtained residue was dissolved in ethyl acetate (50 ml). The solution was washed successively with 0.5M hydrochloric acid, 1M aqueous sodium hydrogen carbonate solution and saturated brine, dried over anhydrous sodium sulfate, and concentrated under reduced pressure to give 3-([1-(t-butyloxycarbonyl)piperidin-4-yl]methyl)-2-thioxothiazolidin-4-one (1.80 g).

Preparation Example 5

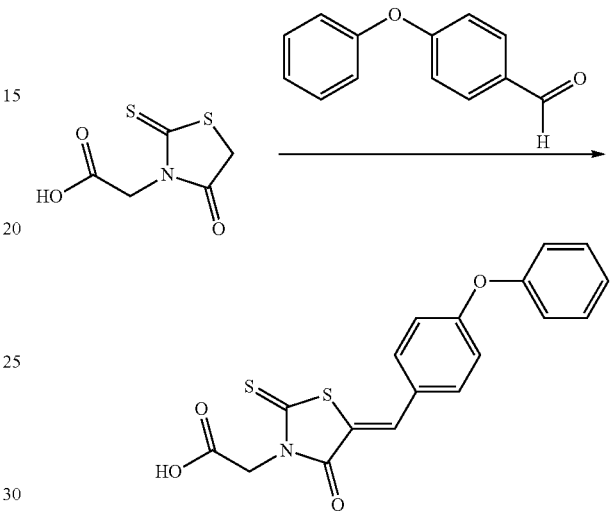

To a solution of rhodanine-3-acetic acid (1.00 g) in acetonitrile (20 ml) were added 4-phenoxybenzaldehyde (1.14) and triethylamine (1.06 g), and the mixture was heated with reflux overnight. The reaction solution was concentrated under reduced pressure, and the obtained residue was dissolved in ethyl acetate (50 ml). The solution was washed successively with 1N hydrochloric acid and saturated brine, dried over anhydrous sodium sulfate, and concentrated under reduced pressure. The residue was purified by silica gel column chromatography (eluent: chloroform/methanol=20/1) to give [4-oxo-5-(4-phenoxybenzylidene)-2-thioxo-thiazolidin-3-yl]acetic acid (1.20 g).

Preparation Example 6

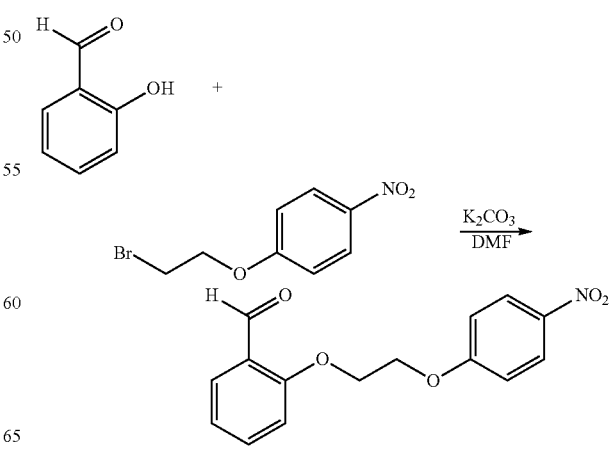

To a solution of 2-hydroxybenzaldehyde (226 mg) and 1-(2-bromoethoxy)-4-nitrobenzene (500 mg) in N,N-dimethylformaldehyde (5 mL) was added potassium carbonate (281 mg), and the mixture was stirred overnight at room temperature. The reaction mixture was poured into water (20 mL), and the mixture was extracted with ethyl acetate (20 ml). The extract was washed successively with 0.5M aqueous hydrochloric acid solution, 1M aqueous sodium hydrogen carbonate solution and saturated brine, dried over anhydrous sodium sulfate, and concentrated under reduced pressure to give 2-(2-(4-nitrophenoxy)ethoxy)benzaldehyde (560 mg).

Preparation Example 7

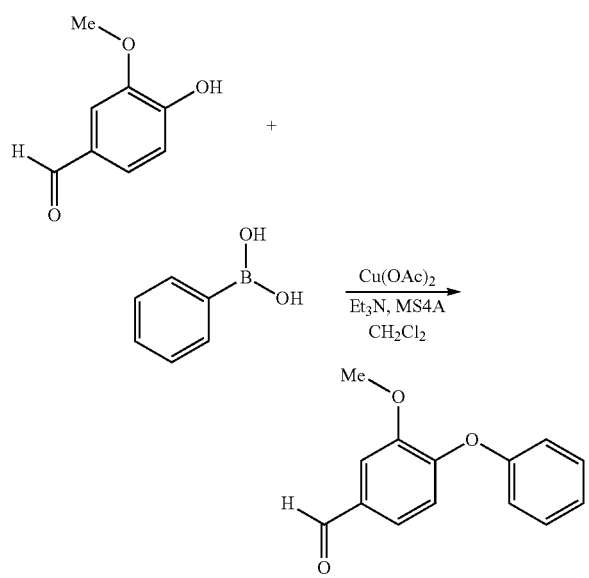

To a solution of vanillin (500 mg), phenylboronic acid (1.60 g) and copper(II) acetate (712 mg) in methylene chloride (10 mL) were added molecular sieve 4A (750 mg) and triethylamine (665 mg), and the mixture was stirred at room temperature for 2 days. The reaction solution was concentrated under reduced pressure, and the residue was dissolved in ethyl acetate (50 mL). The solution was washed successively with 0.5M aqueous hydrochloric acid solution, 1M aqueous sodium hydrogen carbonate solution and saturated brine, dried over anhydrous sodium sulfate, and concentrated under reduced pressure. The obtained residue was purified by silica gel column chromatography (hexane:ethyl acetate=10:1) to give 3-methoxy-4-phenoxybenzaldehyde (440 mg) as a yellow solid.

Example 1

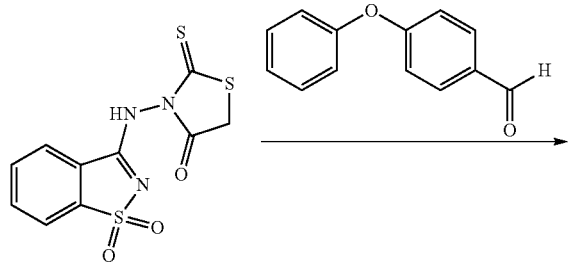

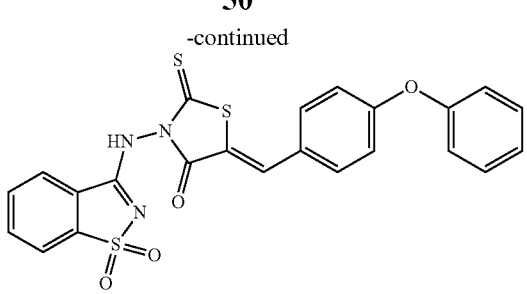

To a solution of 3-[(4-oxo-2-thioxothiazolidin-3-yl)amino]-1,2-benzisothiazole 1,1-dioxide (0.20 g) obtained in Preparation Example 1 and 4-phenoxybenzaldehyde (0.16 g) in acetonitrile (4 ml) was added triethylamine (0.26 g), and the mixture was stirred overnight at 60° C. The mixture was concentrated under reduced pressure, and the obtained residue was purified by silica gel column chromatography (chloroform:methanol=100:0→10:1) to give 3-[(4-oxo-5-(4-phenoxybenzylidene)-2-thioxothiazolidin-3-yl)amino]-1,2-benzisothiazole 1,1-dioxide (0.25 g).

Example 117

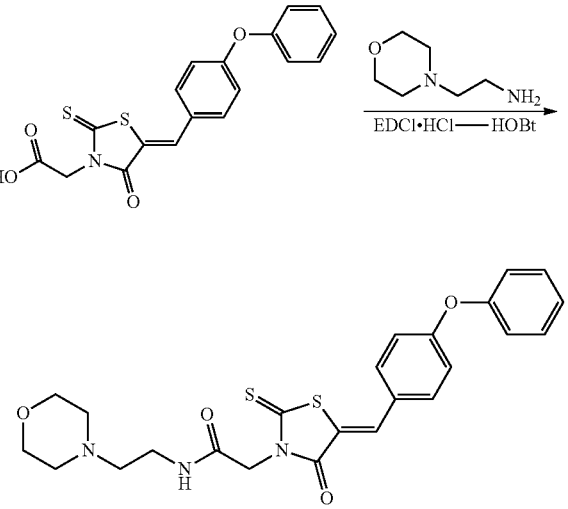

To a solution of [4-oxo-5-(4-phenoxybenzylidene)-2-thioxo-thiazolidin-3-yl]acetic acid (100 mg) obtained in Preparation Example 5 and 1-(2-aminoethyl)morpholine (39 mg) in N,N-dimethylformamide (2 mL) were added 1-hydroxybenzotriazole (HOBt) (73 mg) and 1-ethyl-3-(3-dimethylaminopropyl)carbodiimide hydrochloride (EDC HCl) (54 mg) with stirring under ice cooling, and the mixture was stirred at room temperature for 4 hr. The reaction mixture was poured into ice water (30 mL), and the mixture was extracted with ethyl acetate (30 ml). The extract was washed successively with 0.5M aqueous hydrochloric acid solution, 1M aqueous sodium hydrogen carbonate solution and saturated brine, dried over anhydrous sodium sulfate, and concentrated under reduced pressure to give 3-([N-(2-morpholino ethyl)carbamoyl]methyl)-5-(4-phenoxybenzylidene)-2-thioxothiazolidin-4-one (100 mg) as a yellow powder.

Example 79

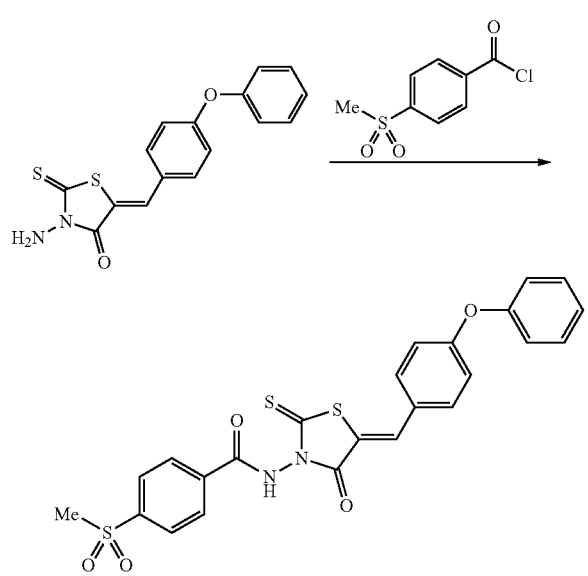

3-Amino-5-(4-phenoxybenzylidene)-2-thioxothiazolidin-4-one (295 mg) obtained in Preparation Example 2 was dissolved in toluene (4 mL), 4-(methylsulfonyl)benzoyl chloride (separately prepared from 4-methylsulfonylbenzoic acid (200 mg) and thionyl chloride (336 mg)) and triethylamine (101 mg) were added thereto, and the mixture was heated with reflux for 1 hr. The reaction mixture was allowed to be cooled to room temperature, and the resulting crystals were collected by filtration, and washed with ethanol (4 mL) to give 3-[(4-methylsulfonylphenyl)carbonylamino]-5-(4-phenoxybenzylidene)-2-thioxothiazolidin-4-one (210 mg).

Example 163

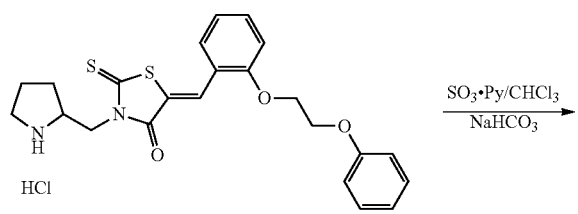

To a solution of 5-(2-(2-phenoxyethoxy)benzylidene)-3-(pyrrolidin-2-ylmethyl)-2-thioxothiazolidin-4-one (50 mg) in chloroform (4 mL) were added sulfur trioxide pyridine complex (25 mg) and triethylamine (16 mg), and the mixture was stirred at room temperature for 1 hr. Ethyl acetate (30 mL) was added thereto, and the mixture was washed with 1M aqueous hydrochloric acid solution. The organic layer was concentrated under reduced pressure, and to the obtained residue were added sodium hydrogen carbonate (8.4 mg) and water (3 mL), and then ethanol (5 mL) was added thereto to give sodium 2-((4-oxo-5-(2-(2-phenoxyethoxy)benzylidene)-2-thioxothiazolidin-3-yl)methyl)pyrrolidine-1-sulfonate (53 mg).

The following compounds were produced using each corresponding raw material compound according to the method described in Example 1, 117, 79 or 163 and a method known per se (e.g., de-Boc reaction). The corresponding raw material compounds were commercially available products, or were produced according to a method known per se or the methods described in Preparation Examples 1-7. The structure formulas of the compounds are shown in Table 1, and the physicochemical data are shown in Table 2.

$R^1$ means —Y-A and $R^2$ means —Z—B in the tables.

The following abbreviations are used in the tables.

Pre: the raw material compound (the number of Preparation Example) which was used for the objective compound, and the number of Example that the objective compound was produced according to.

Ex: the number of Example

TABLE 1

List of Compound of Examples

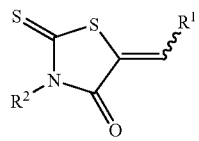

| Ex | $R^1$— | $R^2$— |
|---|---|---|
| 1 | ![4-phenoxyphenyl with methyl] | ![benzisothiazole-3-ylamino dioxide] |

TABLE 1-continued

List of Compound of Examples

| Ex | R¹— | R²— |
|----|-----|-----|
| 2 | 4-carboxyphenyl-methyl (4-HOOC-C₆H₄-CH=) | benzo[d]isothiazol-3-ylamino 1,1-dioxide |
| 3 | 4-(morpholine-4-carbonyl)phenyl-methyl | benzo[d]isothiazol-3-ylamino 1,1-dioxide |
| 4 | 4-methoxyphenyl-methyl | benzo[d]isothiazol-3-ylamino 1,1-dioxide |
| 5 | 3-bromophenyl-methyl | benzo[d]isothiazol-3-ylamino 1,1-dioxide |
| 6 | 4-bromophenyl-methyl | benzo[d]isothiazol-3-ylamino 1,1-dioxide |
| 7 | 2,4-dinitrophenyl-methyl | benzo[d]isothiazol-3-ylamino 1,1-dioxide |
| 8 | 4-(pyridin-4-yl)phenyl-methyl | benzo[d]isothiazol-3-ylamino 1,1-dioxide |

TABLE 1-continued
List of Compound of Examples
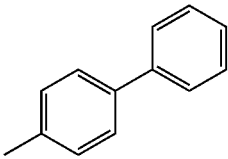
| Ex | R¹— | R²— |
|---|---|---|
| 9 | 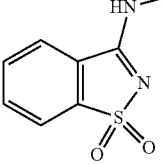 | 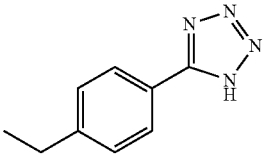 |
| 10 | 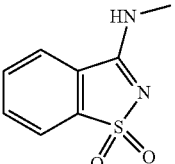 | 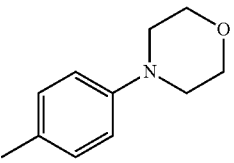 |
| 11 | 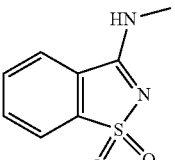 | 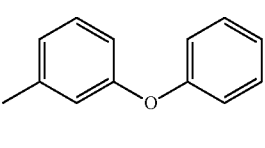 |
| 12 | 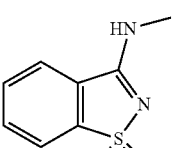 | 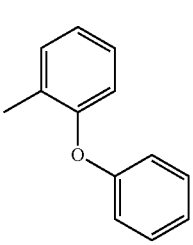 |
| 13 | 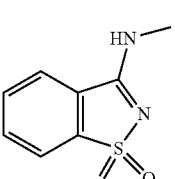 | 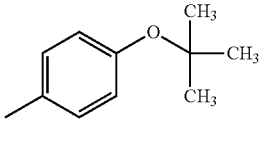 |
| 14 | 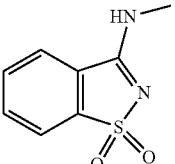 | 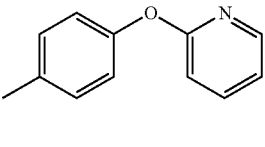 |
| 15 | 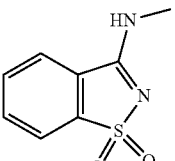 | |

TABLE 1-continued
List of Compound of Examples
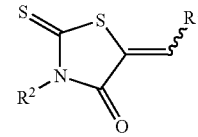
| Ex | R¹— | R²— |
|---|---|---|
| 16 | 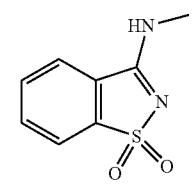 | 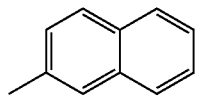 |
| 17 | 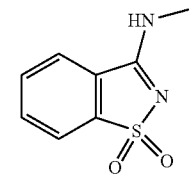 | 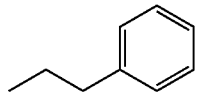 |
| 18 | 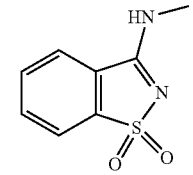 | 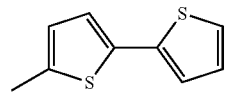 |
| 19 | 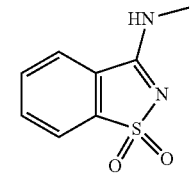 | 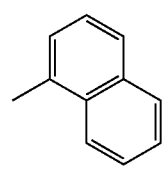 |
| 20 | 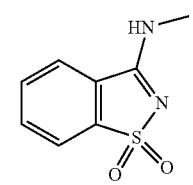 | 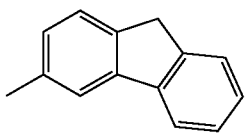 |
| 21 | 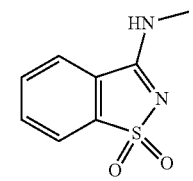 | 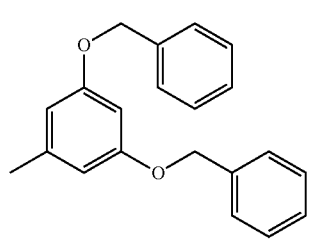 |
| 22 | 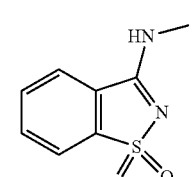 | |

TABLE 1-continued

List of Compound of Examples

| Ex | R¹— | R²— |
|----|-----|-----|
| 23 | 9-ethyl-3-methylcarbazol-6-yl | 3-amino-1,2-benzisothiazole 1,1-dioxide |
| 24 | 4-methyl-N,N-diphenylaniline | 3-amino-1,2-benzisothiazole 1,1-dioxide |
| 25 | 4-methylstilbene | 3-amino-1,2-benzisothiazole 1,1-dioxide |
| 26 | 5-methyl-2-(4-nitrophenyl)furan | 3-amino-1,2-benzisothiazole 1,1-dioxide |
| 27 | 4-methylphenyl butyl ether | 3-amino-1,2-benzisothiazole 1,1-dioxide |
| 28 | n-nonyl | 3-amino-1,2-benzisothiazole 1,1-dioxide |
| 29 | non-2-enyl | 3-amino-1,2-benzisothiazole 1,1-dioxide |

TABLE 1-continued
List of Compound of Examples
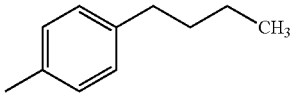
| Ex | R¹— | R²— |
|---|---|---|
| 30 | 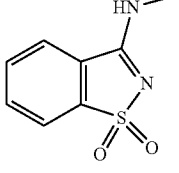 | 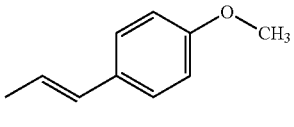 |
| 31 | 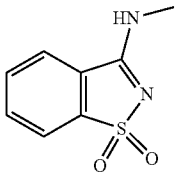 | 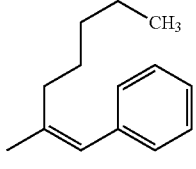 |
| 32 | 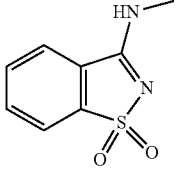 | 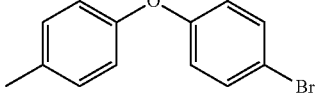 |
| 33 | 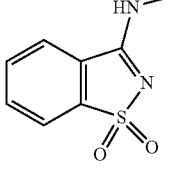 | 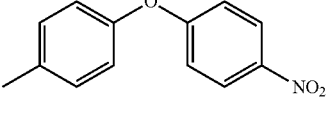 |
| 34 | 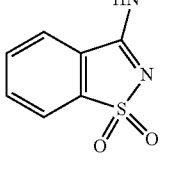 | 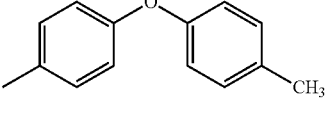 |
| 35 | 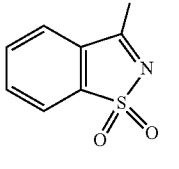 | 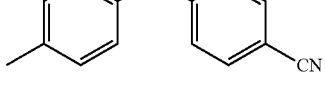 |
| 36 | 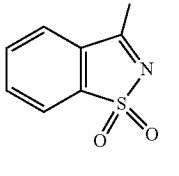 | |

TABLE 1-continued
List of Compound of Examples
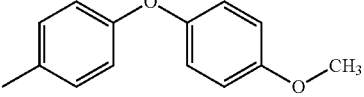
| Ex | R$^1$— | R$^2$— |
|---|---|---|
| 37 | 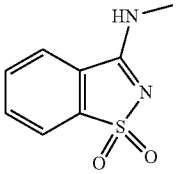 | 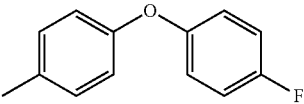 |
| 38 | 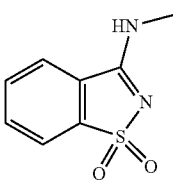 | 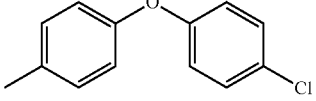 |
| 39 | 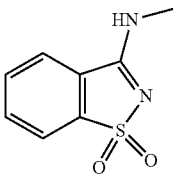 | 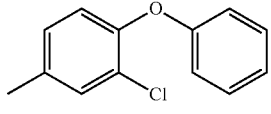 |
| 40 | 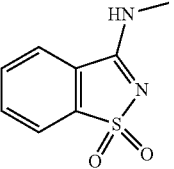 | 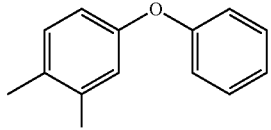 |
| 41 | 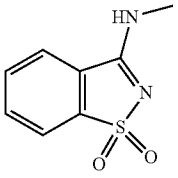 | 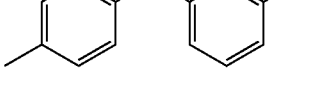 |
| 42 | 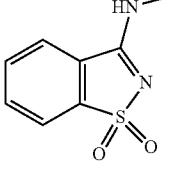 | 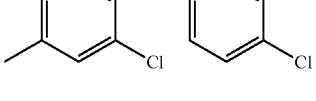 |
| 43 | 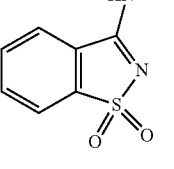 | |

TABLE 1-continued
List of Compound of Examples
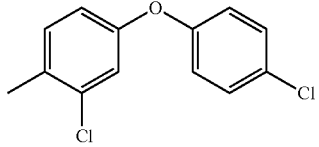 [SMILES: Cc1ccc(Oc2ccc(Cl)cc2)cc1Cl]
| Ex | R¹— | R²— |
|---|---|---|
| 44 | 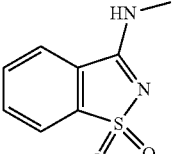 | 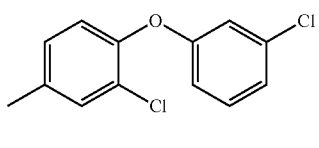 |
| 45 | 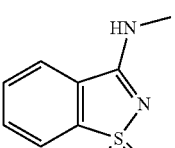 | 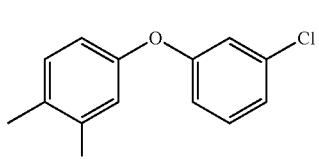 |
| 46 | 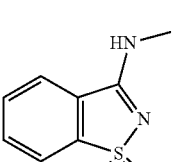 | 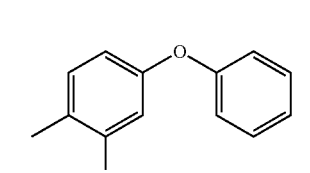 |
| 47 | 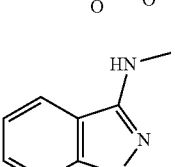 | 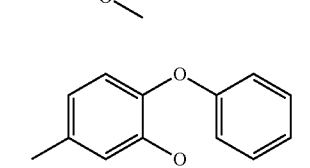 |
| 48 | 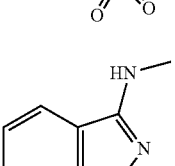 | 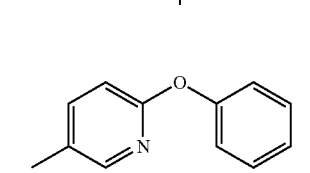 |
| 49 | 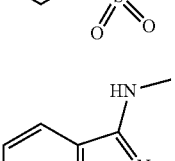 | 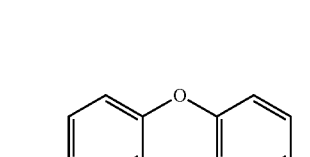 |
| 50 | 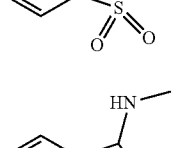 | |

TABLE 1-continued

List of Compound of Examples

| Ex | R¹— | R²— |
|----|-----|-----|
| 51 | 3-methylphenyl-O-CH₂CH₂-O-phenyl | 3-aminobenzo[d]isothiazole 1,1-dioxide (N-methyl) |
| 52 | 4-methylphenyl-O-CH₂CH₂-O-phenyl | 3-aminobenzo[d]isothiazole 1,1-dioxide (N-methyl) |
| 53 | 2-methylphenyl-O-CH₂CH₂-O-phenyl | 3-aminobenzo[d]isothiazole 1,1-dioxide (N-methyl) |
| 54 | 2-methylphenyl-O-CH₂CH₂-O-(4-fluorophenyl) | 3-aminobenzo[d]isothiazole 1,1-dioxide (N-methyl) |
| 55 | 2-methylphenyl-O-CH₂CH₂-O-(4-methylphenyl) | 3-aminobenzo[d]isothiazole 1,1-dioxide (N-methyl) |
| 56 | 2-methylphenyl-O-CH₂CH₂-O-(4-nitrophenyl) | 3-aminobenzo[d]isothiazole 1,1-dioxide (N-methyl) |
| 57 | 2-methylphenyl-O-CH₂CH₂CH₂-O-phenyl | 3-aminobenzo[d]isothiazole 1,1-dioxide (N-methyl) |

TABLE 1-continued

List of Compound of Examples

| Ex | R¹— | R²— |
|---|---|---|
| 58 | (2-methylphenoxy)methyl-2,3-dihydro-1,4-benzodioxine | 3-(methylamino)-1,2-benzisothiazole 1,1-dioxide |
| 59 | 3-chloro-2-methylphenoxy ethoxy phenyl | 3-(methylamino)-1,2-benzisothiazole 1,1-dioxide |
| 60 | 2,6-dimethylphenoxy ethoxy phenyl | 3-(methylamino)-1,2-benzisothiazole 1,1-dioxide |
| 61 | 4-methoxy-2-methylphenoxy ethoxy phenyl | 3-(methylamino)-1,2-benzisothiazole 1,1-dioxide |
| 62 | 5-bromo-2-methylphenoxy ethoxy phenyl | 3-(methylamino)-1,2-benzisothiazole 1,1-dioxide |
| 63 | 2-chloro-6-methylphenoxy ethoxy phenyl | 3-(methylamino)-1,2-benzisothiazole 1,1-dioxide |
| 64 | 4-chloro-2-methylphenoxy ethoxy phenyl | 3-(methylamino)-1,2-benzisothiazole 1,1-dioxide |

TABLE 1-continued
List of Compound of Examples
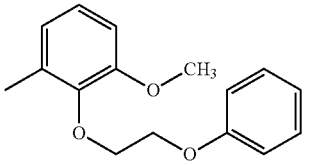 [SMILES: COc1cccc(C)c1OCCOc1ccccc1]
| Ex | R¹— | R²— |
|---|---|---|
| 65 | 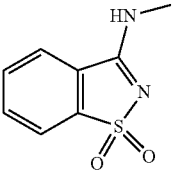 | 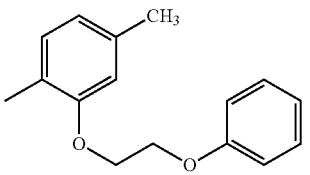 |
| 66 | 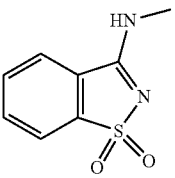 | 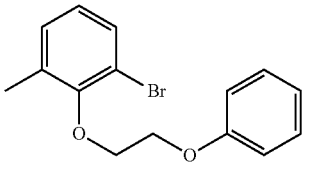 |
| 67 | 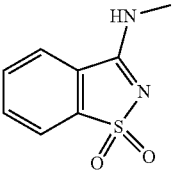 | 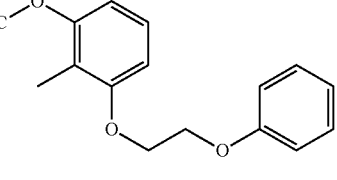 |
| 68 | 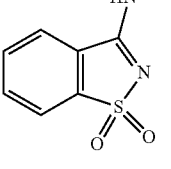 | 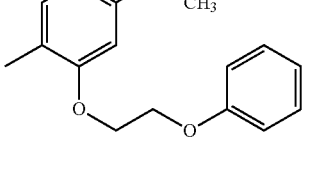 |
| 69 | 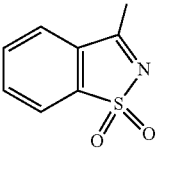 | 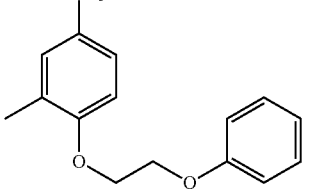 |
| 70 | 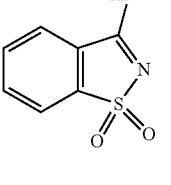 | 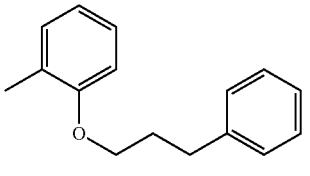 |
| 71 | 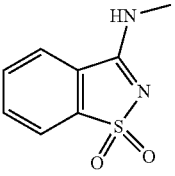 | |

TABLE 1-continued

List of Compound of Examples

| Ex | R¹— | R²— |
|----|-----|-----|
| 72 | 4-benzylphenyl | 3-(benzo[d]isothiazol-3-yl 1,1-dioxide)amino |
| 73 | 4-(1-propenyl)phenoxyphenyl | 3-(benzo[d]isothiazol-3-yl 1,1-dioxide)amino |
| 74 | 4-methyl-1-phenoxynaphthyl | 3-(benzo[d]isothiazol-3-yl 1,1-dioxide)amino |
| 75 | 6-methyl-2-phenoxynaphthyl | 3-(benzo[d]isothiazol-3-yl 1,1-dioxide)amino |
| 76 | 4-phenoxy-tolyl | $H_2N-$ |
| 77 | 4-phenoxy-tolyl | benzamido |
| 78 | 4-phenoxy-tolyl | 4-methoxybenzamido |
| 79 | 4-phenoxy-tolyl | 4-(methylsulfonyl)benzamido |

TABLE 1-continued

List of Compound of Examples

| Ex | R¹— | R²— |
|---|---|---|
| 80 | 4-methylphenyl-O-phenyl | 3-methoxy-N-methylbenzamide |
| 81 | 4-methylphenyl-O-phenyl | 4-(methylthio)-N-methylbenzamide |
| 82 | 4-methylphenyl-O-phenyl | 2,4-dinitro-N-methylbenzamide |
| 83 | 4-methylphenyl-O-phenyl | 2-(methylsulfonyl)-N-methylbenzamide |
| 84 | 4-methylphenyl-O-phenyl | N-propylbenzenesulfonamide |
| 85 | 4-methylphenyl-O-phenyl | 4-(3-propyl)morpholine |
| 86 | 4-methylphenyl-O-phenyl | 4-(3-propyl)thiomorpholine 1,1-dioxide |
| 87 | 4-methylphenyl-O-phenyl | 1-benzyl-4-methylpiperidine |
| 88 | 4-methylphenyl-O-phenyl | 4-(3-propyl)morpholine · HCl |

TABLE 1-continued

List of Compound of Examples

| Ex | R¹— | R²— |
|---|---|---|
| 89 | 4-methylphenyl-O-phenyl | tert-butoxycarbonyl-(4-ethylpiperidin-1-yl) |
| 90 | 4-methylphenyl-O-phenyl | 4-ethylpiperidine · HCl |
| 91 | 4-methylphenyl-O-phenyl | 1-(methylsulfonyl)-4-ethylpiperidine |
| 92 | 4-methylphenyl-O-phenyl | 1-(methoxyacetyl)-4-ethylpiperidine |
| 93 | 4-methylphenyl-O-phenyl | tert-butoxycarbonyl-(3-ethylpiperidin-1-yl) |
| 94 | 4-methylphenyl-O-phenyl | 3-ethylpiperidine · HCl |
| 95 | 4-methylphenyl-O-phenyl | 1-(methylsulfonyl)-3-ethylpiperidine |
| 96 | 4-methylphenyl-O-phenyl | tert-butoxycarbonyl-(2-ethylpyrrolidin-1-yl) |
| 97 | 4-methylphenyl-O-phenyl | 2-ethylpyrrolidine · HCl |

TABLE 1-continued

List of Compound of Examples

| Ex | R¹— | R²— |
|---|---|---|
| 98 | 4-methylphenyl-O-phenyl | 2-ethyl-1-(methylsulfonyl)pyrrolidine |
| 99 | 4-methylphenyl-O-phenyl | tert-butyl 4-methylpiperidine-1-carboxylate |
| 100 | 4-methylphenyl-O-phenyl | 4-methylpiperidine · HCl |
| 101 | 4-methylphenyl-O-phenyl | 2-ethylpiperidine · HCl |
| 102 | 4-methylphenyl-O-phenyl | N-ethylpropylamine · HCl |
| 103 | 4-methylphenyl-O-phenyl | sodium propylsulfamate |
| 104 | 4-methylphenyl-O-phenyl | 6-methyl-4-(propylamino)-2H-1,2,3-oxathiazine 2,2-dioxide |
| 105 | 4-methylphenyl-O-phenyl | sodium 3-ethylpiperidine-1-sulfonate |
| 106 | 4-methylphenyl-O-phenyl | sodium 4-ethylpiperidine-1-sulfonate |

TABLE 1-continued

List of Compound of Examples

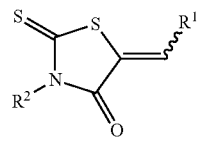

| Ex | R¹— | R²— |
|---|---|---|
| 107 | 4-methylphenoxyphenyl | 2-ethylpyrrolidine-1-sulfonic acid |
| 108 | 4-methylphenoxyphenyl | propanoic acid |
| 109 | 4-methylphenoxyphenyl | N-(4-sulfamoylphenyl)propanamide |
| 110 | 4-methylphenoxyphenyl | N-(4-sulfamoylbenzyl)propanamide |
| 111 | 4-methylphenoxyphenyl | 1-(piperidin-1-yl)propan-1-one |
| 112 | 4-methylphenoxyphenyl | 1-(morpholin-4-yl)propan-1-one |
| 113 | 4-methylphenoxyphenyl | 1-(3,4-dihydroisoquinolin-2(1H)-yl)propan-1-one |
| 114 | 4-methylphenoxyphenyl | N,N-dimethylpropanamide |

TABLE 1-continued

List of Compound of Examples

| Ex | R¹— | R²— |
|---|---|---|
| 115 | 4-(phenoxy)phenyl | 1-(4-methylpiperazin-1-yl)propan-1-one-3-yl |
| 116 | 4-(phenoxy)phenyl | N-(2,3-dihydroxypropyl)propanamide-3-yl |
| 117 | 4-(phenoxy)phenyl | N-(2-morpholinoethyl)propanamide-3-yl |
| 118 | 4-(phenoxy)phenyl | methyl N-propanoylglycinate-3-yl |
| 119 | 4-(phenoxy)phenyl | methyl 1-propanoylpyrrolidine-2-carboxylate-3-yl |
| 120 | 4-(phenoxy)phenyl | N-(3-hydroxypropyl)propanamide-3-yl |
| 121 | 4-(phenoxy)phenyl | N-(4-hydroxybutyl)propanamide-3-yl |
| 122 | 4-(phenoxy)phenyl | 1-((R)-3-hydroxypyrrolidin-1-yl)propan-1-one-3-yl |
| 123 | 4-(phenoxy)phenyl | N-(2-(1,1-dioxidothiomorpholino)ethyl)propanamide-3-yl |

TABLE 1-continued

List of Compound of Examples

| Ex | R¹— | R²— |
|---|---|---|
| 124 | 4-methylphenoxyphenyl | 1-hydroxycyclohexyl-CH₂-NH-C(O)-CH₂CH₃ |
| 125 | 4-methylphenoxyphenyl | 4-methylphenyl-SO₂-NH-C(O)-CH₂CH₃ |
| 126 | 4-methylphenoxyphenyl | H₃C-SO₂-NH-C(O)-CH₂CH₃ |
| 127 | 4-methylphenoxyphenyl | NaOOC-CH(CH₃)-CH₂-CH(CH₃)₂ |
| 128 | 4-methylphenoxyphenyl | 4-(H₂N-SO₂)phenyl-CH₂CH₂- |
| 129 | 4-methylphenoxyphenyl | phenyl-CH₂- |
| 130 | 4-methylphenoxyphenyl | phenyl-CH₂CH₂- |
| 131 | 4-methylphenoxyphenyl | benzo[1,3]dioxol-5-yl-CH₂- |
| 132 | 4-methylphenoxyphenyl | 1H-indol-3-yl-CH₂CH₂- |
| 133 | 4-methylphenoxyphenyl | cyclohexyl-CH₂- |

TABLE 1-continued

List of Compound of Examples

| Ex | R¹— | R²— |
|---|---|---|
| 134 | 4-methylphenoxyphenyl | 3-propyltetrahydrofuran |
| 135 | 4-methylphenoxyphenyl | 4-methoxybutyl |
| 136 | 4-methylphenoxyphenyl | 3-hydroxypropyl |
| 137 | 4-methylphenoxyphenyl | 4-hydroxybutyl |
| 138 | 4-methylphenoxyphenyl | 5-hydroxypentyl |
| 139 | 4-methylphenoxyphenyl | (1-hydroxycyclohexyl)ethyl |
| 140 | 4-methylphenoxyphenyl | benzyl |
| 141 | 4-methylphenoxyphenyl | 4-hydroxybenzyl |
| 142 | 4-methylphenoxyphenyl | 4-carboxybenzyl |
| 143 | 4-methylphenoxyphenyl | 4-sulfobenzyl |
| 144 | 4-methylphenoxyphenyl | 2-(pyridin-4-yl)ethyl |

TABLE 1-continued

List of Compound of Examples

| Ex | R¹— | R²— |
|---|---|---|
| 145 | 4-methylphenyl phenyl ether | methyl 4-ethylbenzoate |
| 146 | 4-methylphenyl phenyl ether | 4-ethylbenzoic acid |
| 147 | 4-methylphenyl phenyl ether | 4-methylbenzenesulfonamide (ethyl linker) |
| 148 | 4-methylphenyl phenyl ether | 3-methylbenzenesulfonamide (ethyl linker) |
| 149 | 4-methylphenyl phenyl ether | sodium ethanesulfonate |
| 150 | 4-methylphenyl phenyl ether | sodium propyl sulfate |
| 151 | 4-methylphenyl phenyl ether | trans-4-ethylcyclohexanecarboxylic acid |
| 152 | 2-methylphenoxyethyl phenyl ether | tert-butyl 4-ethylpiperidine-1-carboxylate |
| 153 | 2-methylphenoxyethyl phenyl ether | 4-ethylpiperidine·HCl |

TABLE 1-continued

List of Compound of Examples

| Ex | R¹— | R²— |
|---|---|---|
| 154 | 2-methylphenyl-O-CH₂CH₂-O-phenyl | H₃C-O-CH₂-C(O)-N(4-ethylpiperidine) |
| 155 | 2-methylphenyl-O-CH₂CH₂-O-phenyl | (CH₃)₃C-O-C(O)-N(2-ethylpyrrolidine) |
| 156 | 2-methylphenyl-O-CH₂CH₂-O-phenyl | 2-ethylpyrrolidine·HCl |
| 157 | 2-methylphenyl-O-CH₂CH₂-O-phenyl | phenyl-CH₂CH₂- |
| 158 | 2-methylphenyl-O-CH₂CH₂-O-phenyl | H₂N-CH₂CH₂CH₃ · HCl |
| 159 | 2-methylphenyl-O-CH₂CH₂-O-phenyl | 4-(methylsulfonyl)-C₆H₄-C(O)NH-propyl |
| 160 | 2-methylphenyl-O-CH₂CH₂-O-phenyl | HO-C(O)-CH₂CH₃ |

TABLE 1-continued

List of Compound of Examples

| Ex | R¹— | R²— |
|---|---|---|
| 161 | (2-methylphenoxy)ethoxy-phenyl | methyl prolinate N-propanoyl |
| 162 | (2-methylphenoxy)ethoxy-phenyl | 2-ethyl-1-(methylsulfonyl)pyrrolidine |
| 163 | (2-methylphenoxy)ethoxy-phenyl | sodium 2-ethylpyrrolidine-1-sulfonate |
| 164 | (2-methylphenoxy)ethoxy-phenyl | 4-ethylbenzenesulfonamide |
| 165 | (2-methylphenoxy)ethoxy-phenyl | 1-propanoylpyrrolidine-2-carboxylic acid |

TABLE 2

| Ex | Pre | ¹H-NMR (DMSO-$d_6$): δ (ppm) | MS(ESI+) |
|---|---|---|---|
| 1 | Pre. Ex. 1<br>Ex. 1 | 8.27-8.25 (m, 1H), 8.10-8.08 (m, 1H), 8.01 (s, 1H), 7.95-7.93 (m, 2H), 7.77 (d, J = 7.2 Hz, 2H), 7.49 (dd, J = 8.4, 7.6 Hz, 2H), 7.28 (dd, J = 7.6, 7.2 Hz, 1H), 7.16 (dd, J = 8.8, 8.0 Hz, 4H) | 494 |
| 2 | Pre. Ex. 1<br>Ex. 1 | 8.08 (d, J = 8.4 Hz, 2H), 7.87 (dd, J = 6.8, 3.2 Hz, 1H), 7.79 (s, 1H), 7.71-7.69 (m, 3H) 7.66-7.64 (m, 2H) | 446 |
| 3 | Ex. 2, 117 | 8.20 (s, 1H), 8.02 (s, 2H), 7.89 (dd, J = 5.2, 2.8 Hz, 2H), 7.79 (d, J = 8.4 Hz, 2H), 7.60 (dd, J = 9.6, 8.0 Hz, 2H), 3.64-3.23 (m, 8H) | 515 |
| 4 | Pre. Ex. 1<br>Ex. 1 | 8.08 (s, 1H), 7.91 (s, 1H), 7.86 (s, 1H), 7.82-7.80 (m, 2H), 7.74 (d, J = 8.8 Hz, 2H), 7.16 (d, J = 9.2 Hz, 2H) | 432 |
| 5 | Pre. Ex. 1<br>Ex. 1 | 8.04 (br, 1H), 7.93 (s, 1H), 7.87 (s, 1H), 7.87 (s, 2H), 7.78-7.72 (m, 3H), 7.67 (d, J = 7.6 Hz, 1H), 7.54 (dd, J = 8.0, 7.6 Hz, 1H) | 482 |
| 6 | Pre. Ex. 1<br>Ex. 1 | 8.10-8.08 (m, 1H), 7.92-7.91 (m, 1H), 7.89 (s, 1H), 7.82-7.78 (m, 4H), 7.65 (d, J = 7.6 Hz, 2H) | 480 |

TABLE 2-continued

| Ex | Pre | ¹H-NMR (DMSO-d₆): δ (ppm) | MS(ESI+) |
|---|---|---|---|
| 7 | Pre. Ex. 1 Ex. 1 | 8.89 (d, J = 2.0 Hz, 1H), 8.68 (dd, J = 8.4, 6.4 Hz, 1H), 8.17 (s, 1H), 8.14 (d, J = 8.4 Hz, 1H), 8.13-8.10 (m, 1H), 7.94-7.92 (m, 1H), 7.83-7.81 (m, 2H) | 492 |
| 8 | Pre. Ex. 1 Ex. 1 | 8.74 (d, J = 6.0 Hz, 2H), 8.07-8.04 (m, 2H), 8.01-7.99 (m, 1H), 7.91 (d, J = 4.4 Hz, 3H), 7.86-7.84 (m, 3H), 7.75-7.73 (m, 2H) | 479 |
| 9 | Pre. Ex. 1 Ex. 1 | 8.12 (br, 1H), 7.97-7.90 (m, 4H), 7.82-7.78 (m, 6H), 7.52 (dd, J = 8.0, 7.2 Hz, 2H), 7.44 (dd, J = 9.2, 7.2 Hz, 1H) | 478 |
| 10 | Pre. Ex. 1 Ex. 1 | 8.24 (d, J = 8.0 Hz, 3H), 8.07 (s, 2H), 7.96 (d, J = 8.4 Hz, 2H), 7.93 (dd, J = 5.6, 3.2 Hz, 2H) | 470 |
| 11 | Pre. Ex. 1 Ex. 1 | 8.22 (br, 1H), 8.07-8.05 (m, 1H), 7.93-7.93 (m, 2H), 7.87 (s, 1H), 7.73 (d, J = 4.4 Hz, 2H), 7.59 (d, J = 9.2 Hz, 2H)7.12 (d, J = 9.2 Hz, 2H), 7.07 (d, J = 9.2 Hz, 2H), 3.74 (d, J = 4.8 Hz, 6H) | 487 |
| 12 | Pre. Ex. 1 Ex. 1 | 7.86-7.85 (m, 1H), 7.77 (s, 1H), 7.71-7.69 (m, 1H), 7.65-7.63 (m, 2H), 7.57 (dd, J = 8.0, 7.6 Hz, 1H), 7.45 (dd, J = 14.4, 7.6 Hz, 3H), 7.26 (s, 1H), 7.22 (dd, J = 7.6, 7.2 Hz, 1H), 7.15-7.11 (m, 3H) | 494 |
| 13 | Pre. Ex. 1 Ex. 1 | 8.24-8.22 (m, 1H), 8.09 (s, 1H), 8.08-8.04 (m, 1H), 7.92-7.90 (m, 2H), 7.72 (d, J = 7.6 Hz, 1H), 7.55 (dd, J = 8.0, 7.6 Hz, 1H), 7.47 (dd, J = 8.0, 7.6 Hz, 2H), 7.35 (dd, J = 7.6, 7.6 Hz, 1H), 7.25 (dd, J = 7.6, 7.2 Hz, 1H), 7.16 (d, J = 7.6 Hz, 2H), 6.92 (d, J = 8.4 Hz, 1H) | 494 |
| 14 | Pre. Ex. 1 Ex. 1 | 7.88-7.86 (m, 1H), 7.72 (s, 1H), 7.71-7.70 (m, 1H), 7.65 (dd, J = 5.6, 3.2 Hz, 2H), 7.60 (d, J = 4.4 Hz, 2H), 7.16 (d, J = 7.2 Hz, 2H), 1.40 (s, 9H) | 474 |
| 15 | Pre. Ex. 1 Ex. 1 | 8.23-8.22 (m, 1H), 8.07 (br, 1H), 7.07 (d, J = 2.8 Hz, 1H), 7.92-7.90 (m, 2H), 7.81-7.79 (m, 2H), 7.76 (d, J = 8.4 Hz, 2H), 7.33 (d, J = 9.6 Hz, 2H), 7.23-7.20 (m, 1H), 7.16 (d, J = 8.0 Hz, 1H) | 495 |
| 16 | Pre. Ex. 1 Ex. 1 | 8.16 (br, 1H), 7.99 (br, 1H), 7.92 (s, 1H), 7.92-7.87 (m, 2H), 7.70 (d, J = 4.4 Hz, 2H), 7.49 (d, J = 7.2 Hz, 2H), 7.42 (dd, J = 7.2, 7.2 Hz, 2H), 7.37 (d, J = 7.2 Hz, 1H), 7.24 (d, J = 8.8 Hz, 2H), 5.23 (s, 2H) | 508 |
| 17 | Pre. Ex. 1 Ex. 1 | 8.27 (s, 1H), 8.11-8.07 (m, 2H), 8.00 (d, J = 1.6 Hz, 1H), 7.91 (s, 1H), 7.89 (dd, J = 6.0, 3.2 Hz, 1H), 7.76 (dd, J = 8.8, 1.6 Hz, 1H), 7.73-7.71 (m, 1H), 7.67-7.64 (m, 4H) | 452 |
| 18 | Pre. Ex. 1 Ex. 1 | 8.12 (s, 1H), 7.98 (s, 1H), 7.86 (s, 2H), 7.34-7.27 (m, 4H), 7.21 (dd, J = 4.4, 2.4 Hz, 1H), 7.12 (dd, J = 7.2, 6.8 Hz, 1H), 2.89 (t, J = 8.8 Hz, 2H), 2.67-2.64 (m, 2H) | 430 |
| 19 | Pre. Ex. 1 Ex. 1 | 8.04 (s, 1H), 7.92-7.90 (m, 1H), 7.74 (d, J = 4.4 Hz, 2H), 7.70-7.66 (m, 3H), 7.59 (dd, J = 3.6, 1.2 Hz, 1H), 7.53 (d, J = 4.0 Hz, 1H), 7.18 (dd, J = 5.2, 3.6 Hz, 1H) | 490 |
| 20 | Pre. Ex. 1 Ex. 1 | 8.64 (s, 1H), 8.31 (s, 1H), 8.22 (d, J = 7.6 Hz, 1H), 8.15-8.13 (m, 2H), 8.05 (d, J = 7.2 Hz, 1H), 7.95 (s, 2H), 7.81 (d, J = 7.6 Hz, 1H), 7.68 (d, J = 7.6 Hz, 3H) | 452 |
| 21 | Pre. Ex. 1 Ex. 1 | 8.10 (d, J = 8.0 Hz, 1H), 8.01 (d, J = 6.4 Hz, 1H), 7.88-7.87 (m, 2H), 7.85 (s, 1H), 7.73-7.70 (m, 2H), 7.66-7.64 (m, 3H), 7.46-7.38 (m, 2H), 4.06 (s, 2H) | 490 |
| 22 | Pre. Ex. 1 Ex. 1 | 7.96 (br, 1H), 7.79 (br, 1H), 7.73 (br, 3H), 7.48 (d, J = 7.2 Hz, 4H), 7.41 (dd, J = 8.4, 7.2 Hz, 4H), 7.36 (d, J = 7.2 Hz, 2H), 6.90 (s, 2H), 6.85 (s, 1H), 5.18 (s, 4H) | 614 |
| 23 | Pre. Ex. 1 Ex. 1 | 8.55 (s, 1H), 8.32 (d, J = 8.0 Hz, 1H), 8.22 (s, 1H), 8.15 (s, 1H), 8.04 (s, 1H), 7.91 (s, 2H), 7.72 (d, J = 8.4 Hz, 2H), 7.56 (dd, J = 8.0, 7.6 Hz, 1H), 7.32 (dd, J = 7.6, 7.6 Hz, 1H), 4.53 (d, J = 6.8 Hz, 2H), 1.35 (t, J = 7.2 Hz, 3H) | 519 |
| 24 | Pre. Ex. 1 Ex. 1 | 8.20-8.18 (m, 1H), 8.04-8.02 (m, 1H), 7.91-7.90 (m, 2H), 7.84 (s, 1H), 7.58 (d, J = 8.8 Hz, 2H), 7.43 (t, J = 8.0 Hz, 4H), 7.26-7.21 (m, 6H), 6.93 (d, J = 8.8 Hz, 2H) | 569 |
| 25 | Pre. Ex. 1 Ex. 1 | 7.97 (br, 1H), 7.81 (d, J = 8.4 Hz, 4H), 7.71-7.66 (m, 6H), 7.48-7.37 (m, 4H), 7.32 (d, J = 6.0 Hz, 1H) | 504 |
| 26 | Pre. Ex. 1 Ex. 1 | 8.65 (s, 1H), 8.27 (dd, J = 8.8, 8.8 Hz, 2H), 7.91-7.87 (m, 2H), 7.71-7.71 (m, 1H), 7.66-7.62 (m, 4H), 7.37 (d, J = 4.0 Hz, 1H) | 513 |
| 27 | Pre. Ex. 1 Ex. 1 | 8.11 (s, 1H), 7.94 (s, 1H), 7.88 (s, 1H), 7.83 (s, 2H), 7.67 (d, J = 8.8 Hz, 2H), 7.15 (d, J = 8.8 Hz, 2H), 4.09 (t, J = 6.4 Hz, 2H), 1.75-1.71 (m, 2H), 1.48-1.42 (m, 2H), 0.93 (t, J = 7.6 Hz, 3H) | 474 |
| 28 | Pre. Ex. 1 Ex. 1 | 8.13 (d, J = 2.8 Hz, 1H), 7.98 (d, J = 5.2 Hz, 1H), 7.86 (dd, J = 5.6, 3.2 Hz, 2H), 7.13 (dd, J = 8.0, 7.6 Hz, 1H), 3.13-3.07 (m, 2H), 2.31 (q, J = 7.6 Hz, 2H), 1.56 (t, J = 7.2 Hz, 2H), 1.17 (t, J = 7.2 Hz, 4H), 0.87 (t, J = 6.8 Hz, 5H) | 424 |

TABLE 2-continued

| Ex | Pre | $^1$H-NMR (DMSO-d$_6$): δ (ppm) | MS(ESI+) |
|---|---|---|---|
| 29 | Pre. Ex. 1 Ex. 1 | 8.20-8.19 (m, 1H), 8.07-8.04 (m, 1H), 7.92-7.90 (m, 3H), 7.57 (d, J = 17.6 Hz, 1H), 6.78-6.71 (m, 1H), 6.40-6.37 (m, 1H), 2.28 (t, J = 7.2 Hz, 2H), 1.47-1.44 (m, 2H), 0.94-0.86 (m, 7H) | 422 |
| 30 | Pre. Ex. 1 Ex. 1 | 8.06 (br, 1H), 7.88 (br, 1H), 7.85 (s, 1H), 7.79-7.77 (m, 2H), 7.61 (d, J = 8.4 Hz, 2H), 7.41 (d, J = 8.0 Hz, 2H), 2.66 (t, J = 7.6 Hz, 2H), 1.61-1.55 (m, 2H), 1.35-1.30 (m, 2H), 0.91 (t, J = 7.2 Hz, 3H) | 472 |
| 31 | Pre. Ex. 1 Ex. 1 | 7.86-7.84 (m, 1H), 7.71-7.67 (m, 3H), 7.66-7.63 (m, 2H), 7.45 (dd, J = 11.6, 0.4 Hz, 1H), 7.32 (d, J = 14.8 Hz, 1H), 7.00 (d, J = 8.4 Hz, 2H), 6.96-6.92 (m, 1H), 3.82 (s, 3H) | 458 |
| 32 | Pre. Ex. 1 Ex. 1 | 8.24-8.19 (m, 1H), 8.06 (br, 1H), 7.91 (br, 2H), 7.68 (d, J = 15.6 Hz, 1H), 7.47-7.35 (m, 5H), 7.23 (s, 1H), 1.58 (br, 2H), 1.40 (br, 4H), 0.94-0.86 (m, 5H) | 498 |
| 33 | Pre. Ex. 1 Ex. 1 | 7.96 (br, 1H), 7.82 (br, 2H), 7.74-7.71 (m, 4H), 7.64-7.62 (m, 2H), 7.18 (d, J = 8.8 Hz, 2H), 7.13 (d, J = 8.8 Hz, 2H) | 573 |
| 34 | Pre. Ex. 1 Ex. 1 | 8.31 (d, J = 9.2 Hz, 2H), 8.06 (s, 1H), 7.93 (s, 1H), 7.89 (s, 1H), 7.83-7.80 (m, 4H), 7.37 (d, J = 8.8 Hz, 2H), 7.30 (d, J = 9.2 Hz, 2H) | 539 |
| 35 | Pre. Ex. 1 Ex. 1 | 8.13 (s, 1H), 7.97 (s, 1H), 7.91 (s, 1H), 7.85-7.84 (m, 2H), 7.72 (d, J = 8.4 Hz, 2H), 7.28 (d, J = 8.0 Hz, 2H), 7.10 (d, J = 8.8 Hz, 2H), 7.06 (d, J = 8.4 Hz, 2H), 2.33 (s, 3H) | 508 |
| 36 | Pre. Ex. 1 Ex. 1 | 8.07 (s, 1H), 7.91 (d, J = 9.2 Hz, 4H), 7.80 (d, J = 8.4 Hz, 4H), 7.32 (s, 1H), 7.29 (d, J = 4.0 Hz, 2H), 7.26 (s, 1H) | 519 |
| 37 | Pre. Ex. 1 Ex. 1 | 8.13 (br, 1H), 7.96 (br, 1H), 7.90 (s, 1H), 7.85-7.83 (m, 2H), 7.71 (d, J = 8.8 Hz, 2H), 7.13 (d, J = 9.2 Hz, 2H), 7.07 (d, J = 8.8 Hz, 2H), 7.03 (d, J = 8.8 Hz, 2H), 3.78 (s, 3H) | 524 |
| 38 | Pre. Ex. 1 Ex. 1 | 8.10 (br, 1H), 7.92 (br, 1H), 7.89 (s, 1H), 7.83-7.81 (m, 2H), 7.73 (d, J = 8.8 Hz, 2H), 7.33-7.29 (m, 2H), 7.25-7.21 (m, 2H), 7.13 (d, J = 8.8 Hz, 2H) | 512 |
| 39 | Pre. Ex. 1 Ex. 1 | 8.24-8.22 (m, 1H), 8.07-8.05 (m, 1H), 8.00 (s, 1H), 7.93-7.91 (m, 2H), 7.77 (d, J = 8.8 Hz, 2H), 7.52 (d, J = 8.8 Hz, 2H), 7.20 (dd, J = 8.8, 7.6 Hz, 4H) | 528 |
| 40 | Pre. Ex. 1, 7 Ex. 1 | 8.25-8.23 (m, 1H), 8.08-8.06 (m, 1H), 8.03 (d, J = 2.0 Hz, 1H), 8.00 (s, 1H), 7.93-7.91 (m, 2H), 7.65 (dd, J = 8.4, 2.0 Hz, 1H), 7.49 (dd, J = 8.4, 7.6 Hz, 2H), 7.27 (dd, J = 7.6, 7.2 Hz, 1H), 7.15 (d, J = 7.6 Hz, 2H), 7.11 (d, J = 8.8 Hz, 1H) | 528 |
| 41 | Pre. Ex. 1, 7 Ex. 1 | 8.26-8.24 (m, 1H), 8.08-8.06 (m, 1H), 8.01 (s, 1H), 7.94-7.91 (m, 2H), 7.72 (d, J = 8.8 Hz, 1H), 7.51 (dd, J = 8.4, 7.6 Hz, 2H), 7.32 (d, J = 7.2 Hz, 1H), 7.29 (d, J = 2.4 Hz, 1H), 7.22 (dd, J = 8.8, 1.2 Hz, 2H), 7.11 (dd, J = 8.8, 2.4 Hz, 1H) | 528 |
| 42 | Pre. Ex. 1, 7 Ex. 1 | 8.21-8.20 (m, 1H), 8.04-8.03 (m, 1H), 7.99 (s, 1H), 7.91-7.89 (m, 2H), 7.79 (s, 1H), 7.77 (s, 1H), 7.49 (dd, J = 8.4, 8.0 Hz, 1H), 7.34-7.31 (m, 1H), 7.29-7.28 (m, 1H), 7.22 (s, 1H), 7.20 (s, 1H), 7.15-7.12 (m, 1H) | 528 |
| 43 | Pre. Ex. 1, 7 Ex. 1 | 8.26-8.24 (m, 1H), 8.09-8.07 (m, 1H), 8.04 (d, J = 2.0 Hz, 1H), 8.01 (s, 1H), 7.94-7.92 (m, 2H), 7.67 (dd, J = 8.8, 2.0 Hz, 1H), 7.52 (dd, J = 6.8, 2.4 Hz, 2H), 7.20-7.17 (m, 3H) | 562 |
| 44 | Pre. Ex. 1, 7 Ex. 1 | 7.88-7.87 (m, 1H), 7.84 (s, 1H), 7.71 (br, 1H), 7.67-7.65 (m, 3H), 7.53 (d, J = 8.4 Hz, 2H), 7.32-7.32 (m, 1H), 7.25 (d, J = 8.8 Hz, 2H), 7.15 (d, J = 8.8 Hz, 1H) | 562 |
| 45 | Pre. Ex. 1, 7 Ex. 1 | 8.27-8.25 (m, 1H), 8.09-8.07 (m, 1H), 8.05 (d, J = 2.4 Hz, 1H), 8.03 (s, 1H), 7.95-7.92 (m, 2H), 7.69 (dd, J = 8.8, 2.0 Hz, 1H), 7.49 (dd, J = 8.4, 8.0 Hz, 1H), 7.33 (dd, J = 7.275-7.255 (m, 1H), 7.23 (s, 1H), 7.10 (dd, J = 8.4, 2.0 Hz, 1H) | 562 |
| 46 | Pre. Ex. 1,7 Ex. 1 | 7.90-7.87 (m, 1H), 7.84 (s, 1H), 7.73-7.72 (m, 1H), 7.69-7.65 (m, 3H), 7.50 (dd, J = 8.4, 7.6 Hz, 1H), 7.36-7.35 (m, 3H), 7.20-7.17 (m, 2H) | 562 |
| 47 | Pre. Ex. 1, 7 Ex. 1 | 8.23-8.21 (m, 1H), 8.07-8.05 (m, 1H), 8.01 (s, 1H), 7.93-7.91 (m, 2H), 7.56 (d, J = 8.8 Hz, 1H), 7.49 (dd, J = 8.4, 7.6 Hz, 2H), 7.28 (dd, J = 7.2, 7.2 Hz, 1H), 7.19 (dd, J = 8.4, 0.8 Hz, 2H), 6.89 (d, J = 3.2 Hz, 1H), 6.60 (dd, J = 8.4, 3.2 Hz, 1H), 3.93 (s, 3H) | 524 |
| 48 | Pre. Ex. 1, 7 Ex. 1 | 8.23-8.21 (m, 1H), 8.06-8.05 (m, 1H), 8.01 (s, 1H), 7.93-7.90 (m, 2H), 7.54 (d, J = 2.0 Hz, 1H), 7.40 (dd, J = 8.4, 7.6 Hz, 2H), 7.32 (dd, J = 8.4, 2.0 Hz, 1H), 7.16 (dd, J = 7.6, 7.2 Hz, 1H), 7.09 (d, J = 8.4 Hz, 1H), 7.00 (d, J = 7.6 Hz, 2H), 3.88 (s, 3H) | 524 |

TABLE 2-continued

| Ex | Pre | $^1$H-NMR (DMSO-d$_6$): δ (ppm) | MS(ESI+) |
|---|---|---|---|
| 49 | Pre. Ex. 1 Ex. 1 | 8.58 (s, 1H), 8.28 (br, 1H), 8.16 (d, J = 8.8 Hz, 1H), 8.10 (br, 1H), 8.04 (s, 1H), 7.95 (br, 2H), 7.48 (dd, J = 7.6, 7.6 Hz, 2H), 7.31-7.22 (m, 4H) | 495 |
| 50 | Pre. Ex. 1, 6 Ex. 1 | 8.12 (d, J = 2.0 hz, 1H), 8.03 (br, 1H), 7.87 (s, 2H), 7.78 (br, 2H), 7.66 (dd, J = 8.8, 2.0 Hz, 1H), 7.47 (dd, J = 8.4, 7.6 Hz, 2H), 7.26 (dd, J = 7.6, 7.2 Hz, 1H), 7.13 (d, J = 8.0 Hz, 2H), 7.07 (d, J = 8.8 Hz, 1H) | 572 |
| 51 | Pre. Ex. 1, 6 Ex. 1 | 8.26-8.24 (m, 1H), 8.08-8.24 (m, 1H), 8.00 (s, 1H), 7.94-7.92 (m, 2H), 7.53 (dd, J = 8.0, 7.6 Hz, 1H), 7.35-7.29 (m, 4H), 7.21 (dd, J = 4.8, 2.0 Hz, 1H), 7.00 (dd, J = 8.8, 1.2 Hz, 2H), 6.96 (dd, J = 7.2, 6.4 Hz, 1H), 4.42 (t, J = 3.2 Hz, 2H), 4.36 (t, J = 2.8 Hz, 2H) | 538 |
| 52 | Pre. Ex. 1, 6 Ex. 1 | 8.27-8.26 (m, 1H), 8.10-8.08 (m, 1H), 8.00 (s, 1H), 7.95-7.93 (m, 2H), 7.73 (d, J = 8.8 Hz, 2H), 7.31 (dd, J = 8.8, 7.6 Hz, 2H), 7.24 (d, J = 8.8 Hz, 2H), 7.01-6.94 (m, 3H), 4.46 (dd, J = 6.4, 4.0 Hz, 2H), 4.35 (dd, J = 4.4, 2.0 Hz, 2H) | 538 |
| 53 | Pre. Ex. 1, 6 Ex. 1 | 8.26-8.24 (m, 1H), 8.14 (s, 1H), 8.09-8.07 (m, 1H), 7.94-7.92 (m, 2H), 7.58 (dd, J = 8.0, 6.8 Hz, 2H), 7.33-7.27 (m, 3H), 7.19 (dd, J = 8.8, 8.0 Hz, 1H), 7.00 (dd, J = 8.8, 0.8 Hz, 2H), 6.93 (dd, J = 7.2, 7.2 Hz, 1H), 4.53 (t, J = 4.0 Hz, 2H), 4.41 (t, J = 4.4 Hz, 2H) | 538 |
| 54 | Pre. Ex. 1, 6 Ex. 1 | 8.05 (s, 2H), 7.88 (s, 1H), 7.79-7.77 (m, 2H), 7.57-7.52 (m, 2H), 7.30 (d, J = 8.0 Hz, 1H), 7.16 (dd, J = 8.8, 7.6 Hz, 1H), 7.13-7.08 (m, 2H), 7.04-7.03 (m, 2H), 4.50 (br, 2H), 4.38 (br, 2H) | 556 |
| 55 | Pre. Ex. 1, 6 Ex. 1 | 8.02 (s, 1H), 7.98 (s, 1H), 7.82 (s, 1H), 7.74 (br, 2H), 7.53-7.51 (m, 2H), 7.28 (d, J = 8.0 Hz, 1H), 7.17 (dd, J = 8.0, 7.6 Hz, 1H), 7.08 (d, J = 8.4 Hz, 2H), 6.89 (d, J = 8.8 Hz, 2H), 4.48 (t, J = 4.0 Hz, 2H), 4.36 (br, 2H) | 552 |
| 56 | Pre. Ex. 1, 6 Ex. 1 | 8.21 (d, J = 9.2 Hz, 2H), 7.96 (s, 1H), 7.87-7.85 (m, 1H), 7.70-7.69 (m, 1H), 7.65-7.63 (m, 2H), 7.55-7.49 (m, 2H), 7.29 (d, J = 8.0 Hz, 1H), 7.24 (d, J = 9.2 Hz, 2H), 7.18 (dd, J = 7.6, 7.2 Hz, 1H), 4.59-4.54 (m, 4H) | 583 |
| 57 | Pre. Ex. 1, 6 Ex. 1 | 7.98 (s, 1H), 7.09-7.88 (m, 1H), 7.74-7.72 (m, 1H), 7.67-7.65 (m, 2H), 7.50 (dd, J = 9.2, 8.0 Hz, 2H), 7.27 (dd, J = 8.4, 7.2 Hz, 2H), 7.22 (d, J = 8.0 Hz, 1H), 7.14 (dd, J = 7.6, 7.6 Hz, 1H), 6.96 (dd, J = 8.8, 1.2 Hz, 2H), 6.91 (dd, J = 7.6, 7.6 Hz, 1H), 4.31 (t, J = 6.0 Hz, 2H), 4.17 (t, J = 6.4 Hz, 2H), 2.30-2.23 (m, 2H) | 552 |
| 58 | Pre. Ex. 1, 6 Ex. 1 | 8.15 (br, 1H), 8.11 (s, 1H), 7.98 (br, 1H), 7.86-7.84 (m, 2H), 7.58-7.54 (m, 2H), 7.29 (d, J = 8.4 Hz, 1H), 7.20 (dd, J = 7.6, 7.6 Hz, 1H), 6.94-6.89 (m, 1H), 6.88-6.82 (m, 1H), 4.70-4.69 (m, 1H), 4.51-4.46 (m, 2H), 4.39 (dd, J = 10.8, 6.0 Hz, 1H), 4.18 (dd, J = 11.6, 6.8 Hz, 1H), 3.13-3.06 (m, 1H), 1.17 (t, J = 7.2 Hz, 2H) | 566 |
| 59 | Pre. Ex. 1, 6 Ex. 1 | 8.26 (s, 1H), 8.11 (s, 1H), 7.97 (m, 3H) 7.56 (br, 1H), 7.28 (br, 4H), 6.98-6.97 (m, 3H), 4.63 (br, 2H), 4.39 (br, 2H) | 572 |
| 60 | Pre. Ex. 1, 6 Ex. 1 | 8.29 (d, J = 11.6 Hz, 2H), 8.13 (s, 1H), 7.96 (s, 3H), 7.46 (s, 2H), 7.28 (s, 2H), 7.02 (s, 2H), 6.92 (s, 1H), 4.27 (s, 2H), 4.22 (s, 2H), 2.35 (s, 3H) | 552 |
| 61 | Pre. Ex. 1, 6 Ex. 1 | 8.28-8.26 (m, 1H), 8.11 (s, 2H), 7.96-7.94 (m, 2H), 7.31-7.27 (m, 3H), 7.20-7.17 (m, 1H), 7.05 (d, J = 2.8 Hz, 1H), 7.00 (d, J = 8.0 Hz, 2H), 6.91 (dd, J = 7.2, 7.2 Hz, 1H), 4.47 (s, 2H), 4.36 (d, J = 4.0 Hz, 2H), 3.81 (s, 3H) | 568 |
| 62 | Pre. Ex. 1, 6 Ex. 1 | 8.27 (s, 1H), 8.10 (s, 1H), 8.04 (s, 1H), 7.95 (s, 2H), 7.58 (s, 1H), 7.49 (s, 1H), 7.40 (s, 1H), 7.29 (s, 2H), 7.01-6.94 (m, 3H), 4.58 (s, 2H), 4.40 (s, 2H) | 616 |
| 63 | Pre. Ex. 1, 6 Ex. 1 | 8.30-8.28 (m, 1H), 8.23 (s, 1H), 8.12-8.10 (m, 1H), 7.96-7.94 (m, 2H), 7.72 (d, J = 8.0 Hz, 2H), 7.60 (d, J = 7.2 Hz, 1H), 7.40 (dd, J = 8.0, 7.6 Hz, 1H), 7.27 (dd, J = 8.0, 7.6 Hz, 2H), 6.99 (d, J = 8.0 Hz, 2H), 6.91 (dd, J = 7.2, 7.2 Hz, 1H), 4.43 (d, J = 2.4 Hz, 2H), 4.29 (d, J = 2.4 Hz, 2H) | 572 |
| 64 | Pre. Ex. 1, 6 Ex. 1 | 7.85-7.83 (m, 1H), 7.70-7.69 (m, 1H), 7.64-7.62 (m, 2H), 7.47 (d, J = 3.6 Hz, 1H), 7.37-7.30 (m, 3H), 7.14 (d, J = 8.8 Hz, 1H), 7.00 (d, J = 8.0 Hz, 2H), 6.91 (dd, J = 7.6, 7.2 Hz, 1H), 4.44-4.32 (m, 4H) | 572 |
| 65 | Pre. Ex. 1, 6 Ex. 1 | 8.26 (s, 1H), 8.19 (br, 1H), 8.01 (br, 1H), 7.89-7.88 (m, 2H), 7.30-7.24 (m, 4H), 7.15-7.13 (m, 1H), 6.97 (d, J = 8.0 Hz, 2H), 6.89 (dd, J = 7.6, 7.2 Hz, 1H), 4.45 (d, J = 3.6 Hz, 2H), 4.21 (d, J = 4.4 Hz, 2H), 3.88 (s, 3H) | 567 |
| 66 | Pre. Ex. 1, 6 Ex. 1 | 8.17-8.16 (m, 1H), 8.09 (s, 1H), 8.01-8.00 (m, 1H), 7.89-7.88 (m, 2H), 7.43 (d, J = 8.0 Hz, 1H), 7.29 (dd, J = 8.4, 7.2 Hz, 2H), 7.16 (s, 1H), 7.02-7.00 (m, 3H), 6.93 (dd, J = 7.2, 7.2 Hz, 1H), 4.51 (s, 2H), 4.40 (s, 2H), 2.40 (s, 3H) | 552 |

TABLE 2-continued

| Ex | Pre | ¹H-NMR (DMSO-d$_6$): δ (ppm) | MS(ESI+) |
|---|---|---|---|
| 67 | Pre. Ex. 1, 6 Ex. 1 | 8.18 (s, 2H), 8.00 (br, 1H), 7.89-7.89 (m, 3H), 7.64 (dd, J = 7.6, 0.8 Hz, 1H), 7.35-7.26 (m, 3H), 7.00 (d, J = 7.6 Hz, 2H), 6.91 (dd, J = 7.2, 7.2 Hz, 1H), 4.38 (d, J = 4.4 Hz, 2H), 4.31 (t, J = 2.0 Hz, 2H) | 616 |
| 68 | Pre. Ex. 1, 6 Ex. 1 | 8.28-8.26 (m, 1H), 8.19 (s, 1H), 8.12-8.11 (m, 1H), 7.97-7.95 (m, 3H), 7.56 (dd, J = 8.4, 8.4 Hz, 1H), 7.28 (dd, J = 8.4, 7.2 Hz, 2H), 6.99 (d, J = 8.0 Hz, 2H), 6.93 (dd; J = 12.0, 7.2 Hz, 2H), 4.53 (s, 2H), 4.38 (t, J = 3.2 Hz, 2H), 3.96 (s, 3H) | 568 |
| 69 | Pre. Ex. 1, 6 Ex. 1 | 8.15 (br, 1H), 8.06 (s, 1H), 7.98 (br, 1H), 7.87-7.85 (m, 2H), 7.49 (d, J = 8.8 Hz, 1H), 7.29 (dd, J = 8.8, 7.6 Hz, 2H), 7.01 (d, J = 8.4 Hz, 2H), 6.93 (dd, J = 7.6, 7.2 Hz, 1H), 6.85 (s, 1H), 6.79 (dd, J = 8.8, 2.4 Hz, 1H), 4.54 (br, 2H), 4.41 (br, 2H), 3.89 (s, 3H) | 568 |
| 70 | Pre. Ex. 1, 6 Ex. 1 | 8.26-8.24 (m, 1H), 8.11 (s, 1H), 8.09-8.07 (m, 1H), 7.95-7.92 (m, 2H), 7.41-7.21 (m, 5H), 6.99 (dd, J = 7.6, 1.2 Hz, 2H), 6.93 (dd, 7.2, 7.2 Hz, 1H), 4.49 (br, 2H), 4.39-4.38 (m, 2H), 2.35 (s, 3H) | 552 |
| 71 | Pre. Ex. 1, 6 Ex. 1 | 8.28 (s, 1H), 8.17 (br, 1H), 8.11-8.10 (m, 1H), 7.96-7.95 (m, 2H), 7.55 (dd, J = 7.6, 6.8 Hz, 2H), 7.30-7.14 (m, 7H), 4.17 (t, J = 5.6 Hz, 2H), 2.78 (t, J = 7.2 Hz, 2H), 2.13 (t, J = 6.8 Hz, 2H) | 536 |
| 72 | Pre. Ex. 1 Ex. 1 | 8.26-8.25 (m, 1H), 8.09-8.08 (m, 1H), 7.98 (s, 1H), 7.95-7.93 (m, 2H), 7.66 (d, J = 7.6 Hz, 2H), 7.46 (d, J = 7.6 Hz, 2H), 7.34-7.20 (m, 5H), 4.04 (s, 2H) | 492 |
| 73 | Pre. Ex. 1, 7 Ex. 1 | | 520 |
| 74 | Pre. Ex. 1, 7 Ex. 1 | 8.94 (br, 1H), 8.38 (s, 1H), 8.33 (dd, J = 12.4, 8.4 Hz, 1H), 7.91-7.88 (m, 1H), 7.80-7.71 (m, 6H), 7.50 (dd, J = 8.0, 7.6 Hz, 3H), 7.28 (dd, J = 7.2, 7.2 Hz, 1H), 7.24 (d, J = 7.6 Hz, 2H), 6.98 (d, J = 8.0 Hz, 1H) | 544 |
| 75 | Pre. Ex. 1, 7 Ex. 1 | 9.10 (br, 1H), 8.26 (s, 1H), 8.16 (d, J = 8.8 Hz, 1H), 7.97 (d, J = 8.8 Hz, 1H), 7.91-7.89 (m, 2H), 7.73-7.71 (m, 2H), 7.67-7.65 (m, 2H), 7.47 (dd, J = 8.4, 7.6 Hz, 2H), 7.40 (s, 1H), 7.38 (d, J = 2.4 Hz, 1H), 7.24 (dd, J = 7.6, 7.2 Hz, 1H), 7.17 (d, J = 7.6 Hz, 2H) | 544 |
| 76 | Pre. Ex. 2 | 7.79 (s, 1H), 7.48 (d, J = 8.8 Hz, 2H), 7.41 (dd, J = 8.4, 7.2 Hz, 2H), 7.22 (dd, J = 6.8, 5.6 Hz, 1H), 7.07 (dd, J = 8.4, 7.6 Hz, 4H), 5.31 (s, 3H) | 329 |
| 77 | Pre. Ex. 2 Ex. 79 | 11.71 (s, 1H), 7.97 (s, 1H), 7.88 (d, J = 8.4 Hz, 2H), 7.77 (d, J = 8.8 Hz, 2H), 7.48 (dd, J = 8.4, 7.6 Hz, 2H), 7.39 (d, J = 8.0 Hz, 2H), 7.27 (dd, J = 7.2, 7.2 Hz, 1H), 7.16 (dd, J = 7.6, 7.2 Hz, 4H), 2.41 (s, 3H) | 447 |
| 78 | Pre. Ex. 2 Ex. 79 | 11.62 (s, 1), 7.96 (d, J = 7.2 Hz, 3H), 7.75 (d, J = 8.8 Hz, 2H), 7.48 (dd, J = 8.0, 7.6 Hz, 2H), 7.27 (dd, J = 7.6, 7.2 Hz, 1H), 7.17-7.11 (m, 6H), 3.86 (s, 3H) | 463 |
| 79 | Pre. Ex. 2 Ex. 79 | 12.16 (s, 1H), 8.18 (dd, J = 18.4, 9.6 Hz, 4H), 8.00 (s, 1H), 7.77 (d, J = 8.8 Hz, 2H), 7.49 (dd, J = 8.4, 7.6 Hz, 2H), 7.28 (dd, J = 7.6, 6.8 Hz, 1H), 7.16 (dd, J = 8.0, 7.6 Hz, 4H), 3.37 (s, 3H) | 511 |
| 80 | Pre. Ex. 2 Ex. 79 | 11.80 (s, 1H), 7.98 (s, 1H), 7.76 (d, J = 8.8 Hz, 2H), 7.57 (d, J = 8.0 Hz, 1H), 7.53-7.47 (m, 4H), 7.29-7.25 (m, 2H), 7.16 (dd, J = 8.8, 6.8 Hz, 4H), 3.85 (s, 3H) | 463 |
| 81 | Pre. Ex. 2 Ex. 79 | 11.75 (s, 1H), 7.97 (s, 1H), 7.91 (d, J = 8.4 Hz, 2H), 7.76 (d, J = 9.2 Hz, 2H), 7.48 (dd, J = 8.4, 7.6 Hz, 2H), 7.44 (d, J = 8.8 Hz, 2H), 7.27 (dd, J = 7.6, 7.2 Hz, 1H), 7.15 (dd, J = 8.4, 7.2 Hz, 4H), 2.56 (s, 3H) | 479 |
| 82 | Pre. Ex. 2 Ex. 79 | 12.49 (s, 1H), 8.87 (s, 1H), 8.76 (dd, J = 8.4, 1.2 Hz, 1H), 8.10 (d, J = 8.4 Hz, 1H), 7.99 (s, 1H), 7.75 (d, J = 9.2 Hz, 1H), 7.49 (dd, J = 8.4, 7.6 Hz, 3H), 7.27 (dd, J = 7.6, 6.8 Hz, 1H), 7.16 (dd, J = 8.4, 6.0 Hz, 5H) | 523 |
| 83 | Pre. Ex. 2 Ex. 79 | 12.20 (s, 1H), 8.56 (s, 1H), 8.30 (d, J = 8.0 Hz, 1H), 8.26 (d, J = 8.0 Hz, 1H), 8.00 (s, 1H), 7.90 (dd, J = 8.0, 7.6 Hz, 1H), 7.77 (d, J = 8.8 Hz, 2H), 7.49 (dd, J = 8.4, 7.2 Hz, 2H), 7.28 (dd, J = 7.6, 7.2 Hz, 1H), 7.16 (dd, J = 8.4, 8.0 Hz, 4H) | 511 |
| 84 | Pre. Ex. 2 Ex. 79 | 7.93 (dd, J = 6.0, 5.6 Hz, 1H), 7.76 (d, J = 8.0 Hz, 3H), 7.67 (d, J = 8.8 Hz, 2H), 7.62-7.56 (m, 3H), 7.47 (dd, J = 8.4, 7.6 Hz, 2H), 7.26 (dd, J = 7.6, 7.2 Hz, 1H), 7.13 (dd, J = 7.2, 7.2 Hz, 4H), 4.09 (t, J = 6.4 Hz, 2H), 3.11 (q, J = 6.4 Hz, 2H) | 497 |
| 85 | Pre. Ex. 4 Ex. 1 | 7.81 (s, 1H), 7.68 (d, J = 8.8 Hz, 2H), 7.47 (dd, J = 8.4, 7.2 Hz, 2H), 7.26 (dd, J = 7.2, 7.2 Hz, 1H), 7.13 (dd, J = 8.4, 6.8 Hz, 4H), 4.16 (t, J = 6.8 Hz, 2H), 3.52 (t, J = 4.4 Hz, 4H), 2.60 (t, J = 6.4 Hz, 2H), 2.433 (s, 4H) | 427 |

TABLE 2-continued

| Ex | Pre | $^1$H-NMR (DMSO-$d_6$): δ (ppm) | MS(ESI+) |
|---|---|---|---|
| 86 | Pre. Ex. 3 Ex. 1 | 7.83 (s, 1H), 7.69 (d, J = 8.8 Hz, 2H), 7.47 (dd, J = 8.4, 7.6 Hz, 2H), 7.26 (dd, J = 7.6, 7.2 Hz, 1H), 7.14-7.12 (m, 4H), 4.16 (t, J = 6.8 Hz, 2H), 3.03-2.97 (m, 9H), 2.84-2.80 (m, 2H) | 475 |
| 87 | Pre. Ex. 4 Ex. 1 | 7.72 (s, 1H), 7.65 (d, J = 8.8 Hz, 2H), 7.47 (dd, J = 8.4, 7.6 Hz, 2H), 7.32-7.25 (m, 6H), 7.12 (dd, J = 10.0, 8.0 Hz, 4H), 4.94-4.87 (m, 1H), 3.50 (s, 2H), 2.94 (d, J = 11.6 Hz, 2H), 2.01 (t, J = 17.6 Hz, 2H), 1.62 (d, J = 9.6 Hz, 2H) | 487 |
| 88 | Pre. Ex. 4 Ex. 1 | 10.88 (s, 1H), 7.28 (s, 1H), 7.70 (d, J = 8.8 Hz, 2H), 7.47 (dd, J = 8.4, 7.6 Hz, 2H), 7.26 (dd, J = 7.6, 7.2 Hz, 1H), 7.16-7.12 (m, 4H), 4.42 (s, 2H), 4.04-3.98 (m, 2H), 3.75 (t, J = 11.6 Hz, 2H), 3.73 (d, J = 11.6 Hz, 2H), 3.48 (br, 2H), 3.17 (br, 2H) | 427 |
| 89 | Pre. Ex. 3 Ex. 1 | 7.80 (s, 1H), 7.68 (d, J = 8.8 Hz, 2H), 7.47 (dd, J = 7.6, 7.2H, 2H), 7.26 (dd, J = 7.6, 7.2 Hz, 1H), 7.14 (dd, J = 7.2, 6.4 Hz, 4H), 3.95-3.89 (m, 4H), 3.17 (d, J = 5.2 Hz, 1H), 2.67 (br, 1H), 2.07 (br, 1H), 1.57 (d, J = 10.8 Hz, 2H), 1.39 (s, 9H), 1.13-1.10 (m, 2H) | 511 |
| 90 | Ex. 89 de-Boc reaction | 8.80 (s, 1H), 8.52 (d, J = 10.4 Hz, 1H), 7.81 (s, 1H), 7.69 (d, J = 8.8 Hz, 2H), 7.47 (dd, J = 8.4, 7.6 Hz, 2H), 7.26 (dd, J = 7.6, 7.2 Hz, 1H), 7.14 (dd, J = 8.8, 6.4 Hz, 4H), 3.97 (d, J = 7.2 Hz, 2H), 3.24 (d, J = 12.4 Hz, 2H), 2.81 (d, J = 11.2 Hz, 2H), 2.19 (br, 1H), 1.76 (d, J = 12.4 Hz, 2H), 1.46 (d, J = 10.4 Hz, 2H) | 411 |
| 91 | Ex. 90, 79 | 7.81 (s, 1H), 7.68 (d, J = 8.8 Hz, 2H), 7.47 (dd, J = J = 8.4, 7.6 Hz, 2H), 7.26 (t, J = 7.2 Hz, 1H), 7.13 (dd, J = J = 8.4, 6.4 Hz, 4H), 3.98 (d, J = 7.2 Hz, 2H), 3.53 (d, J = 12.0 Hz, 2H), 2.83 (s, 3H), 2.67-2.64 (m, 2H), 2.03 (br, 1H), 1.71 (d, J = 11.2 Hz, 2H), 1.32-1.28 (m, 2H) | 489 |
| 92 | Ex. 90, 79 | 7.80 (s, 1H), 7.68 (d, J = 8.8 Hz, 2H), 7.47 (dd, J = 8.4, 7.6 Hz, 2H), 7.26 (dd, J = 7.6, 7.2 Hz, 1H), 7.13 (dd, J = 8.0, 6.4 Hz, 4H), 4.28 (d, J = 13.2 Hz, 1H), 4.10-3.99 (m, 2H), 3.95 (d, J = 7.2 Hz, 2H), 3.74 (d, J = 13.2 Hz, 1H), 3.27 (s, 3H), 2.93-2.87 (m, 1H), 2.18-2.12 (m, 1H), 1.62 (d, J = 12.0 Hz, 2H), 1.22-1.19 (m, 1H), 1.10-1.07 (m, 1H) | 483 |
| 93 | Pre. Ex. 4 Ex. 1 | 7.83 (s, 1H), 7.69 (d, J = 8.8 Hz, 2H), 7.47 (dd, J = 8.4, 7.2 Hz, 2H), 7.26 (dd, J = 7.2, 6.4 Hz, 1H), 7.14 (dd, J = 8.8, 7.6 Hz, 4H), 4.112-4.07 (m, 1H), 3.94 (d, J = 7.6 Hz, 2H), 3.72-3.69 (m, 2H), 2.80 (t, J = 10.4 Hz, 1H), 2.00 (br, 1H), 1.72-1.62 (m, 2H), 1.35 (s, 9H), 1.27 (br, 2H) | 511 |
| 94 | Ex. 93 de-Boc reaction | 8.88 (br, 2H), 7.12 (s, 1H), 7.69 (d, J = 8.8 Hz, 2H), 7.47 (dd, J = 8.4, 7.2 Hz, 2H), 7.26 (dd, J = 7.2, 7.2 Hz, 1H), 7.13 (dd, J = 7.6, 5.2 Hz, 4H), 3.98-3.96 (m, 2H), 3.24 (d, J = 10.0 Hz, 1H), 3.15 (d, J = 12.0 Hz, 1H), 2.79-2.67 (m, 2H), 2.33 (br, 1H), 1.76 (t, J = 23.2 Hz, 2H), 1.63-1.59 (m, 1H), 1.37-1.31 (m, 1H) | 411 |
| 95 | Ex. 94, 79 | 7.82 (s, 1H), 7.69 (d, J = 8.8 Hz, 2H), 7.47 (dd, J = 8.4, 7.6 Hz, 2H), 7.26 (dd, J = 7.6, 7.2 Hz, 1H), 7.13 (dd, J = 8.4, 7.2 Hz, 4H), 4.05-3.92 (m, 2H), 3.44-3.37 (m, 2H), 2.84 (s, 3H), 2.77-2.72 (m, 1H), 2.64 (t, J = 11.2 Hz, 1H), 2.17 (br, 1H), 1.76-1.74 (m, 1H), 1.71-1.66 (m, 1H), 1.46-1.42 (m, 1H), 1.23-1.17 (m, 1H) | 489 |
| 96 | Pre. Ex. 4 Ex. 1 | 7.83 (s, 1H), 7.70-7.64 (m, 2H), 7.47 (dd, J = 8.0, 7.6 Hz, 2H), 7.26 (dd, J = 7.6, 7.2 Hz, 1H), 7.13 (dd, J = 8.8, 7.2 Hz, 4H), 4.37 (br, 1H), 4.26-4.12 (m, 1H), 3.94-3.90 (m, 1H), 3.20 (d, J = 8.0 Hz, 2H), 1.90-1.88 (m, 3H), 1.74 (d, J = 9.2 Hz, 1H), 1.26 (s, 9H) | 497 |
| 97 | Ex. 96 de-Boc reaction | 7.83 (s, 1H), 7.70 (d, J = 8.8 Hz, 2H), 7.48 (dd, J = 8.4, 7.6 Hz, 2H), 7.26 (dd, J = 7.2, 7.2 Hz, 1H), 7.15-7.14 (m, 4H), 4.38-4.34 (m, 2H), 3.77-3.74 (m, 1H), 3.29-3.26 (m, 1H), 3.13-3.08 (m, 1H), 2.10-2.08 (m, 1H), 1.99-1.88 (m, 2H), 1.80-1.72 (m, 1H) | 397 |
| 98 | Ex. 97, 79 | 7.75 (s, 1H), 7.67 (d, J = 8.8 Hz, 2H), 7.46 (dd, J = 8.4, 7.6 Hz, 2H), 7.25 (dd, J = 7.6, 6.8 Hz, 1H), 7.15-7.11 (m, 4H), 4.26-4.20 (m, 2H), 3.91 (dd, J = 3.2 Hz, 1H), 3.29-3.26 (m, 1H), 2.80 (s, 3H), 1.99-1.94 (m, 3H), 1.78-1.76 (m, 1H) | 475 |
| 99 | Pre. Ex. 3 Ex. 1 | 7.73 (s, 1H), 7.66 (d, J = 8.8 Hz, 2H), 7.47 (dd, J = 8.4, 7.6 Hz, 2H), 7.25 (dd, J = 7.2, 7.2 Hz, 1H), 7.13 (dd, J = 9.2, 7.6 Hz, 4H), 5.10 (t, J = 11.6 Hz, 1H), 4.09-4.08 (m, 2H), 2.81 (br, 2H), 2.41-2.39 (m, 2H), 1.67 (d, J = 9.6 Hz, 2H), 1.43 (s, 9H) | 497 |

TABLE 2-continued

| Ex | Pre | $^1$H-NMR (DMSO-$d_6$): δ (ppm) | MS(ESI+) |
|---|---|---|---|
| 100 | Ex. 99 de-Boc reaction | 7.73 (s, 1H), 7.66 (d, J = 8.8 Hz, 2H), 7.47 (dd, J = 8.8, 7.6 Hz, 2H), 7.26 (dd, J = 7.6, 6.8 Hz, 1H), 7.13 (dd, J = 8.4, 8.4 Hz, 4H), 5.21-5.15 (m, 1H), 3.40 (d, J = 12.8 Hz, 2H), 3.05 (dd, J = 13.2, 11.2 Hz, 2H), 2.79-2.71 (m, 2H), 1.89 (d, J = 13.2 Hz, 2H) | 397 |
| 101 | Pre. Ex. 3 Ex. 1 de-Boc reaction | 7.82 (s, 1H), 7.71 (d, J = 8.8 Hz, 2H), 7.48 (dd, J = 8.4, 7.2 Hz, 2H), 7.27 (dd, J = 7.2, 7.2 Hz, 1H), 7.14 (dd, J = 7.6, 4.0 Hz, 4H), 4.30-4.26 (m, 1H), 4.13 (dd, J = 14.8, 4.0 Hz, 1H), 3.47 (br, 1H), 3.29-3.26 (m, 1H), 2.82 (br, 1H), 1.88-1.85 (m, 1H), 1.78-1.75 (m, 1H), 1.67-1.47 (m, 4H) | 411 |
| 102 | Pre. Ex. 3 Ex. 1 | 8.83 (s, 1H), 7.83 (s, 1H), 7.70 (d, J = 8.8 Hz, 2H), 7.48 (dd, J = 8.8, 7.6 Hz, 2H), 7.26 (dd, J = 7.2, 7.2 Hz, 1H), 7.14 (dd, J = 7.6, 4.8 Hz, 4H), 4.33 (t, J = 5.6 Hz, 2H), 3.27 (t, J = 5.6 Hz, 2H), 2.99 (dd, J = 14.4, 7.2 Hz, 2H), 1.18 (t, J = 7.2 Hz, 3H) | 532 |
| 103 | Pre. Ex. 3 Ex. 1, 163 | 7.78 (s, 1H), 7.67 (d, J = 8.8 Hz, 2H), 7.46 (dd, J = 8.4, 7.6 Hz, 2H), 7.25 (dd, J = 7.6, 7.2 Hz, 1H), 7.13 (dd, J = 10.4, 9.2 Hz, 4H), 4.45 (t, J = 6.8 Hz, 1H), 4.14 (t, J = 7.2 Hz, 2H), 3.01 (dd, J = 14.0, 6.8 Hz, 2H) | 437 |
| 104 | Pre. Ex. 3 Ex. 1 | 9.06 (s, 1H), 7.79 (s, 1H), 7.67 (d, J = 8.8 Hz, 2H), 7.47 (dd, J = 8.4, 7.6 Hz, 2H), 7.26 (dd, J = 7.6, 7.2 Hz, 1H), 7.13 (dd, J = 8.8, 7.6 Hz, 4H), 5.77 (s, 1H), 4.23 (t, J = 6.0 Hz, 2H), 3.67-3.63 (m, 2H), 2.11 (s, 3H) | 502 |
| 105 | Ex. 94, 163 | 7.83 (s, 1H), 7.69 (d, J = 8.8 Hz, 2H), 7.47 (dd, J = 7.6, 7.6 Hz, 2H), 7.26 (dd, J = 7.2, 7.2 Hz, 1H), 7.13 (dd, J = 9.6, 9.2 Hz, 4H), 3.99-3.87 (m, 2H), 3.24-3.17 (m, 2H), 2.28-2.13 (m, 3H), 1.61 (t, J = 13.6 Hz, 2H), 1.36 (s, 1H), 0.97 (d, J = 10.4 Hz, 1H) | 491 |
| 106 | Ex. 90, 163 | 7.80 (s, 1H), 7.88 (d, J = 8.0 Hz, 2H), 7.47 (dd, J = 7.6, 7.6 Hz, 2H), 7.26 (dd, J = 7.2, 7.2 Hz, 1H), 7.13 (dd, J = 8.0, 8.0 Hz, 4H), 3.96-3.95 (m, 2H), 2.89 (s, 3H), 2.73 (s, 1H), 1.91-1.85 (m, 2H), 1.54-1.49 (m, 2H) | 491 |
| 107 | Ex. 97, 163 | 7.79 (s, 1H), 7.68 (d, J = 8.8 Hz, 2H), 7.47 (dd, J = 8.0, 7.6 Hz, 2H), 7.26 (dd, J = 7.6, 7.2 Hz, 1H), 7.14 (dd, J = 8.8, 6.8 Hz, 4H), 4.41-4.39 (m, 2H), 4.29-4.21 (m, 2H), 3.45 (t, J = 6.8 Hz, 2H), 2.06-2.01 (m, 1H), 1.93-1.85 (m, 2H), 1.76-1.67 (m, 1H) | 477 |
| 108 | Pre. Ex. 5 | 7.76 (s, 1H), 7.68 (d, J = 8.8 Hz, 2H), 7.47 (dd, J = 8.4, 7.6 Hz, 2H), 7.25 (dd, J = 7.6, 7.2 Hz, 1H), 7.13 (dd, J = 8.8, 8.4 Hz, 4H), 4.30 (s, 2H) | 372 |
| 109 | Pre. Ex. 5 Ex. 117 | | 526 |
| 110 | Pre. Ex. 5 Ex. 117 | 8.91 (s, 1H), 7.86 (s, 1H), 7.78 (d, J = 8.0 Hz, 2H), 7.71 (d, J = 8.0 Hz, 2H), 7.49-7.42 (m, 4H), 7.32 (s, 2H), 7.26 (dd, J = 7.2, 7.2 Hz, 1H), 7.14 (dd, J = 8.4, 7.2 Hz, 4H), 4.74 (s, 2H), 4.38 (d, J = 5.2 Hz, 2H), 1.23 (s, 1H) | 540 |
| 111 | Pre. Ex. 5 Ex. 117 | 7.85 (s, 1H), 7.71 (d, J = 8.8 Hz, 2H), 7.47 (dd, J = 8.4, 7.6 Hz, 2H), 7.26 (dd, J = 7.2, 7.2 Hz, 1H), 7.14 (dd, J = 8.8, 7.6 Hz, 4H), 4.93 (s, 2H), 3.51 (t, J = 5.2 Hz, 2H), 3.41 (t, J = 5.2 Hz, 2H), 1.598 (br, 4H), 1.437 (br, 2H) | 439 |
| 112 | Pre. Ex. 5 Ex. 117 | 7.86 (s, 1H), 7.71 (d, J = 8.8 Hz, 2H), 7.47 (dd, J = 8.4, 7.6 Hz, 2H), 7.26 (dd, J = 7.6, 7.2 Hz, 1H), 7.14 (dd, J = 8.8, 8.4 Hz, 4H), 4.97 (s, 2H), 3.65 (d, J = 4.8 Hz, 2H), 3.61-3.56 (m, 4H), 3.45-3.44 (m, 2H) | 441 |
| 113 | Pre. Ex. 5 Ex. 117 | 7.86 (s, 1H), 7.71 (d, J = 8.8 Hz, 2H), 7.47 (dd, J = 8.0, 7.6 Hz, 2H), 7.28-7.19 (m, 5H), 7.16 (dd, J = 8.8, 8.0 Hz, 4H), 5.06 (d, J = 5.2 Hz, 2H), 4.83 (s, 1H) 4.61 (s, 1H), 3.83 (t, J = 6.0 Hz, 1H), 3.67 (t, J = 6.0 Hz, 1H), 2.96 (t, J = 6.0 Hz, 1H), 2.80 (t, J = 6.0 Hz, 1H) | 487 |
| 114 | Pre. Ex. 5 Ex. 117 | 7.85 (s, 1H), 7.70 (d, J = 5.2 Hz, 2H), 7.47 (dd, J = 8.4, 7.6 Hz, 2H), 7.26 (dd, J = 7.6, 6.8 Hz, 1H), 7.14 (dd, J = 8.8, 8.0 Hz, 4H), 4.93 (s, 2H), 3.09 (s, 3H), 2.85 (s, 3H) | 339 |
| 115 | Pre. Ex. 5 Ex. 117 | 7.67 (s, 1H), 7.71 (d, J = 5.2 Hz, 2H), 7.47 (dd, J = 8.4, 7.6 Hz, 2H), 7.26 (dd, J = 7.6, 7.2 Hz, 1H), 7.14 (dd, J = 9.2, 7.6 Hz, 4H), 4.95 (s, 2H), 3.56 (t, J = 4.8 Hz, 2H), 3.44 (t, J = 4.8 Hz, 2H), 2.38 (t, J = 4.4 Hz, 2H), 2.27 (t, J = 4.4 Hz, 2H), 2.21 (s, 3H) | 454 |
| 116 | Pre. Ex. 5 Ex. 117 | 8.29 (dd, J = 5.6, 5.6 Hz, 2H), 7.84 (s, 1H), 7.70 (d, J = 8.8 Hz, 2H), 7.47 (dd, J = 8.4, 7.6 Hz, 2H), 7.26 (dd, J = 7.6, 7.2 Hz, 1H), 7.14 (dd, J = 8.4, 7.2 Hz, 4H), 4.79 (d, J = 4.8 Hz, 1H), 4.68 (s, 2H), 4.51 (t, J = 5.6 Hz, 1H), 3.49 (dd, J = 11.6, 5.2 Hz, 1H), 3.31-3.23 (m, 3H), 3.02-2.96 (m, 1H) | 445 |

TABLE 2-continued

| Ex | Pre | ¹H-NMR (DMSO-d$_6$): δ (ppm) | MS(ESI+) |
|---|---|---|---|
| 117 | Pre. Ex. 5<br>Ex. 117 | 8.23 (t, J = 5.2 Hz, 1H), 7.84 (s, 1H), 7.70 (d, J = 8.23 (dd, J = 5.2, 5.2 Hz, 1H), 7.84 (s, 1H), 7.70 (d, J = 8.4 Hz, 2H), 7.47 (dd, J = 8.0, 7.6 Hz, 2H), 7.26 (dd, J = 7.6, 7.2 Hz, 1H), 7.14 (dd, J = 8.4, 7.2 Hz, 4H), 4.64 (s, 2H), 3.56 (t, J = 4.4 Hz, 4H), 3.20 (q, J = 6.4 Hz, 2H), 2.89 (s, 1H), 2.73 (s, 1H), 2.37-2.32 (m, 6H) | 484 |
| 118 | Pre. Ex. 5<br>Ex. 117 | 8.78 (dd, J = 6.0, 5.6 Hz, 1H), 7.85 (s, 1H), 7.70 (d, J = 8.8 Hz, 2H), 7.47 (dd, J = 8.4, 7.6 Hz, 2H), 7.26 (dd, J = 7.6, 6.8 Hz, 1H), 7.14 (dd, J = 8.8, 7.2 Hz, 4H), 4.72 (s, 2H), 3.90 (d, J = 5.6 Hz, 2H), 3.64 (s, 3H) | 443 |
| 119 | Pre. Ex. 5<br>Ex. 117 | 7.86 (s, 1H), 7.71 (d, J = 8.8 Hz, 2H), 7.47 (dd, J = 8.0, 7.6 Hz, 2H), 7.26 (dd, J = 7.6, 7.2 Hz, 1H), 7.14 (dd, J = 8.4, 8.0 Hz, 4H), 4.91 (d, J = 3.2 Hz, 2H), 4.31 (dd, J = 8.8, 4.0 Hz, 1H), 3.74-3.70 (m, 2H), 3.59 (s, 2H), 3.43-3.41 (m, 1H), 2.23-2.18 (m, 1H), 2.00-1.97 (m, 2H), 1.91-1.85 (m, 1H) | 483 |
| 120 | Pre. Ex. 5<br>Ex. 117 | 8.25 (dd, J = 5.6, 5.2 Hz, 1H), 7.84 (s, 1H), 7.70 (d, J = 9.2 Hz, 2H), 7.47 (dd, J = 8.4, 7.6 Hz, 2H), 7.26 (dd, J = 8.0, 7.2 Hz, 1H), 7.14 (dd, J = 8.4, 7.6 Hz, 4H), 4.63 (s, 2H), 4.43 (t, J = 5.2 Hz, 1H), 3.42-3.39 (m, 2H), 3.17-3.13 (m, 2H), 1.59-1.54 (m, 2H) | 429 |
| 121 | Pre. Ex. 5<br>Ex. 117 | 8.25 (dd, J = 5.6, 5.6 Hz, 1H), 7.84 (s, 1H), 7.70 (d, J = 8.8 Hz, 2H), 7.47 (dd, J = 8.0, 7.2 Hz, 2H), 7.26 (dd, J = 7.6, 7.2 Hz, 1H), 7.14 (dd, J = 7.6, 7.2 Hz, 4H), 4.63 (s, 2H), 4.41 (t, J = 5.2 Hz, 1H), 3.41-3.38 (m, 2H), 3.08-3.05 (m, 2H), 1.42 (t, J = 3.6 Hz, 4H) | 443 |
| 122 | Pre. Ex. 5<br>Ex. 117 | 7.86 (s, 1H), 7.71 (d, J = 8.8 Hz, 2H), 7.47 (dd, J = 8.0, 7.6 Hz, 2H), 7.26 (dd, J = 7.2, 7.2 Hz, 1H), 7.14 (dd, J = 8.8, 8.4 Hz, 4H), 5.12-4.99 (m, 1H), 4.88-4.80 (m, 2H), 4.39, 4.27 (s, 1H), 3.69-3.63 (m, 1H), 3.29-3.26 (m, 1H), 3.44-3.41 (m, 1H), 2.01-1.77 (m, 2H) | 441 |
| 123 | Pre. Ex. 5<br>Ex. 117 | 8.31 (s, 1H), 8.22 (dd, J = 5.6, 5.6 Hz, 1H), 7.84 (s, 1H), 7.70 (d, J = 8.8 Hz, 2H), 7.47 (dd, J = 8.4, 7.6 Hz, 2H), 7.26 (dd, J = 7.6, 7.2 Hz, 1H), 7.14 (dd, J = 8.8, 8.0 Hz, 4H), 4.66 (s, 2H), 3.19 (dd, J = 12.0, 6.0 Hz, 2H), 3.08-3.05 (m, 4H), 2.92-2.89 (m, 5H), 2.54 (t, J = 6.4 Hz, 2H) | 532 |
| 124 | Pre. Ex. 5<br>Ex. 117 | 8.15 (dd, J = 6.0, 5.6 Hz, 1H), 7.84 (s, 1H), 7.70 (d, J = 8.8 Hz, 2H), 7.47 (dd, J = 8.0, 8.0 Hz, 2H), 7.26 (dd, J = 8.8, 7.2 Hz, 1H), 7.14 (dd, J = 8.8, 7.6 Hz, 4H), 4.71 (s, 2H), 4.23 (s, 1H), 3.06 (d, J = 6.0 Hz, 2H), 1.54-1.17 (m, 11H) | 483 |
| 125 | Pre. Ex. 5<br>Ex. 117 | 12.70 (br, 1H), 7.83 (s, 1H), 7.78 (d, J = 8.4 Hz, 2H), 7.68 (d, J = 8.8 Hz, 2H), 7.49-7.42 (m, 4H), 7.26 (dd, J = 7.2, 7.2 Hz, 1H), 7.16-7.10 (m, 4H), 4.73 (s, 2H), 2.40 (s, 3H) | 525 |
| 126 | Pre. Ex. 5<br>Ex. 117 | 12.34 (br, 1H), 7.88 (s, 1H), 7.71 (d, 2H), 7.48 (dd, J = 8.0, 7.6 Hz, 2H), 7.26 (dd, J = 7.6, 7.2 Hz, 1H), 7.14 (dd, J = 8.4, 8.0 Hz, 4H), 4.80 (s, 2H), 3.24 (s, 3H) | 449 |
| 127 | Pre. Ex. 4<br>Ex. 1 | 7.65 (d, J = 8.4 Hz, 2H), 7.46 (dd, J = 8.4, 7.6 Hz, 2H), 7.25 (dd, J = 7.6, 6.8 Hz, 1H), 7.16-7.10 (m, 4H), 6.98-6.92 (m, 1H), 2.33-2.28 (m, 1H), 2.06-1.99 (m, 1H), 1.37-1.23 (m, 2H), 0.89-0.82 (m, 6H) | 428 |
| 128 | Pre. Ex. 3<br>Ex. 1 | 7.87 (s, 1H), 7.78 (d, J = 8.4 Hz, 2H), 7.70 (d, J = 8.8 Hz, 2H), 7.48 (dd, J = 8.4, 7.6 Hz, 4H), 7.34 (s, 2H), 7.26 (dd, J = 7.6, 7.2 Hz, 1H), 7.14 (dd, J = 7.6, 5.2 Hz, 4H), 5.31 (s, 2H) | 483 |
| 129 | Pre. Ex. 4<br>Ex. 1 | 7.85 (s, 1H), 7.69 (d, J = 8.8 Hz, 2H), 7.47 (dd, J = 8.4, 7.6 Hz, 2H), 7.33-7.24 (m, 6H), 7.13 (dd, J = 8.4, 6.4 Hz, 4H), 5.25 (s, 2H) | 404 |
| 130 | Pre. Ex. 4<br>Ex. 1 | 7.78 (s, 1H), 7.68 (d, J = 8.8 Hz, 2H), 7.47 (dd, J = 8.4, 7.6 Hz, 2H), 7.33-7.22 (m, 6H), 7.13 (dd, J = 8.4, 7.2 Hz, 4E), 4.24 (t, J = 7.6 Hz, 2H), 2.96 (t, J = 7.6 Hz, 2H) | 418 |
| 131 | Pre. Ex. 4<br>Ex. 1 | 7.84 (s, 1H), 7.68 (d, J = 9.2 Hz, 2H), 7.47 (dd, J = 8.4, 7.6 Hz, 2H), 7.26 (dd, J = 7.6, 7.2 Hz, 1H), 7.13 (dd, J = 8.8, 8.0 Hz, 4H), 6.92 (d, J = 1.6 Hz, 1H), 6.86 (dd, J = 8.0, 7.6 Hz, 2H), 5.99 (s, 2H), 5.14 (s, 2H)7.16-7.12 (m, 4H), 6.92 (d, J = 1.6 Hz, 1H), 6.88-6.84 (m, 2H), 5.99 (s, 2H), 5.14 (s, 2H) | 448 |
| 132 | Pre. Ex. 4<br>Ex. 1 | | 457 |
| 133 | Pre. Ex. 4<br>Ex. 1 | 7.71 (s, 1H), 7.65 (d, J = 8.8 Hz, 2H), 7.47 (dd, J = 8.4, 7.6 Hz, 2H), 7.25 (dd, J = 7.2, 7.2 Hz, 1H), 7.15-7.10 (m, 4H), 4.90 (t, J = 7.6 Hz, 1H), 2.32 (d, J = 12.0 Hz, 2H), 1.84 (d, J = 13.6 Hz, 2H), 1.70-1.64 (m, 3H), 1.36-1.26 (m, 2H), 1.22-1.16 (m, 1H) | 396 |

TABLE 2-continued

| Ex | Pre | ¹H-NMR (DMSO-d$_6$): δ (ppm) | MS(ESI+) |
|---|---|---|---|
| 134 | Pre. Ex. 4 Ex. 1 | 7.82 (s, 1H), 7.68 (d, J = 8.8 Hz, 2H), 7.47 (dd, J = 8.4, 7.6 Hz, 2H), 7.26 (dd, J = 7.6, 6.8 Hz, 1H), 7.13 (dd, J = 8.8, 7.6 Hz, 4H), 4.33-4.29 (m, 1H), 4.18-4.12 (m, 1H), 3.97 (dd, J = 11.2, 4.8 Hz, 1H), 3.78-3.72 (m, 1H), 3.65-3.60 (m, 1H), 1.96-1.89 (m, 2H), 1.83-1.80 (m, 1H), 1.72-1.66 (m, 1H) | 398 |
| 135 | Pre. Ex. 4 Ex. 1 | 7.80 (s, 1H), 7.68 (d, J = 8.4 Hz, 2H), 7.47 (dd, J = 8.0 Hz, 2H), 7.25 (dd, J = 7.6, 7.2 Hz, 1H), 7.13 (dd, J = 8.8, 7.6 Hz, 4H), 4.10 (t, J = 7.2 Hz, 2H), 3.38 (t, J = 6.0 Hz, 2H), 3.20 (s, 3H), 1.91-1.84 (m, 2H) | 386 |
| 136 | Pre. Ex. 3 Ex. 1 | 7.88 (s, 1H), 7.67 (d, J = 8.4 Hz, 2H), 7.47 (dd, J = 8.0, 7.6 Hz, 2H), 7.25 (dd, J = 7.2, 7.2 Hz, 1H), 7.13 (dd, J = 8.8, 8.0 Hz, 4H), 4.96-4.93 (m, 1H), 4.14 (t, J = 6.0 Hz, 2H), 3.66 (t, J = 6.0 Hz, 2H) | 358 |
| 137 | Pre. Ex. 3 Ex. 1 | 7.80 (s, 1H), 7.67 (d, J = 8.8 Hz, 2H), 7.47 (dd, J = 8.4, 7.6 Hz, 2H), 7.26 (dd, J = 7.6, 7.2 Hz, 1H), 7.13 (dd, J = 8.8, 7.6 Hz, 4H), 4.04 (t, J = 7.2 Hz, 2H), 3.41 (t, J = 6.4 Hz, 2H), 1.72-1.64 (m, 2H), 1.47-1.40 (m, 2H) | 386 |
| 138 | Pre. Ex. 3 Ex. 1 | 7.79 (s, 1H), 7.67 (d, J = 8.8 Hz, 2H), 7.47 (dd, J = 8.4, 7.6 Hz, 2H), 7.25 (dd, J = 7.6, 7.2 Hz, 1H), 7.13 (dd, J = 8.8, 7.6 Hz, 4H), 4.58 (t, J = 5.2 Hz, 1H), 4.10 (t, J = 7.6 Hz, 2H), 3.47 (dd, J = 11.2, 6.0 Hz, 2H), 1.82-1.75 (m, 2H) | 372 |
| 139 | Pre. Ex. 3 Ex. 1 | 7.77 (s, 1H), 7.67 (d, J = 8.4 Hz, 2H), 7.47 (dd, J = 8.4, 7.6 Hz, 2H), 7.25 (dd, J = 7.6, 7.2 Hz, 1H), 7.13 (dd, J = 7.6, 6.0 Hz, 4H), 4.34 (s, 1H), 4.06 (s, 2H), 1.54-1.06 (m, 10H) | 426 |
| 140 | Pre. Ex. 4 Ex. 1 | 7.84 (s, 1H), 7.73 (d, J = 8.8 Hz, 2H), 7.57-7.46 (m, 6H), 7.42 (dd, J = 8.4, 1.6 Hz, 2H), 7.26 (dd, J = 8.4, 6.4 Hz, 1H), 7.17-7.13 (m, 3H) | 390 |
| 141 | Pre. Ex. 3 Ex. 1 | 7.81 (s, 1H), 7.71 (d, J = 8.8 Hz, 2H), 7.48 (dd, J = 8.8, 7.6 Hz, 2H), 7.26 (dd, J = 7.6, 7.2 Hz, 1H), 7.18-7.13 (m, 6H), 6.89 (d, J = 8.8 Hz, 2H) | 406 |
| 142 | Pre. Ex. 4 Ex. 1 | 13.23 (s, 1H), 8.10 (d, J = 8.8 Hz, 2H), 7.85 (s, 1H), 7.73 (d, J = 8.8 Hz, 2H), 7.58 (d, J = 8.8 Hz, 2H), 7.48 (dd, J = 8.4, 7.6 Hz, 2H), 7.27 (dd, J = 7.6, 6.8 Hz, 1H), 7.16-7.14 (m, 4H) | 434 |
| 143 | Pre. Ex. 4 Ex. 1 | 7.85 (s, 1H), 7.74 (dd, J = 9.6, 8.4 Hz, 4H), 7.48 (dd, J = 8.4, 7.6 Hz, 2H), 7.37 (d, J = 8.8 Hz, 2H), 7.26 (dd, J = 7.6, 6.4 Hz, 1H), 7.17-7.13 (m, 4H) | 470 |
| 144 | Pre. Ex. 4 Ex. 1 | 8.52 (d, J = 6.0 Hz, 2H), 7.87 (s, 1H), 7.71 (d, J = 8.8 Hz, 2H), 7.47 (dd, J = 8.4, 7.6 Hz, 2H), 7.29-7.27 (m, 3H), 7.16-7.13 (m, 4H), 5.27 (s, 2H) | 462 |
| 145 | Pre. Ex. 4 Ex. 1 | 7.93 (d, J = 8.4 Hz, 2H), 7.87 (s, 1H), 7.70 (d, J = 8.8 Hz, 2H), 7.49-7.43 (m, 4H), 7.26 (dd, J = 7.6, 6.4 Hz, 1H), 7.14 (dd, J = 7.6, 5.6 Hz, 4H), 5.32 (s, 2H), 3.84 (s, 3H) | |
| 146 | Pre. Ex. 4 Ex. 1 | 7.91 (d, J = 8.4 Hz, 2H), 7.87 (s, 1H), 7.71 (d, J = 8.8 Hz, 2H), 7.47 (dd, J = 8.4, 7.6 Hz, 2H), 7.42 (d, J = 8.4 Hz, 2H), 7.26 (dd, J = 7.6, 6.4 Hz, 1H), 7.14 (dd, J = 7.6, 6.0 Hz, 4H), 5.31 (s, 2H) | 448 |
| 147 | Pre. Ex. 4 Ex. 1 | 8.00 (d, J = 4.8 Hz, 1H), 7.86 (s, 1H), 7.74 (d, J = 8.8 Hz, 2H), 7.66 (d, J = 8.8 Hz, 2H), 7.54 (s, 2H), 7.48 (dd, J = 8.4, 7.2 Hz, 2H), 7.27 (dd, J = 7.6, 7.2 Hz, 1H), 7.17-7.14 (m, 4H) | 469 |
| 148 | Pre. Ex. 4 Ex. 1 | 7.98 (d, J = 9.2 Hz, 1H), 7.93 (dd, J = 1.6, 1.6 Hz, 1H), 7.84 (s, 1H), 7.78 (dd, J = 8.0, 7.6 Hz, 1H), 7.74 (d, J = 8.8 Hz, 2H), 7.70-7.68 (m, 1H), 7.57 (s, 2H), 7.48 (dd, J = 8.4, 7.6 Hz, 2H), 7.27 (dd, J = 7.6, 6.8 Hz, 1H), 7.17-7.14 (m, 4H) | 469 |
| 149 | Pre. Ex. 4 Ex. 1 | 7.78 (s, 1H), 7.68 (d, J = 8.8 Hz, 2H), 7.47 (dd, J = 8, 4, 7.6 Hz, 2H), 7.25 (dd, J = 7.6, 7.2 Hz, 1H), 7.14 (dd, J = 10.8, 8.8 Hz, 4H), 4.88 (s, 2H) | 408 |
| 150 | Pre. Ex. 4 Ex. 1 | 7.80 (s, 1H), 7.68 (d, J = 8.8 Hz, 2H), 7.46 (dd, J = 8.4, 7.6 Hz, 2H), 7.25 (dd, J = 7.6, 6.8 Hz, 1H), 7.13 (dd, J = 9.6, 7.6 Hz, 4H), 4.23 (t, J = 6.4 Hz, 2H), 3.98 (t, J = 6.4 Hz, 2H) | 438 |
| 151 | Pre. Ex. 4 Ex. 1 | 7.80 (s, 1H), 7.68 (d, J = 8.8 Hz, 2H), 7.47 (dd, J = 8.4, 7.6 Hz, 2H), 7.26 (dd, J = 7.6, 7.2 Hz, 1H), 7.13 (dd, J = 8.8, 7.6 Hz, 4H), 3.90 (d, J = 7.2 Hz, 2H), 2.12-2.06 (m, 1H), 1.88-1.85 (m, 3H), 1.66-1.63 (m, 2H), 1.24-1.16 (m, 2H), 1.10-1.01 (m, 2H) | 454 |
| 152 | Pre. Ex. 4, 6 Ex. 1 | 8.01 (s, 1H), 7.54 (d, J = 8.4, 6.8 Hz, 1H), 7.45 (d, J = 7.2 Hz, 1H), 7.32-7.27 (m, 3H), 7.16 (dd, J = 7.6, 7.6 Hz, 1H), 7.00 (d, J = 7.6 Hz, 2H), 6.95 (dd, J = 7.6, 7.2 Hz, 1H), 4.49 (t, J = 2.4 Hz, 2H), 4.38 (t, J = 2.4 Hz, 2H), 3.93-3.91 (m, 4H), 2.64 (br, 2H), 2.08-2.03 (m, 1H), 1.56-1.54 (m, 2H), 1.39 (s, 9H), 1.11-1.07 (m, 2H) | 555 |

TABLE 2-continued

| Ex | Pre | $^1$H-NMR (DMSO-$d_6$): δ (ppm) | MS(ESI+) |
|---|---|---|---|
| 153 | Ex. 152, de-Boc reaction | 8.74 (br, 2H), 8.02 (s, 1H), 7.56 (dd, J = 8.8, 7.2 Hz, 1H), 7.46 (dd, J = 8.8, 2.8 Hz, 1H), 7.33-7.28 (m, 3H), 7.16 (dd, J = 7.6, 7.6 Hz, 1H), 7.01-6.94 (m, 3H), 4.49 (dd, J = 4.8, 3.2 Hz, 2H), 4.38 (dd, J = 3.2, 1.2 Hz, 2H), 3.94 (d, J = 7.2 Hz, 2H), 3.22 (d, J = 12.8 Hz, 2H), 2.79 (dd, J = 10.4, 2.4 Hz, 2H), 2.18-2.13 (m, 1H), 1.74 (d, J = 12.8 Hz, 2H), 1.50-1.40 (m, 2H) | 455 |
| 154 | Ex. 153, 79 | 8.02 (s, 1H), 7.54 (ddd, J = 2.6, 2.6, 2.4 Hz, 1H), 7.46 (dd, J = 4.4, 3.2 Hz, 1H), 7.32-7.28 (m, 3H), 7.16 (dd, J = 7.6, 7.6 Hz, 1H), 7.01-6.94 (m, 3H), 4.49 (dd, J = 4.8, 3.2 Hz, 2H), 4.37 (dd, J = 7.6, 5.2 Hz, 2H), 4.29 (d, J = 12.4 Hz, 1H), 4.04 (dd, J = 22.8, 8.8 Hz, 2H), 3.93 (d, J = 7.6 Hz, 2H), 3.72 (d, J = 13.6 Hz, 1H), 3.26 (s, 3H), 2.88 (t, J = 12.4 Hz, 1H), 2.16-2.11 (m, 1H), 1.59 (d, J = 12.8 Hz, 2H), 1.207-1.06 (m, 3H) | 527 |
| 155 | Pre. Ex. 4, 6 Ex. 1 | 8.00 (d, J = 18.8 Hz, 1H), 7.53 (br, 1H), 7.43 (dd, J = 10.0, 8.4 Hz, 1H), 7.29 (dd, J = 8.0, 3.6 Hz, 3H), 7.16 (dd, J = 7.6, 7.6 Hz, 1H), 7.03-6.95 (m, 3H), 4.49 (s, 2H), 4.38-4.31 (m, 3H), 4.23-4.11 (m, 1H), 3.90 (d, J = 12.8 Hz, 1H), 3.21-3.19 (m, 2H), 1.99-1.86 (m, 3H), 1.73 (d, J = 10.4 Hz, 1H), 1.23 (s, 9H) | 541 |
| 156 | Ex. 155, de-Boc reaction | 9.50 (s, 1H), 8 (br, 1H), 8.04 (s, 1H), 7.55 (ddd, J = 4.6, 4.6, 3.2 Hz, 1H), 7.47 (dd, J = 4.4, 3.2 Hz, 1H), 7.31 (dd, J = 8.0, 7.6 Hz, 3H), 7.17 (dd, J = 7.6, 7.6 Hz, 1H), 7.02-6.94 (to, 3H), 5.00 (dd, J = 8.4, 3.2 Hz, 2H), 4.41-4.28 (m, 4H), 3.28-3.25 (m, 1H), 3.11-3.05 (m, 1H), 2.09-1.71 (m, 5H) | 441 |
| 157 | Pre. Ex. 3, 6 Ex. 1 | 8.05 (s, 1H), 7.64 (ddd, J = 15.6, 15.6, 1.6 Hz, 1H), 7.47 (dd, J = 8.0, 1.6 Hz, 1H), 7.36-7.26 (m, 8H), 7.16 (dd, J = 7.6, 7.2 Hz, 1H), 6.99 (dd, J = 8.81.6 Hz, 2H), 6.93 (dd, J = 7.6, 6.8 Hz, 1H), 5.23 (s, 2H), 4.50-4.48 (m, 2H), 4.39-4.36 (m, 2H) | 448 |
| 158 | Pre. Ex. 4, 6 Ex. 1 | 8.02 (s, 3H), 7.54 (ddd, J = 16.0, 16.0, 1.6 Hz, 1H), 7.46 (dd, J = 8.0, 1.2 Hz, 1H), 7.33-7.29 (m, 3H), 7.17 (dd, J = 7.6, 7.6 Hz, 1H), 7.01 (dd, J = 8.8, 1.2 Hz, 2H), 6.96 (dd, J = 8.0, 7.2 Hz, 1H), 4.49 (t, J = 2.4 Hz, 2H), 4.38 (t, J = 2.4 Hz, 2H), 4.27 (t, J = 2.0 Hz, 2H), 3.13 (t, J = 6.0 Hz, 2H) | 401 |
| 159 | Ex. 158, 79 | 8.86 (t, J = 6.0 Hz, 1H), 8.01-7.99 (m, 3H), 7.93 (d, J = 8.4 Hz, 2H), 7.53 (ddd, J = 4.4, 4.4, 3.2 Hz, 1H), 7.45 (dd, J = 7.2, 1.2 Hz, 1H), 7.31-7.27 (m, 3H), 7.16 (dd, J = 7.6, 7.2 Hz, 1H), 7.00-6.92 (m, 3H), 4.48 (dd, J = 8.4, 3.6 Hz, 2H), 4.37 (dd, J = 7.6, 2.4 Hz, 2H), 4.26 (dd, J = 5.6, 4.8 Hz, 2H), 3.64 (dd, J = 8.0, 5.6 Hz, 2H), 3.24 (s, 3H) | 583 |
| 160 | Pre. Ex. 6 Ex. 1 | 8.03 (s, 1H), 7.53 (ddd, J = 4.6, 4.6, 1.6 Hz, 1H), 7.47 (dd, J = 8.4, 1.2 Hz, 1H), 7.29 (dd, J = 8.0, 7.2 Hz, 3H), 7.16 (dd, J = 7.6, 7.2 Hz, 1H), 7.00 (dd, J = 4.8, 0.8 Hz, 2H), 6.94 (dd, J = 7.2, 7.2 Hz, 1H), 4.54 (s, 2H), 4.49 (t, J = 2.4 Hz, 2H), 4.39-4.37 (m, 2H) | 416 |
| 161 | Ex. 160, 117 | 8.05 (s, 1H), 7.55 (ddd, J = 15.6, 15.6, 2.4 Hz, 1H), 7.48 (dd, J = 8.0, 2.4 Hz, 1H), 7.32-7.28 (m, 3H), 7.17 (dd, J = 7.6, 7.6 Hz, 1H), 7.00 (dd, J = 8.8, 0.8 Hz, 2H), 6.95 (dd, J = 7.2, 6.8 Hz, 3H), 4.90-4.88 (m, 2H), 4.51-4.49 (m, 2H), 4.39-4.37 (m, 2H), 4.32-4.29 (m, 1H), 3.73-3.66 (m, 2H), 3.58 (s, 2H), 3.-3. (m, 1H), 2.19-2.17 (m, 1H), 2.00-1.96 (m, 2H), 1.89-1.85 (m, 1H) | 527 |
| 162 | Ex. 156, 79 | 8.00 (s, 1H), 7.53 (ddd, J = 15.6, 15.6, 1.6 Hz, 1H), 7.44 (dd, J = 8.0, 1.2 Hz, 1H), 7.33-7.27 (m, 3H), 7.16 (dd, J = 7.6, 7.2 Hz, 1H), 7.01 (dd, J = 8.8, 0.8 Hz, 2H), 6.95 (dd, J = 7.6, 7.2 Hz, 1H), 4.49-4.48 (m, 2H), 4.40-4.37 (m, 2H), 4.23-4.19 (m, 2H), 3.91-3.89 (m, 1H), 3.28-3.25 (m, 2H), 2.80 (s, 3H), 1.99-1.93 (m, 3H), 1.76-1.74. (m, 1H) | 519 |
| 163 | Ex. 156, 163 | | 524 |
| 164 | Pre. Ex. 3, 6 Ex. 1 | 8.06 (s, 1H), 7.77 (d, J = 7.6 Hz, 2H), 7.55 (ddd, J = 15.6, 15.6, 1.6 Hz, 1H), 7.49-7.47 (m, 3H), 7.34 (s, 2H), 7.28 (dd, J = 8.8, 7.6 Hz, 3H), 7.17 (dd, J = 7.6, 7.6 Hz, 1H), 6.99 (dd, J = 8.4, 0.8 Hz, 2H), 6.94 (dd, J = 7.2, 6.8 Hz, 3H), 5.28 (s, 2H), 4.51-4.49 (m, 2H), 4.39-4.37 (m, 2H) | 527 |
| 165 | Ex. 160, 117 | 8.04 (s, 1H), 7.55 (dd, J = 7.6, 7.2 Hz, 1H), 7.48 (d, J = 7.6 Hz, 1H), 7.30 (dd, J = 8.0, 8.0 Hz, 3H), 7.17 (dd, J = 7.6, 7.6 Hz, 1H), 7.01-6.93 (m, 4H), 4.93-4.72 (m, 2H), 4.49 (br, 2H), 4.39-4.38 (m, 3H), 4.24-4.21 (m, 1H), 3.71-3.64 (m, 2H), 3.41-3.38 (m, 1H), 2.19-2.12 (m, 1H), 1.97 (t, J = 6.4 Hz, 1H), 1.91-1.86 (m, 1H) | 513 |

Example 168

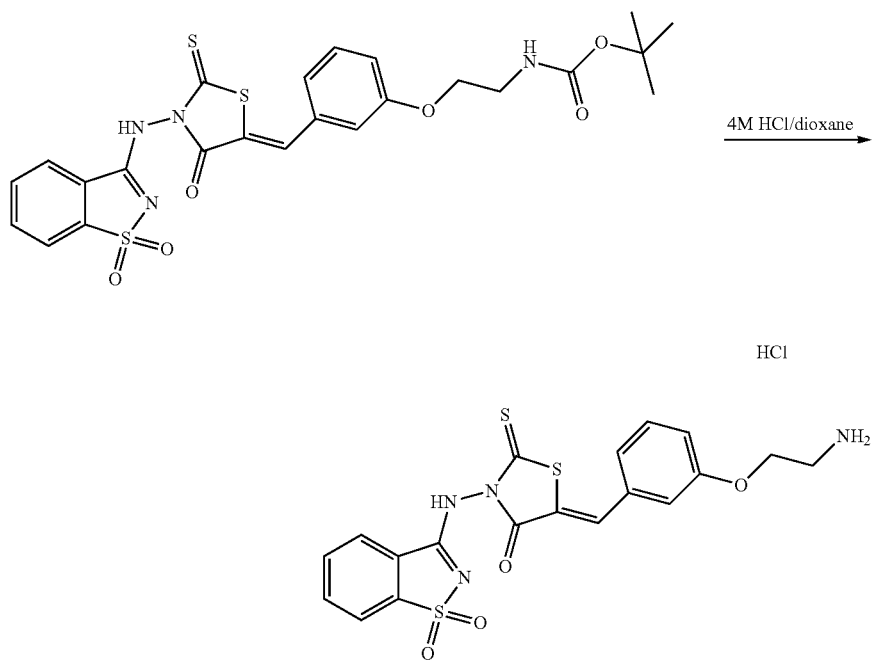

3-[(4-Oxo-5-(3-(2-t-butoxycarbonylaminoethyloxy)benzylidene)-2-thioxothiazolidin-3-yl)amino]-1,2-benzothiazole 1,1-dioxide (220 mg) obtained in Example 167 was dissolved in 4M hydrogen chloride-ethyl acetate solution (10 ml), and the solution was stirred at room temperature for 3 hr, and concentrated under reduced pressure to give 3-[(4-oxo-5-(3-(2-aminoethyloxy)benzylidene)-2-thioxothiazolidin-3-yl)amino]-1,2-benzothiazole 1,1-dioxide hydrochloride (167 mg).

Example 179

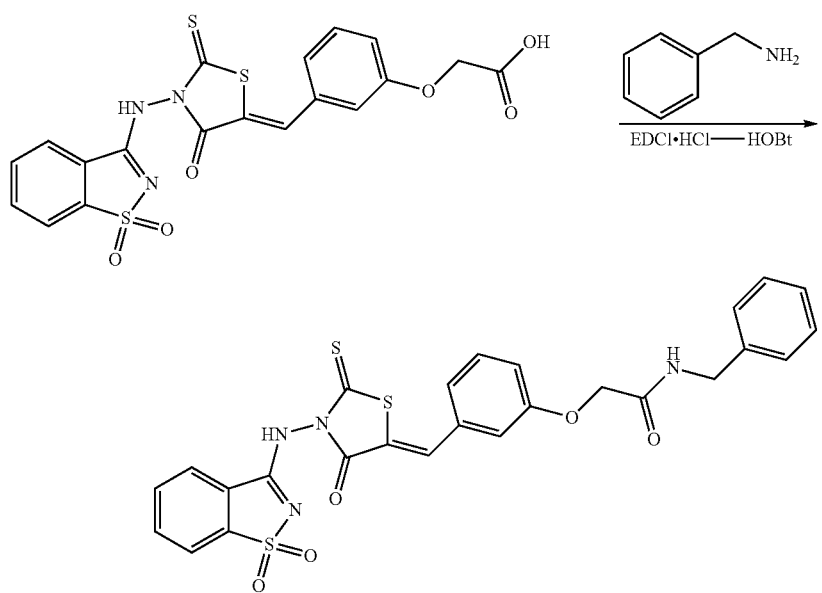

To a solution of 3-[(4-oxo-5-(3-(carboxymethyloxy)benzylidene)-2-thioxothiazolidin-3-yl)amino]-1,2-benzothiazole 1,1-dioxide (34 mg) obtained in Example 174 and benzylamine (8 mg) in N,N-dimethylformamide (1 ml) were added 1-hydroxybenzotriazole (10 mg) and 1-ethyl-3-(3-dimethylaminopropyl)carbodiimide hydrochloride (14 mg) with stirring under ice cooling, and the mixture was stirred overnight at room temperature. The reaction mixture was poured into ice water (20 ml), and the mixture was extracted with ethyl acetate (30 ml). The extract was washed successively with 0.5M aqueous sodium hydrogen carbonate solution and saturated brine, dried over anhydrous sodium sulfate, and concentrated under reduced pressure to give 3-[(4-oxo-5-(3-(benzyl aminocarbonylmethyloxy)benzylidene)-2-thioxothiazolidin-3-yl)amino]-1,2-benzothiazole 1,1-dioxide (34 mg).

The following compounds were produced using each corresponding raw material compound according to the method described in Example 1, 117, 79, 163, 168 or 179 and a method known per se. The corresponding raw material compounds were commercially available products, or were produced according to a method known per se or the methods described in Preparation Examples 1-7. The structure formulas of the compounds are shown in Table 3, and the physicochemical data are shown in Table 4.

$R^1$ means —Y-A and $R^2$ means —Z—B in the tables.

The following abbreviations are used in the tables.

Pre: the raw material compound (the number of Preparation Example) which was used for the objective compound, and the number of Example that the objective compound was produced according to.

Ex: the number of Example

TABLE 3

List of Compound of Examples

| Ex | $R^1-$ | $R^2-$ |
|---|---|---|
| 166 | | |
| 167 | | |
| 168 | | |
| 169 | | |
| 170 | | |
| 171 | | |

TABLE 3-continued

List of Compound of Examples

| Ex | R¹— | R²— |
|---|---|---|
| 172 | 2-methylphenoxyethylamine · HCl | 3-aminobenzisothiazole 1,1-dioxide |
| 173 | tert-butyl 2-(3-methylphenoxy)acetate | 3-aminobenzisothiazole 1,1-dioxide |
| 174 | 2-(3-methylphenoxy)acetic acid | 3-aminobenzisothiazole 1,1-dioxide |
| 175 | tert-butyl 2-(4-methylphenoxy)acetate | 3-aminobenzisothiazole 1,1-dioxide |
| 176 | 2-(4-methylphenoxy)acetic acid | 3-aminobenzisothiazole 1,1-dioxide |
| 177 | tert-butyl 2-(2-methylphenoxy)acetate | 3-aminobenzisothiazole 1,1-dioxide |
| 178 | 2-(2-methylphenoxy)acetic acid | 3-aminobenzisothiazole 1,1-dioxide |

TABLE 3-continued

List of Compound of Examples

| Ex | R¹— | R²— |
|----|-----|-----|
| 179 | (3-methylphenoxy)-N-benzylacetamide group | N-methyl-benzisothiazole-1,1-dioxide-3-amine group |
| 180 | 4-(phenoxy)-4-methylphenyl group | N-(2-aminoethyl)propanamide group |

TABLE 4

| Ex | Pre | ¹H-NMR (DMSO-d$_6$): δ (ppm) | MS(ESI+) |
|----|-----|------------------------------|----------|
| 166 | Pre. Ex. 1 Ex. 1 | 8.28-8.26 (m, 1H), 8.12-8.10 (m, 1H), 7.97-7.94 (m, 2H), 7.78-7.75 (m, 3H), 7.55-7.45 (m, 4H), 7.27-7.21 (m, 1H) ppm. | 428 |
| 167 | Pre. Ex. 1, 6 Ex. 1 | 8.24 (dd, J = 2.8, 2.4 Hz, 1H), 8.08-8.06 (m, 1H), 7.99 (s, 1H), 7.94-7.92 (m, 2H), 7.53-7.49 (dd, J = 8.0, 8.0 Hz, 1H), 7.29 (d, J = 7.6 Hz, 2H), 7.15 (m, 1H), 7.04 (bs, 1H), 4.05 (m, 2H), 3.34 (m, 2H), 1.39 (s, 9H) ppm. | 561 |
| 168 | Ex. 167, 168 | 8.32 (bs, 1H), 8.12 (bs, 3H), 8.05 (dd, J = 5.6, 2.8 Hz, 1H), 8.00 (s, 1H), 7.92-7.90 (m, 2H), 7.55 (dd, J = 8.0, 8.0 Hz, 1H), 7.37-7.32 (m, 1H), 7.31 (s, 1H), 7.22-7.19 (m, 1H), 4.27 (d, J = 4.8 Hz, 2H), 3.28 (d, J = 4.8 Hz, 2H) ppm. | 461 |
| 169 | Pre. Ex. 1, 6 Ex. 1 | 8.27-8.26 (m, 1H), 8.11-8.09 (m, 1H), 7.99-7.94 (m, 3H), 7.71 (d, J = 8.8 Hz, 2H), 7.16 (d, J = 8.8 Hz, 1H), 7.06 (dd, J = 5.6, 5.2 Hz, 1H), 4.09 (t, J = 5.6 Hz, 2H), 3.34 (t, J = 5.6 Hz, 2H), 1.39 (s, 9H) ppm. | 561 |
| 170 | Ex. 169, 168 | 8.34-8.33 (m, 1H), 8.33 (bs, 3H), 8.08-8.06 (m, 1H), 7.99 (s, 1H), 7.94-7.92 (m, 2H), 7.74 (d, J = 8.8 Hz, 2H), 7.21 (d, J = 8.8 Hz, 2H), 4.30 (t, J = 4.8 Hz, 2H), 3.26 (t, J = 5.2 Hz, 2H) ppm. | 461 |
| 171 | Pre. Ex. 1, 6 Ex. 1 | 8.28-8.26 (m, 1H), 8.16 (s, 1H), 8.10-8.08 (m, 1H), 7.96-7.93 (m, 2H), 7.57-7.53 (m, 2H), 7.23-7.12 (m, 3H), 4.18 (t, J = 5.2 Hz, 2H), 3.37 (t, J = 5.2 Hz, 2H), 1.37 (s, 9H) ppm. | 561 |
| 172 | Ex. 171, 168 | 8.42 (bs, 1H), 8.30 (s, 1H), 8.22 (bs, 3H), 8.08-8.06 (m, 1H), 7.95-7.91 (m, 2H), 7.60-7.56 (m, 2H), 7.26-7.19 (m, 2H), 4.37-4.35 (m, 2H), 3.31 (bs, 2H) ppm. | 461 |
| 173 | Pre. Ex. 1, 6 Ex. 1 | 8.22 (dd, J = 3.2, 2.4 Hz, 1H), 8.05 (s, 1H), 7.96-7.90 (m, 2H), 7.51 (dd, J = 8.0, 8.0 Hz, 1H), 7.33 (d, J = 7.6 Hz, 1H), 7.23 (d, J = 2.0 Hz, 1H), 7.14 (s, 1H), 7.12 (d, J = 6.4 Hz, 1H), 4.78 (s, 2H), 1.46 (s, 9H) ppm. | 532 |
| 174 | Ex. 173, 168 | 8.26-8.24 (m, 1H), 8.08-8.06 (m, 1H), 7.99 (s, 1H), 7.95-7.92 (m, 2H), 7.52 (dd, J = 8.0, 8.0 Hz, 1H), 7.30 (dd, J = 12.0, 7.6 Hz, 1H), 7.27 (s, 1H), 7.15-7.13 (m, 1H), 4.79 (s, 2H) ppm. | 476 |
| 175 | Pre. Ex. 1, 6 Ex. 1 | 8.24-8.21 (m, 1H), 8.06-8.04 (m, 1H), 7.96 (s, 1H), 7.92-7.90 (m, 2H), 7.70 (d, J = 8.8 Hz, 2H), 7.13 (d, J = 8.8 Hz, 2H), 4.80 (s, 2H), 1.44 (s, 9H) ppm. | 532 |
| 176 | Ex. 175, 168 | 8.27-8.26 (m, 1H), 8.12-8.09 (m, 1H), 8.00 (s, 1H), 7.98-7.93 (m, 2H), 7.71 (d, J = 8.8 Hz, 2H), 7.15 (d, J = 9.2 Hz, 2H), 4.81 (s, 2H) ppm. | 476 |
| 177 | Pre. Ex. 1, 6 Ex. 1 | 8.24-8.22 (m, 1H), 8.17 (s, 1H), 8.06-8.04 (m, 1H), 7.92-7.90 (m, 2H), 7.59-7.53 (m, 2H), 7.19 (dd, J = 7.6, 7.6 Hz, 1H), 7.11 (d, J = 8.4 Hz, 1H), 4.90 (s, 2H), 1.43 (s, 9H) ppm. | 532 |

TABLE 4-continued

| Ex | Pre | ¹H-NMR (DMSO-d₆): δ (ppm) | MS(ESI+) |
|---|---|---|---|
| 178 | Ex. 177, 168 | 8.30-8.27 (m, 1H), 8.19 (s, 1H), 8.12-8.09 (m, 1H), 7.98-7.93 (m, 2H), 7.60 (m, 2H), 7.20-7.11 (m, 1H), 7.03-7.01 (m, 1H), 4.95 (s, 2H) ppm. | 476 |
| 179 | Ex. 174, 179 | 8.75 (dd, J = 6.0 Hz, 1H), 8.22-8.20 (m, 1H), 8.04-8.02 (m, 1H), 7.93 (s, 1H), 7.91-7.89 (m, 2H), 7.63 (dd, J = 8.0, 8.0 Hz, 1H), 7.42-7.17 (m, 8H), 4.68 (s, 2H), 4.37 (d, J = 6.0 Hz, 2H) ppm | 565 |
| 180 | Pre. Ex. 5 Ex. 117, 168 | 8.61 (bs, 1H), 7.95 (bs, 3H), 7.85 (s, 1H), 7.72-7.70 (m, 2H), 7.50-7.46 (m, 2H), 7.28-7.25 (m, 1H), 7.16-7.12 (m, 4H), 4.70 (s, 2H), 3.35-3.31 (m, 2H), 2.85 (t, J = 6.8 Hz, 2H) ppm. | 414 |

| Formulation Example 1 (production of capsule) | |
|---|---|
| 1) compound of Example 1 | 30 mg |
| 2) finely divided powder cellulose | 10 mg |
| 3) lactose | 19 mg |
| 4) magnesium stearate | 1 mg |
| Total | 60 mg |

1), 2), 3) and 4) are mixed and filled in a gelatin capsule.

| Formulation Example 2 (production of tablet) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

Biochemical Evaluation Test for Activity: In Vitro Binding Assay

1) A fusion protein of Raf (target protein of Ras) and GST (glutathione S-transferase) was expressed in *Escherichia coli* using GST fusion protein expression vector (pGEX-6P-1 vector (GE Healthcare)). The expressed GST-Raf fusion protein was immobilized on an affinity carrier for purification (glutathione Sepharose 4B: resin (GE Healthcare)).

2) Radioisotope-labeled Ras
GTPγ[$^{35}$S] (Perkin Elmer), which is one of the GTP analogs, was added to Ras in which GST tag was cleaved using GST fusion protein cleavage protease (PreScission protease (GE Healthcare)) to prepare radioisotope-labeled Ras.

3) Measurement of Ras-Raf binding inhibition activity
GST-Raf fusion protein immobilized on the resin in the above-mentioned 1) and the radioactive Ras prepared in the above-mentioned 2) were incubated in the presence of various concentrations of a compound dissolved in 10% DMSO to promote the binding reaction between Ras and Raf. The resin in the reaction solution was washed, and then, the complex of GST-Raf fusion protein and radioactive Ras was eluted by adding glutathione. The binding activity between Ras and Raf was measured by scintillation counting of the radioactivity of the eluate. Thus, the Ras-Raf binding inhibition activity by addition of various compounds was evaluated. $IC_{50}$ (μM) of the representative Example compounds of the present invention are shown in the following Table 5.

TABLE 5

| Ex | $IC_{50}$ (μM) |
|---|---|
| 1 | 70 |
| 6 | 400 |
| 7 | 200 |
| 12 | 50 |
| 13 | 100 |
| 16 | 100 |
| 53 | 160 |
| 55 | 100 |
| 56 | 90 |
| 167 | 360 |

Experimental Example 2

Cytological Evaluation Test for Activity: Cell-Based Assay

Medium containing 0.33% SeaPlaque® agarose (Lonza, Rockland, Inc., ME, USA) and a mixture of compound and cell line having an active form mutation of any of H-Ras, N-Ras and H-Ras was plated, laying on cell medium containing 0.6% SeaPlaque® agarose. It was then cultured at 37° C. for 2 weeks. Colony formation inhibition activity (anchorage-independent cell growth inhibition activity) was evaluated by using, as a control, the number of colonies having 50 μm or more in diameter formed in the sample plated as a layer of medium containing a cell line but not a compound, and by calculating colony formation inhibition rate of a test compound in soft agar. $IC_{50}$ (μM) of compounds of the present invention are shown in the following Table 6.

TABLE 6

| Ex | tumor cell growth inhibition activity |
|---|---|
| 1 | (+++) |
| 6 | (+++) |
| 7 | (++) |
| 12 | (+++) |
| 13 | (+++) |
| 16 | (+++) |
| 53 | (++) |
| 56 | (+++) |
| 79 | (+++) |
| 86 | (+++) |
| 90 | (+++) |
| 128 | (+++) |
| 164 | (+++) |

TABLE 6-continued

| Ex | tumor cell growth inhibition activity |
|---|---|
| 167 | (++) |
| 168 | (++) |
| 173 | (++) |
| 174 | (++) |
| 180 | (++) |

Experimental Example 3

Biological Evaluation Test for Activity: In Vivo Assay

A cell suspension (about $2\times10^6$ cells) of human colorectal cancer cell line, SW480, which has active form of K-Ras, was subcutaneously inoculated and implanted with a syringe at the right flank of 6 to 8-week-old nude mice (female). After a tumor grew to the grossly recognizable size (40-100 mm³), a compound (80 mg/kg) dissolved in a solvent (Cremophor EL:Ethanol:Water=1:1:6) was orally administered once a day for five consecutive days per week. This is considered as the compound administration group. A solvent alone was administered to control group in the same manner. After the compound administration started, tumor volumes of both the groups were measured twice a week. Tumor growth inhibition rates were calculated by comparing tumor volumes of control group (100%) and those of compound administration group after three-week administration to evaluate anticancer activity of a compound. The tumor growth inhibition rates in the case of orally administering compounds of the present invention at 80 mg/Kg are shown in the following Table 7.

TABLE 7

| Example compound | tumor growth inhibition rate (%) |
|---|---|
| 1 | 88 |
| 6 | 85 |
| 7 | 85 |
| 12 | 86 |
| 13 | 70 |
| 16 | 69 |
| 56 | 62 |
| 90 | 62 |

INDUSTRIAL APPLICABILITY

Since the present invention compound has a Ras function inhibitory action, it is useful as an anticancer drug.

The invention claimed is:

1. A compound represented by the formula (I):

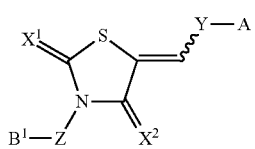

(I)

wherein
A is
(1) a $C_{6-10}$ aryl group optionally substituted by the substituent(s) selected from
  (i) a carboxy group,
  (ii) a $C_{1-6}$ alkoxy group substituted by the substituent(s) selected from
    (a) a $C_{6-10}$ aryloxy group optionally substituted by the substituent(s) selected from a halogen atom, a $C_{1-6}$ alkyl group and a nitro group,
    (b) an amino group optionally mono- or di-substituted by $C_{1-6}$ alkoxy-carbonyl group(s),
    (c) a carboxy group,
    (d) a $C_{1-6}$ alkoxy-carbonyl group,
    (e) a carbamoyl group optionally mono- or di-substituted by $C_{7-13}$ aralkyl group(s), and
    (f) a heterocyclic group,
  (iii) a $C_{6-10}$ aryl group optionally substituted by nitro group(s),
  (iv) a $C_{6-10}$ aryloxy group optionally substituted by the substituent(s) selected from a halogen atom, a nitro group, a $C_{1-6}$ alkyl group, a $C_{1-6}$ alkoxy group and a cyano group,
  (v) a $C_{7-13}$ aralkyl group,
  (vi) a $C_{7-13}$ aralkyloxy group,
  (vii) a $C_{6-10}$ aryl-$C_{2-6}$ alkenyl group,
  (viii) a heterocyclic group,
  (ix) a heterocyclyloxy group,
  (x) a heterocyclylcarbonyl group, and
  (xi) an amino group optionally mono- or di-substituted by $C_{6-10}$ aryl group(s),
(2) fluorenyl, furyl, pyridyl or carbazolyl, each of which is optionally substituted by the substituent(s) selected from
  (i) a halogen atom,
  (ii) a carboxy group,
  (iii) a $C_{1-6}$ alkyl group,
  (iv) a $C_{1-6}$ alkoxy group optionally substituted by the substituent(s) selected from
    (a) a $C_{6-10}$ aryloxy group optionally substituted by the substituent(s) selected from a halogen atom, a $C_{1-6}$ alkyl group and a nitro group,
    (b) an amino group optionally mono- or di-substituted by $C_{1-6}$ alkoxy-carbonyl group(s),
    (c) a carboxy group,
    (d) a $C_{1-6}$ alkoxy-carbonyl group,
    (e) a carbamoyl group optionally mono- or di-substituted by $C_{7-13}$ aralkyl group(s), and
    (f) a heterocyclic group,
  (v) a $C_{6-10}$ aryl group optionally substituted by nitro group(s),
  (vi) a $C_{6-10}$ aryloxy group optionally substituted by the substituent(s) selected from a halogen atom, a nitro group, a $C_{1-6}$ alkyl group, a $C_{1-6}$ alkoxy group and a cyano group,
  (vii) a $C_{7-13}$ aralkyl group,
  (viii) a $C_{7-13}$ aralkyloxy group,
  (ix) a $C_{6-10}$ aryl-$C_{2-6}$ alkenyl group,
  (x) a heterocyclic group,
  (xi) a heterocyclyloxy group,
  (xii) a heterocyclylcarbonyl group, and
  (xiii) an amino group optionally mono- or di-substituted by $C_{6-10}$ aryl group(s),
(3) a $C_{1-10}$ alkyl group, or
(4) a $C_{2-10}$ alkenyl group;

$B^1$ is a group represented by

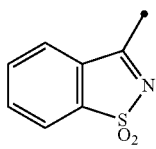

wherein • means a bonding site, which is an optionally substituted;
$X^1$ and $X^2$ are each independently an oxygen atom or a sulfur atom; and
Y and Z are each independently a bond or a spacer having 1 to 6 atoms,
or a salt thereof.

2. The compound or salt of claim 1, wherein the partial structure represented by

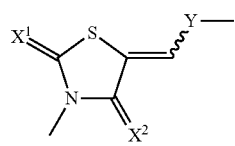

is a partial structure represented by

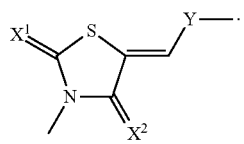

3. The compound or salt of claim 1, wherein A is
(1) a $C_{6-10}$ aryl group optionally substituted by the substituent(s) selected from
(i) a carboxy group,
(ii) a $C_{1-6}$ alkoxy group substituted by the substituent(s) selected from
  (a) a $C_{6-10}$ aryloxy group optionally substituted by the substituent(s) selected from a halogen atom, a $C_{1-6}$ alkyl group and a nitro group,
  (b) an amino group optionally mono- or di-substituted by $C_{1-6}$ alkoxy-carbonyl group(s),
  (c) a carboxy group,
  (d) a $C_{1-6}$ alkoxy-carbonyl group,
  (e) a carbamoyl group optionally mono- or di-substituted by $C_{7-13}$ aralkyl group(s), and
  (f) a heterocyclic group,
(iii) a $C_{6-10}$ aryl group optionally substituted by nitro group(s),
(iv) a $C_{6-10}$ aryloxy group optionally substituted by the substituent(s) selected from a halogen atom, a nitro group, a $C_{1-6}$ alkyl group, a $C_{1-6}$ alkoxy group and a cyano group,
(v) a $C_{7-13}$ aralkyl group,
(vi) a $C_{7-13}$ aralkyloxy group,
(vii) a $C_{6-10}$ aryl-$C_{2-6}$ alkenyl group,
(viii) a heterocyclic group,
(ix) a heterocyclyloxy group,
(x) a heterocyclylcarbonyl group, and
(xi) an amino group optionally mono- or di-substituted by $C_{6-10}$ aryl group(s), or
(2) fluorenyl, furyl, pyridyl or carbazolyl, each of which is optionally substituted by the substituent(s) selected from
(i) a halogen atom,
(ii) a carboxy group,
(iii) a $C_{1-6}$ alkyl group,
(iv) a $C_{1-6}$ alkoxy group optionally substituted by the substituent(s) selected from
  (a) a $C_{6-10}$ aryloxy group optionally substituted by the substituent(s) selected from a halogen atom, a $C_{1-6}$ alkyl group and a nitro group,
  (b) an amino group optionally mono- or di-substituted by $C_{1-6}$ alkoxy-carbonyl group(s),
  (c) a carboxy group,
  (d) a $C_{1-6}$ alkoxy-carbonyl group,
  (e) a carbamoyl group optionally mono- or di-substituted by $C_{7-13}$ aralkyl group(s), and
  (f) a heterocyclic group,
(v) a $C_{6-10}$ aryl group optionally substituted by nitro group(s),
(vi) a $C_{6-10}$ aryloxy group optionally substituted by the substituent(s) selected from a halogen atom, a nitro group, a $C_{1-6}$ alkyl group, a $C_{1-6}$ alkoxy group and a cyano group,
(vii) a $C_{7-13}$ aralkyl group,
(viii) a $C_{7-13}$ aralkyloxy group,
(ix) a $C_{6-10}$ aryl-$C_{2-6}$ alkenyl group,
(x) a heterocyclic group,
(xi) a heterocyclyloxy group,
(xii) a heterocyclylcarbonyl group, and
(xiii) an amino group optionally mono- or di-substituted by $C_{6-10}$ aryl group(s).

4. The compound or salt of claim 1, wherein A is a $C_{6-10}$ aryl group optionally substituted by the substituent(s) selected from
(i) a $C_{1-6}$ alkoxy group substituted by the substituent(s) selected from
  (a) a $C_{6-10}$ aryloxy group optionally substituted by the substituent(s) selected from a halogen atom, a $C_{1-6}$ alkyl group and a nitro group,
  (b) an amino group optionally mono- or di-substituted by $C_{1-6}$ alkoxy-carbonyl group(s),
  (c) a carboxy group,
  (d) a $C_{1-6}$ alkoxy-carbonyl group,
  (e) a carbamoyl group optionally mono- or di-substituted by $C_{7-13}$ aralkyl group(s), and
  (f) a heterocyclic group,
(ii) a $C_{6-10}$ aryl group,
(iii) aryloxy group optionally substituted by the substituent(s) selected a $C_{6-10}$ from a halogen atom, a nitro group and a $C_{1-6}$ alkyl group,
(iv) a $C_{7-13}$ aralkyloxy group,
(v) a heterocyclic group, and
(vi) a heterocyclyloxy group.

5. The compound or salt of claim 1, wherein A is a phenyl group optionally substituted by the substituent(s) selected from
(i) a $C_{1-6}$ alkoxy group substituted by the substituent(s) selected from
  (a) a $C_{6-10}$ aryloxy group optionally substituted by the substituent(s) selected from a nitro group and a $C_{1-6}$ alkyl group,
  (b) an amino group optionally mono- or di-substituted by $C_{1-6}$ alkoxy-carbonyl group(s), (c) a carboxy group, and (d) a $C_{1-6}$ alkoxy-carbonyl group, (ii) a $C_{6-10}$ aryl group, (iii) a $C_{6-10}$ aryloxy group optionally substituted by halogen atom(s), (iv) a $C_{7-13}$ aralkyloxy group, and (v) a heterocyclyloxy group.

6. The compound or salt of claim 1, wherein $X^1$ is a sulfur atom.

7. The compound or salt of claim 1, wherein $X^2$ is an oxygen atom.

8. The compound or salt of claim 1, wherein Y is a bond.

9. The compound or salt of claim 1, wherein Z is —NH—.

10. A compound represented by the formula (II):

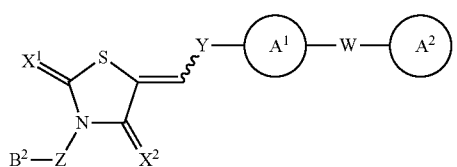

(II)

wherein ring $A^1$ and ring $A^2$ are each independently an optionally substituted benzene ring;

$B^2$ is a group represented by

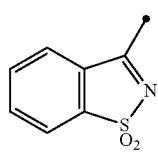

wherein • means a bonding site, which is an optionally substituted;

$X^1$ and $X^2$ are each independently an oxygen atom or a sulfur atom;

Y and Z are each independently a bond or a spacer having 1 to 6 atoms; and

W is an oxygen atom, a sulfur atom, or a group represented by the formula: —$V^1$—$(CH_2)$m-$V^2$— wherein $V^1$ and $V^2$ are each independently a bond, an oxygen atom or a sulfur atom, and m is an integer of 1 to 3, or a salt thereof.

11. The compound or salt of claim 10, wherein the partial structure represented by

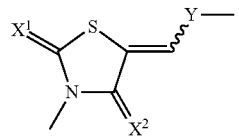

is a partial structure represented by

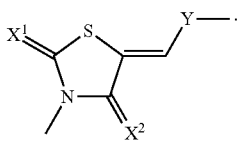

12. The compound or salt of claim 10, wherein ring $A^1$ and ring $A^2$ are both benzene rings.

13. The compound or salt of claim 10, wherein W is an oxygen atom, or a group represented by the formula: —$V^1$—$(CH_2)$m-$V^2$— wherein $V^1$ and $V^2$ are oxygen atoms, and m is an integer of 1 to 3.

14. The compound or salt of claim 10, wherein W is an oxygen atom or —$OCH_2CH_2O$—.

15. The compound or salt of claim 10, wherein $X^1$ is a sulfur atom.

16. The compound or salt of claim 10, wherein $X^2$ is an oxygen atom.

17. The compound or salt of claim 10, wherein Y is a bond.

18. The compound or salt of claim 10, wherein Z is a bond, or a group represented by —$(CH_2)$n$^1$-$V^3$—$(CH_2)$n$^2$- wherein $V^3$ is a bond, —CO—, —NH—, —NHCO— or —CONH—, and n$^1$ and n$^2$ are each independently an integer of 0 to 2.

19. The compound or salt of claim 10, wherein Z is a bond, —NH—, —CONH—, —$COCH_2$—, —$CH_2$— or —$(CH_2)_2$—.

20. A pharmaceutical composition comprising the compound or salt of claim 1 and a pharmacologically acceptable carrier.

21. A pharmaceutical composition comprising the compound or salt of claim 10 and a pharmacologically acceptable carrier.

22. 3-[(4-Oxo-5-(4-phenoxybenzylidene)-2-thioxothiazolidin-3-yl)amino]-1,2-benzisothiazole 1,1-dioxide or a salt thereof.

23. 3-([5-(4-Bromobenzylidene)-4-oxo-2-thioxothiazolidin-3-yl)amino]-1,2-benzisothiazole 1,1-dioxide or a salt thereof.

24. 3-([5-(2,4-Dinitrobenzylidene)-4-oxo-2-thioxothiazolidin-3-yl)amino]-1,2-benzisothiazole 1,1-dioxide or a salt thereof.

25. 3-[(4-Oxo-5-(3-phenoxybenzylidene)-2-thioxothiazolidin-3-yl)amino]-1,2-benzisothiazole 1,1-dioxide or a salt thereof.

* * * * *

UNITED STATES PATENT AND TRADEMARK OFFICE
CERTIFICATE OF CORRECTION

| | | |
|---|---|---|
| PATENT NO. | : 9,056,862 B2 | Page 1 of 1 |
| APPLICATION NO. | : 14/116152 | |
| DATED | : June 16, 2015 | |
| INVENTOR(S) | : Tohru Kataoka et al. | |

It is certified that error appears in the above-identified patent and that said Letters Patent is hereby corrected as shown below:

Claims

Col. 126, Claim 4, Lines 17-19: delete "(iii) aryloxy group optionally substituted by the substituent(s) selected a $C_{6-10}$ from a halogen atom, a nitro group and a $C_{1-6}$ alkyl group," and insert --(iii) a $C_{6-10}$ aryloxy group optionally substituted by the substituent(s) selected from a halogen atom, a nitro group and a $C_{1-6}$ alkyl group,--

Signed and Sealed this
Twenty-third Day of February, 2016

Michelle K. Lee
*Director of the United States Patent and Trademark Office*